United States Patent
Lin

(10) Patent No.: US 9,994,913 B2
(45) Date of Patent: Jun. 12, 2018

(54) METHODS AND COMPOSITIONS FOR DETECTING AND TREATING DRUG RESISTANT AKT MUTANT

(71) Applicant: Genentech, Inc., South San Francisco, CA (US)

(72) Inventor: Kui Lin, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days. days.

(21) Appl. No.: 14/832,594

(22) Filed: Aug. 21, 2015

(65) Prior Publication Data

US 2016/0153049 A1 Jun. 2, 2016

Related U.S. Application Data

(63) Continuation of application No. PCT/US2014/017948, filed on Feb. 24, 2014.

(60) Provisional application No. 61/769,108, filed on Feb. 25, 2013.

(51) Int. Cl.
*A61K 31/517* (2006.01)
*C12Q 1/68* (2018.01)
*A61K 31/436* (2006.01)
*A61K 31/5377* (2006.01)

(52) U.S. Cl.
CPC .......... *C12Q 1/6886* (2013.01); *A61K 31/436* (2013.01); *A61K 31/517* (2013.01); *A61K 31/5377* (2013.01); *C12Q 2600/106* (2013.01); *C12Q 2600/156* (2013.01); *C12Q 2600/158* (2013.01)

(58) Field of Classification Search
CPC .................................. A61K 31/517
See application file for complete search history.

(56) References Cited

FOREIGN PATENT DOCUMENTS

| WO | 2008/049022 A2 | 4/2008 |
| WO | 2009/103790 A2 | 8/2009 |
| WO | 2012/135749 A2 | 10/2012 |

OTHER PUBLICATIONS

Troxell et al. Modern Pathology, 2010, vol. 23, pp. 27-37.*
Askham et al. Oncogene, 2010, vol. 29, pp. 150-155.*
Nakatani et al. The Journal of Biological Chemistry, 1999, vol. 274, No. 31, pp. 21528-21532.*
Wallin et al. Mol. Cancer Ther., 2011, vol. 10, No. 12, pp. 2426-2436.*
Blake et al., "Discovery and preclinical pharmacology of a selective ATP-competitive Akt inhibitor (GDC-0068) for the treatment of human tumors" J Med Chem. 55(18)::8110-27 ( 2012).
Degtyarev et al., "Akt inhibition promotes autophagy and sensitizes PTEN-null tumors to lysosomotropic agents" J Cell Biol. 183(1):101-16 ( 2008).
Degtyarev et al., "Autophagy, an Achilles' heel AKTing against cancer?" Autophagy 5(3):415-8 ( 2009).
Ellis et al., "Migration stimulating factor (MSF) promoted fibroblast migration by inhibiting AKT" Cell Signal 22:1655-1659 ( 2010).
Flatley et al., "PIK3CA-AKT pathway mutations in micropapillary breast carcinoma" Hum Pathol. 44(7):1320-7 ( 2013).
Green et al., "Use of AKT inhibitor and a drug-resistant mutant validates a critical role for protein kinase B/AKT in the insulin-dependent regulation of glucose and ststem a amino acid uptake" J Biol Chem 283(41):27653-27667 (Oct. 10, 2008).
ISR for PCT/US2014/017948, dated Jul. 8, 2014.
Kim et al., "Mutational analysis of oncogenic AKT E17K mutation in common solid cancers and acute leukaemias" Br J Cancer 98(9):1533-5 (2008).
Lin et al., "Targeting activated Akt with GDC-0068, a novel selective Akt inhibitor that is efficacious in multiple tumor models" Clin Cancer Res. 19(7):1760-72 ( 2013).
Lin, "An ATP-site on-off switch that restricts phosphatase accessibility of Akt" Sci Signal. 5(223):ra37 ( 2012).
Lin, "The Akt DUBbed InAktive" Sci Signal. 6(257):pe1 ( 2013).
Parikh et al., "Disruption of PH-kinase domain interactions leads to oncogenic activation of AKT in human cancers" Proc Natl Acad Sci U S A. 109(47):19368-73 ( 2012).
Saji et al., "Akt1 contains a functional leucine-rich nuclear export sequence" Biochem Biophys Res Commun. 332(1):167-73 ( 2005).
Toker et al., "Akt signaling and cancer:surviving but not moving on" Cancer Res. 66(8):3963-6 ( 2006).

* cited by examiner

*Primary Examiner* — James D. Anderson
(74) *Attorney, Agent, or Firm* — Viksnins Harris Padys Malen LLP

(57) ABSTRACT

Methods for identifying or diagnosing AKT inhibitor resistant cancers and methods an compositions for treating.

17 Claims, 7 Drawing Sheets

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ccagccccca ccagtccact                                               20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cgccaaggag atcatgcagc                                               20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gctgcatgat ctccttggcg                                               20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
agatagctgg tgacagacag                                               20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cgtggagaga tcatctgagg                                               20

<210> SEQ ID NO 6
<211> LENGTH: 20
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 6
tcgaaaaggt caagtgctac                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tggtgcagcg gcagcggcag                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ggcgcgagcg cgggcctagc                                              20
```

METHODS AND COMPOSITIONS FOR DETECTING AND TREATING DRUG RESISTANT AKT MUTANT

CROSS-REFERENCE TO RELATED APPLICATIONS

This application is a continuation of International Application No. PCT/US2014/017948 having an international filing date of Feb. 24, 2014, and which claims benefit under 35 U.S.C. § 119 to U.S. Provisional Patent Application No. 61/769,108, filed Feb. 25, 2013, the contents of both of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Jan. 20, 2016, is named P05567-US-1 SL.txt and is 2,224 bytes in size.

FIELD OF THE INVENTION

The invention relates to the field of tumor growth, tumor type and drug resistance. The invention relates to inhibitors and diagnostics markers for tumors, and uses of such for the diagnosis and treatment of cancer, drug resistant cancer, and tumor growth.

BACKGROUND OF THE INVENTION

Malignant tumors (cancers) are a leading cause of death in the United States, after heart disease (see, e.g., Boring et al., CA Cancel J. Clin. 43:7(1993)). Cancer is characterized by the increase in the number of abnormal, or neoplastic, cells derived from a normal tissue which proliferate to form a tumor mass, the invasion of adjacent tissues by these neoplastic tumor cells, and the generation of malignant cells which eventually spread via the blood or lymphatic system to regional lymph nodes and to distant sites via a process called metastasis. In a cancerous state, a cell proliferates under conditions in which normal cells would not grow. Cancer manifests itself in a wide variety of forms, characterized by different degrees of invasiveness and aggressiveness.

Depending on the cancer type, patients typically have several treatment options available to them including chemotherapy, radiation and antibody-based drugs. Diagnostic methods useful for predicting clinical outcome from the different treatment regimens would greatly benefit clinical management of these patients. Several studies have explored the correlation of gene expression with the identification of specific cancer types, e.g., by mutation-specific assays, microarray analysis, qPCR, etc. Such methods may be useful for the identification and classification of cancer presented by a patient.

Akt is the human homologue of the protooncogene v-akt of the acutely transforming retrovirus AKT8. Due to its high sequence homology to protein kinases A and C, Akt is also called Protein Kinase B (PKB) and Related to A and C (RAC). Three isoforms of Akt are known to exist, namely Akt1, Akt2 and Akt3, which exhibit an overall homology of 80% (Staal, S. P. (1987) Proc. Natl. Acad. Sci. 84:5034; Nakatani, K. (1999) Biochem. Biophys. Res. Commun. 257:906; Li et al (2002) Current Topics in Med. Chem. 2:939-971; WO 2005/113762). The Akt isoforms share a common domain organization that consists of a pleckstrin homology domain at the N-terminus, a kinase catalytic domain, and a short regulatory region at the C-terminus. In addition, both Akt2 and Akt3 exhibit splice variants. Upon recruitment to the cell membrane by PtdInd(3,4,5)P$_3$, Akt is phosphorylated (activated) by PDK1 at T308, T309 and T305 for isoforms Akt1 (PKBα), Akt2 (PKBβ) and Akt3 (PKBγ), respectively, and at S473, S474 and S472 for isoforms Akt1, Akt2 and Akt3, respectively. Such phosphorylation occurs by an as yet unknown kinase (putatively named PDK2), although PDK1 (Balendran, A., (1999) Curr. Biol. 9:393), autophosphorylation (Toker, A. (2000) J. Biol. Chem. 275:8271) and integrin-linked kinase (ILK) (Delcommenne, M. (1998) Proc. Natl. Acad. Sci. USA, 95:11211) have been implicated in this process. Akt activation requires its phosphorylation on residue Ser 473 in the C-terminal hydrophobic motif (Brodbeck et al (1999) J. Biol. Chem. 274:9133-9136; Coffer et al (1991) Eur. J. Biochem. 201:475-481; Alessi et al (1997) Curr. Biol. 7:261-269). Although monophosphorylation of Akt activates the kinase, bis(phosphorylation) is required for maximal kinase activity.

Akt is believed to assert its effect on cancer by suppressing apoptosis and enhancing both angiogenesis and proliferation (Toker et al. (2006) Cancer Res. 66(8):3963-3966). Akt is overexpressed in many forms of human cancer including, but not limited to, colon (Zinda et al (2001) Clin. Cancer Res. 7:2475), ovarian (Cheng et al (1992) Proc. Natl. Acad. Sci. USA 89:9267), brain (Haas Kogan et al (1998) Curr. Biol. 8:1195), lung (Brognard et al (2001) Cancer Res. 61:3986), pancreatic (Bellacosa et al (1995) Int. J. Cancer 64:280-285; Cheng et al (1996) Proc. Natl. Acad. Sci. 93:3636-3641), prostate (Graff et al (2000) J. Biol. Chem. 275:24500) and gastric carcinomas (Staal et al (1987) Proc. Natl. Acad. Sci. USA 84:5034-5037).

Therefore, it would be highly advantageous to have molecular-based diagnostic methods, and compositions, that can be used to identify, and treat, subjects with resistance to anti-AKT treatment.

SUMMARY OF THE INVENTION

The methods of the present invention can be utilized in a variety of settings, including, for example, identifying, diagnosing and treating tumors and cancer cells resistant to AKT inhibitors.

One apsect includes a method for detecting resistance to the therapeutic effects of an AKT inhibitor in a cancer cell, comprising detecting the presence of a mutation in the cell comprising an AKT1 or PRAS40 mutation, wherein the presence of a mutation indicates that the cancer cell has become or will become resistant to the AKT inhibitor.

In certain embodiments, the presence of the mutation is detected after treatment with the AKT inhibitor In certain embodiments, the AKT1 mutation comprises a W80.

In certain embodiments, the W80 mutation comprises a cysteine residue change.

Certain embodiments further comprise detecting the expression levels of AKT3.

The method of claims 1-5, further comprising detecting overexpression of AKT3.

In certain embodiments, the AKT inhibitor is allosteric inhibitor.

In certain embodiments, the allosteric inhibitor is MK-2206.

Certain embodiments comprise administering an effective amount of a PI3k or mTOR inhibitor to the cancer cell.

In certain embodiments, the PRAS40 mutation comprises a stop codon.

In certain embodiments, the mutation comprises a 178 stop codon.

In certain embodiments, the AKT inhibitor is an ATP competitive inhibitor.

In certain embodiments, the AKT inhibitor is GDC-0068 or GSK2110183.

In certain embodiments, the AKT3 expression level is mRNA expression level.

In certain embodiments, the mRNA expression level is measured using microarray or qRT-PCR.

In certain embodiments, the change in the mRNA expression level is an increase.

Certain embodiments comprise administering an effective amount of a PI3k inhibitor selected from GDC-0941 and GDC-0980.

Certain embodiments comprise administering an effective amount of a mTOR inhibitor selected from rapamyacin.

In certain embodiments, the cancer is selected from the group consisting of mesothelioma, endometrial, pancreatic, breast, lung, ovarian, prostate, melanoma, gastric, colon, renal, head and neck, and giloma.

In certain embodiments, the cancer is associated with PTEN mutation.

In certain embodiments, the cancer is associated with PTEN low or null status.

In certain embodiments, the cancer is associated with AKT mutation, overexpression or amplification.\

In certain embodiments, the cancer is associated with PI3K mutation.

In certain embodiments, the cancer is associated with Her2/ErbB2 amplification.

In certain embodiments, the cancer cell is a circulating tumor cell (CTC).

In certain embodiments, the detecting further comprising detecting the mutation by pCR.

Any embodiment described herein or any combination thereof applies to any and all methods and compositions described herein.

As revealed by the RNA-seq experiment, the parental LNCaP cells do not express Akt3, nor do the GDC-0068 resistant clones or parental cells treated with either inhibitors. The MK-2206 resistant cells mutated Akt1 and gained expression of Akt3 to overcome the inhibitory effect of the allosteric inhibitor.

Figure 1:
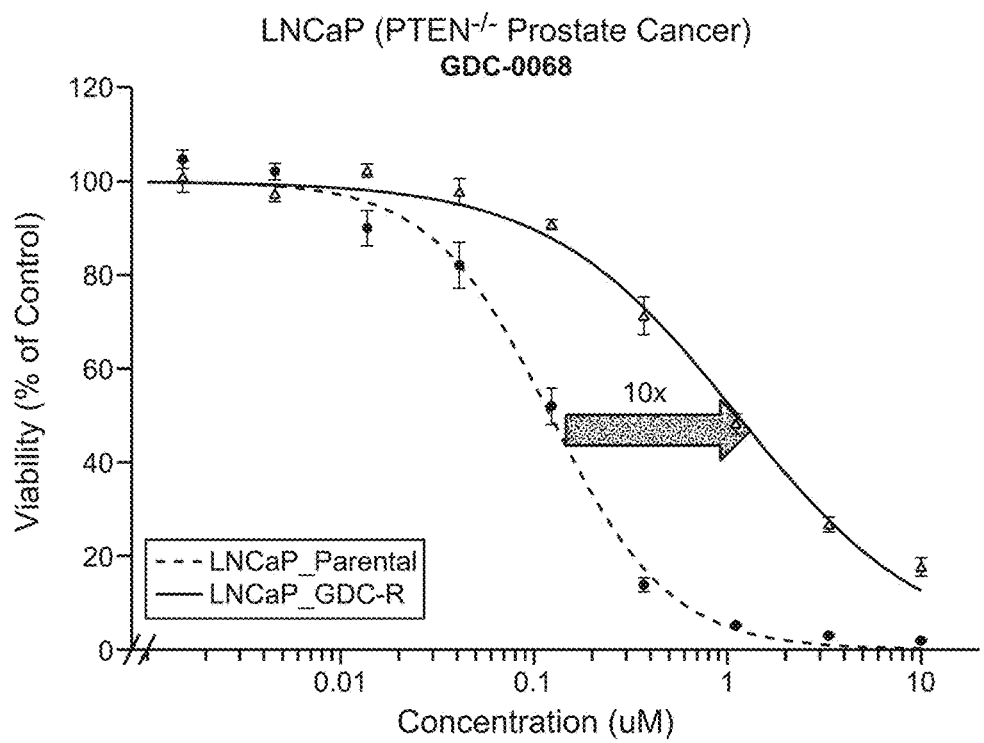
FIGS. 1-2 shows dose response curves for AKT inhibitors GDC-0068 ((S)-2-(4-chlorophenyl)-1-(4-((5R,7R)-7-hydroxy-5-methyl-6,7-dihydro-5H-cyclopenta [d]pyrimi din-4-yl)piperazin-1-yl)-3-(isopropylamino)propan-1-one) and MK2206 (8-[4-(1-aminocyclobutyl)phenyl]-9-phenyl-1,2,4-triazolo[3,4-f][1,6]naphthyridin-3(2H)-one) in a prostate cancer cell line (LNCaP cells) in parental (e.g. reference cells) and in AKT inhibitor cells (e.g. sample cells). Resistant clones to both inhibitors were derived from populations of cancer cells treated with increasing doses of AKT inhibitor over time. For GDC-0068, cells that are ~10× less sensitive were cloned. For MK2206, cells that are ~40× less sensitive were cloned.
Figure 2:
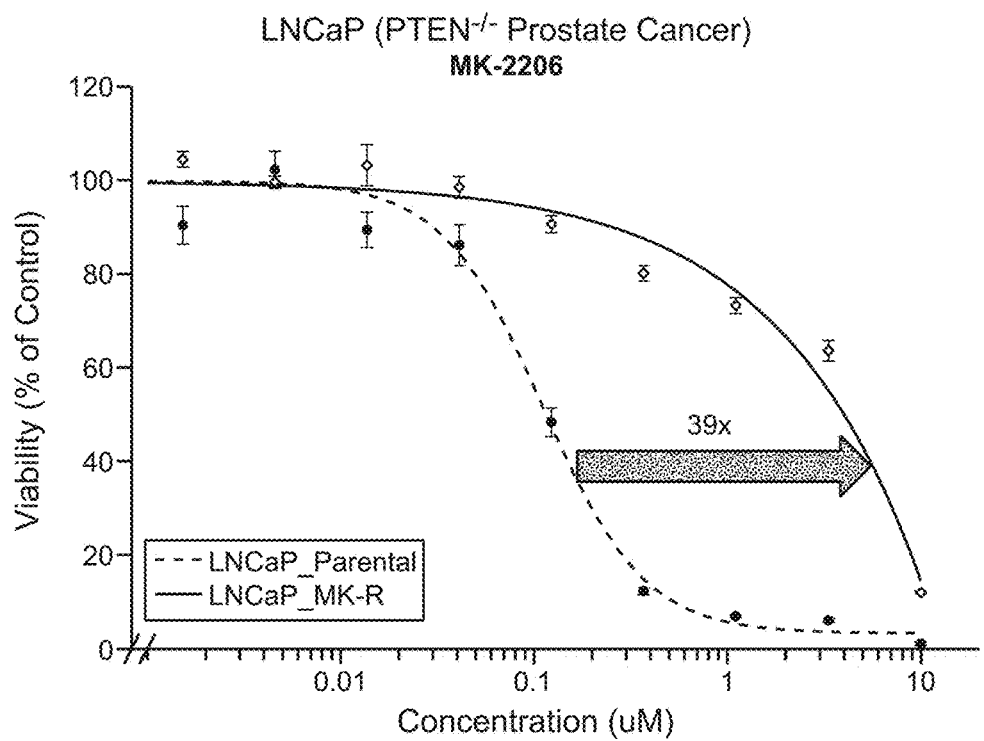
Figure 3:
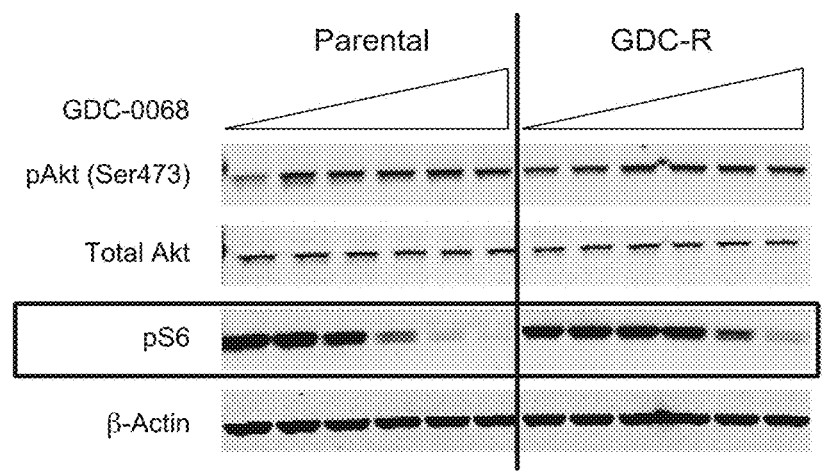
FIGS. 3-4 show Western blot analysis of AKT inhibitor dosed to cancer cells (LNCaP cells). The GDC-0068 resistant cells still bind to the inhibitor, but GDC-0068 is less potent at inhibiting the downstream pS6 (i.e. the cancer cells have become resistant). Similarly, the MK2206 resistant cells lost the inhibition of pS6 induced by MK2206, in addition, MK2206 failed to inhibit Akt phosphorylation as it could in the parental lines. The resistant clones and pools by exome-seq were analyzed, and 2 mutations were found, one is in W80, which is mutated into a cysteine residue, the other is in the Akt substrate PRAS40, with a stop codon at position 178. The Akt1 mutation occurred in all of the MK2206 clones and the PRAS40 mutation occured in all of the GDC-0068 resistant clones.
Figure 4:
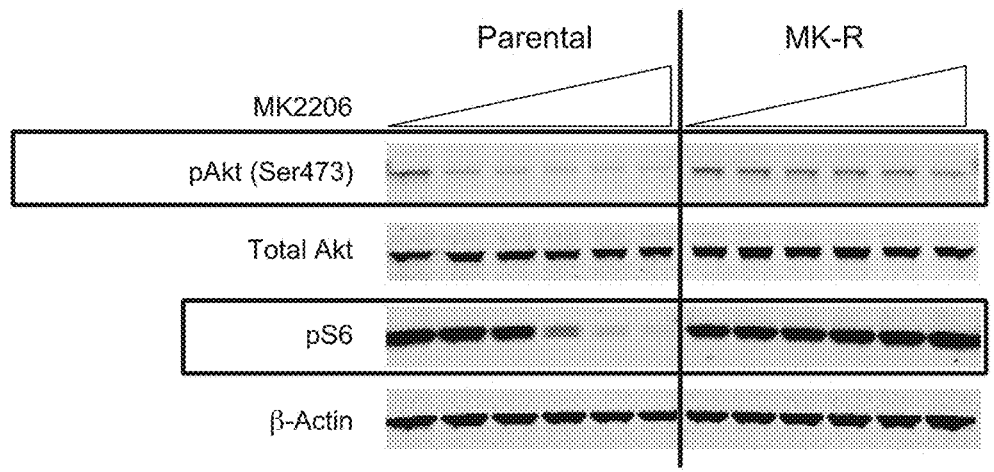
Figure 5:
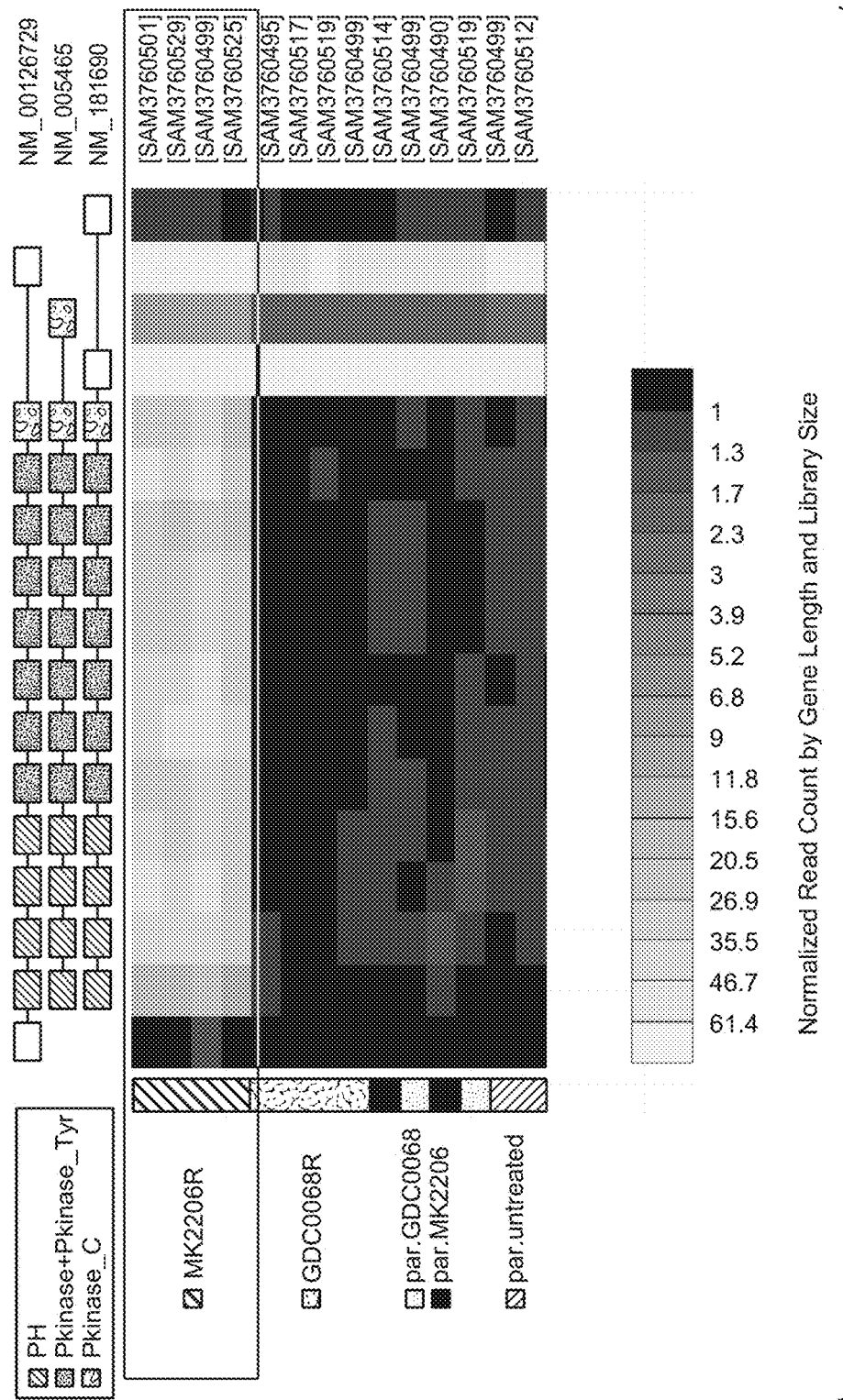
FIG. 5 shows LNCaP MK2206 resistnat clones also gained Akt3 expression as shown by RNA seq data. This demonstrates that cells resistant to AKT inhibitor (e.g. MK2206) can alos have aberrant expression of AKT proteins, e.g. AKT3.
Figure 6:
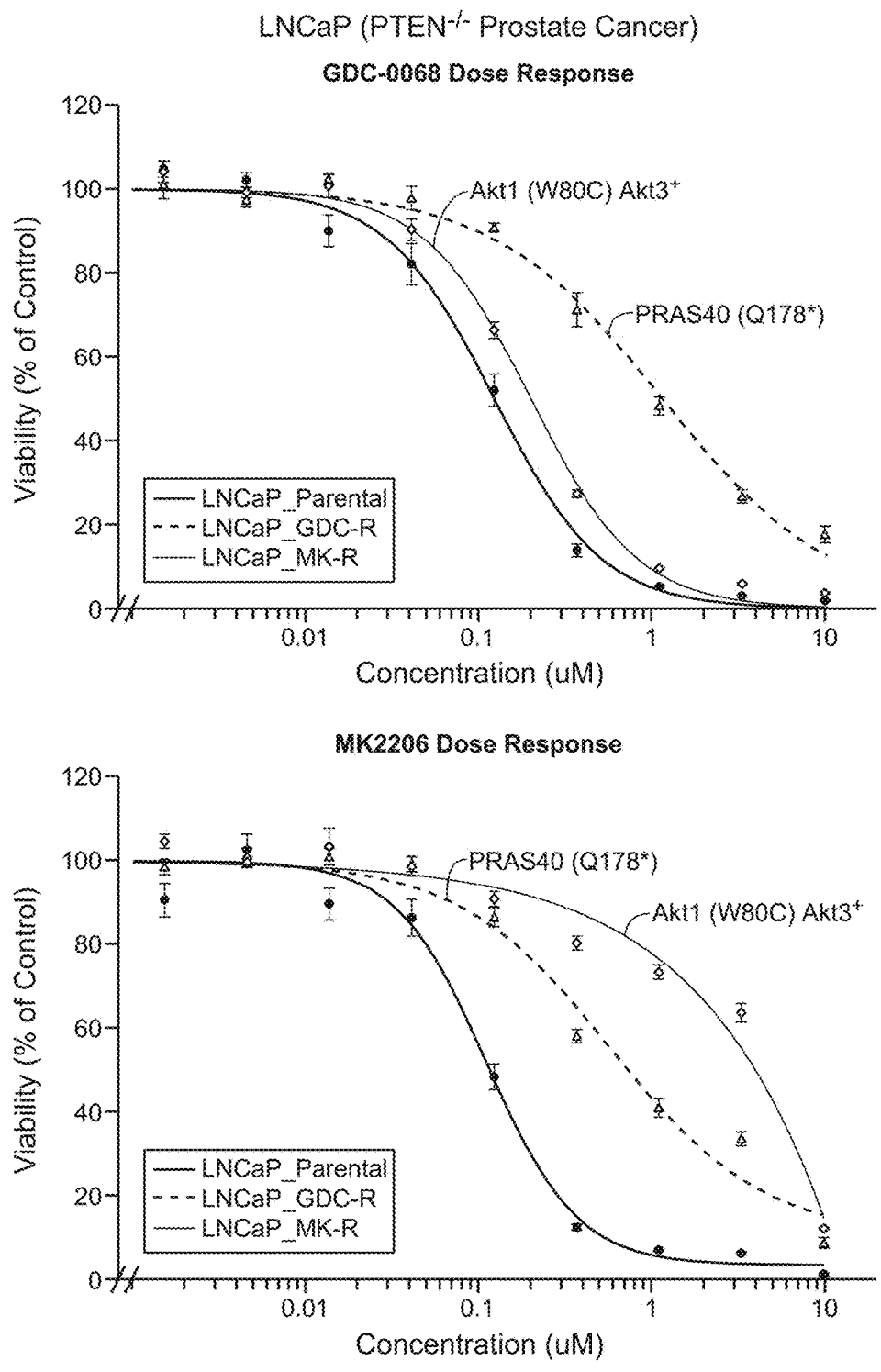

FIG. 6 shows dose response curves of LNCap cells that are parental and resistant to AKT inhibitors when treated with additional AKT inhibitors. Akt inhibitor resistance in LNCaP cells remains dependent on the Akt pathway activity in cases of resistance to both GDC-0068 and MK-2206. The MK2206-resistant cells are still sensitive to GDC-0068, consistent with GDC-0068 targeting the ATP site and inhibiting all 3 Akt equipotently. The GDC-0068-sensitive cells, on the other hand, is similarly resistant to MK2206 as GDC-0068, consistent with the mutation is downstream of Akt.

Cancer cells resistant toATP competitive inhibitors, e.g. GDC-0068 activate mTORC 1 epistatic to Akt. MK-2206 resistant cells abrogate allosteric inhibition of Akt itself, but remain sensitvie to ATP competitive AKT inhibitors such as GDC-0068.

Figure 7:
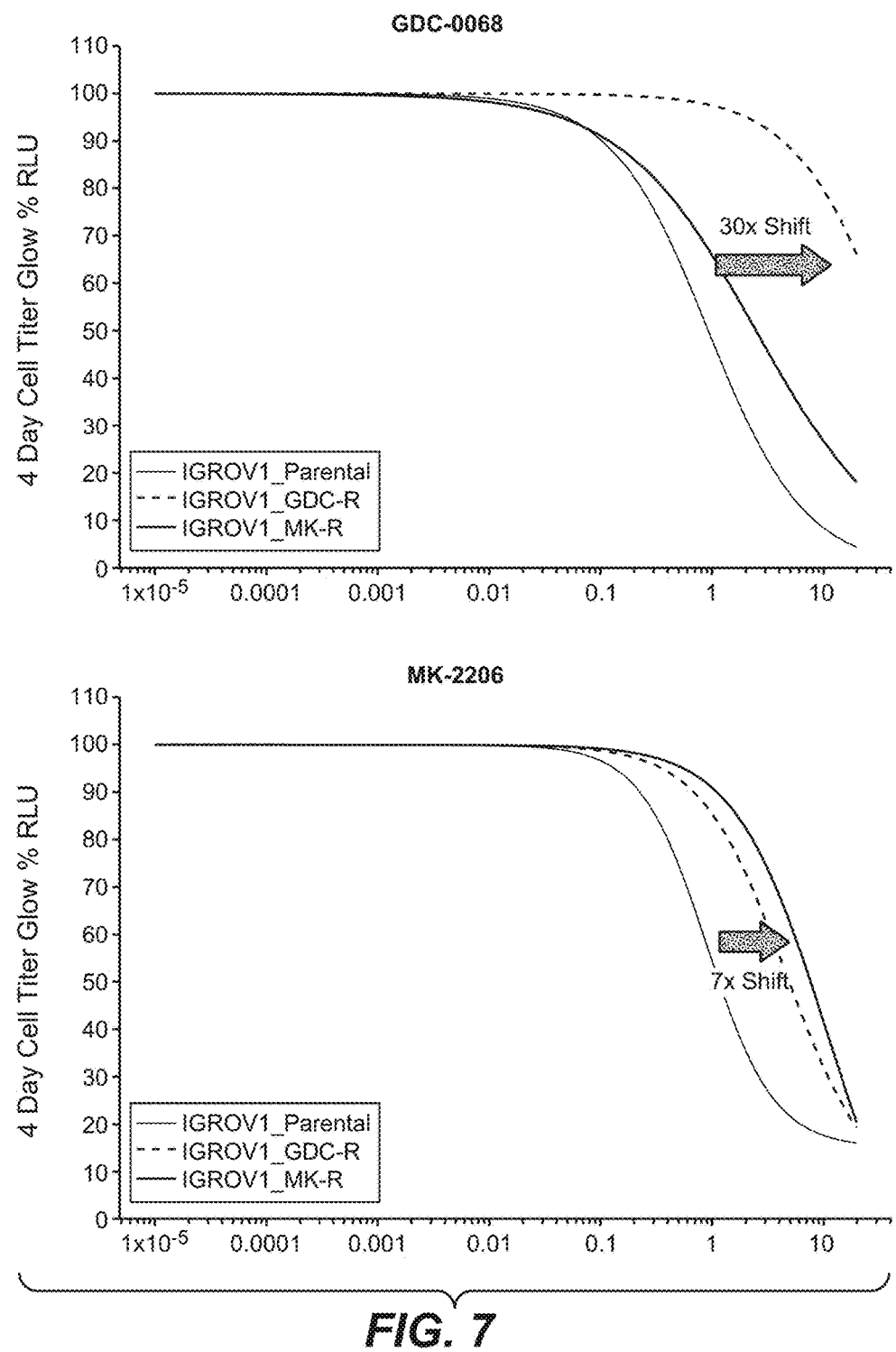
Figure 8:
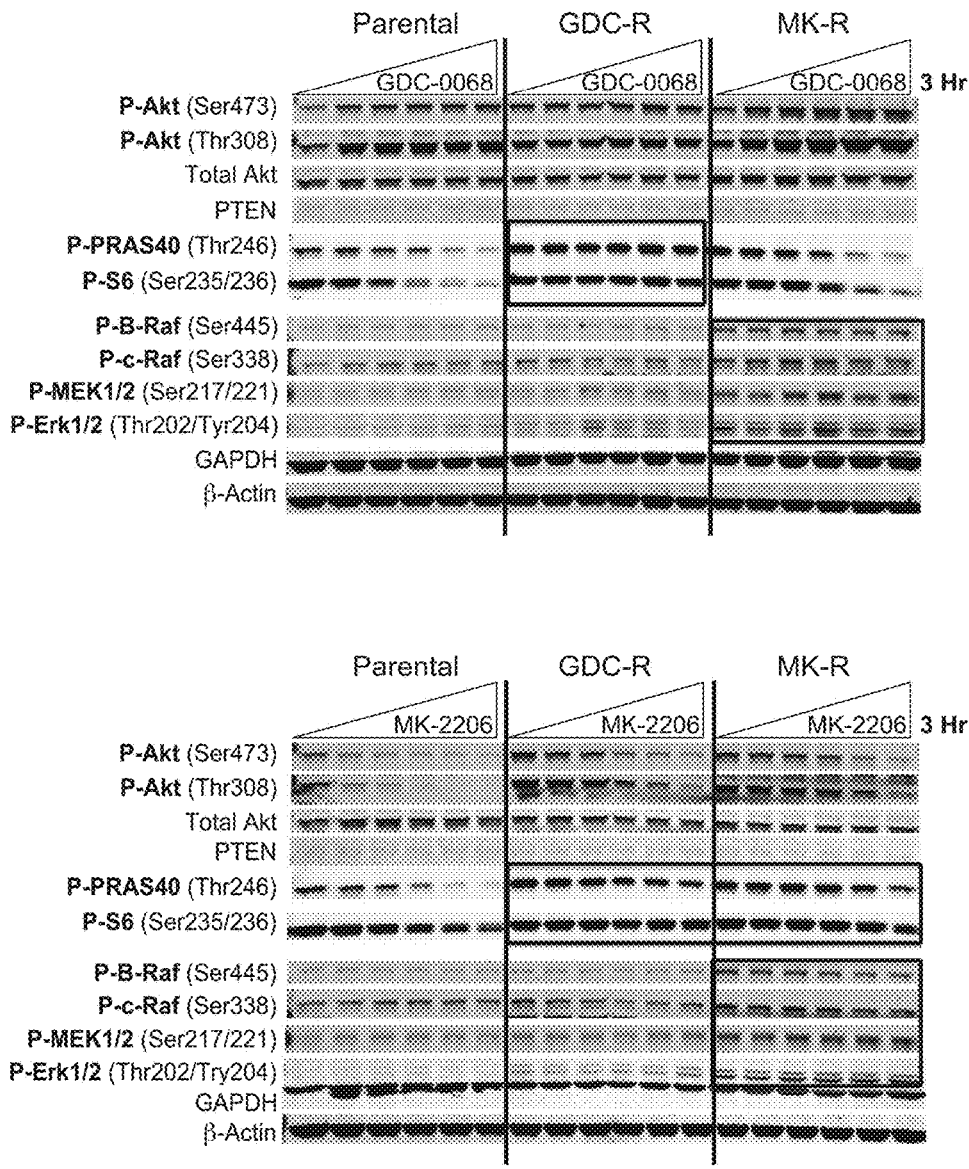

FIGS. 7-8 show results of ovarian cancer cells to treatment of AKT inhibitors, e.g. after gaining resistance to them (IGROV1 (ovarian, PI3K mutant O1069W, PTEN heterozygous cells). The cells resistant to GDC0068 and MK2206 are equally resistant to allosteric inhibition (e.g. MK2206), while cells resistant to GDC0068 are more resistant to GDC-0068 than MK2206.

Figure 9:
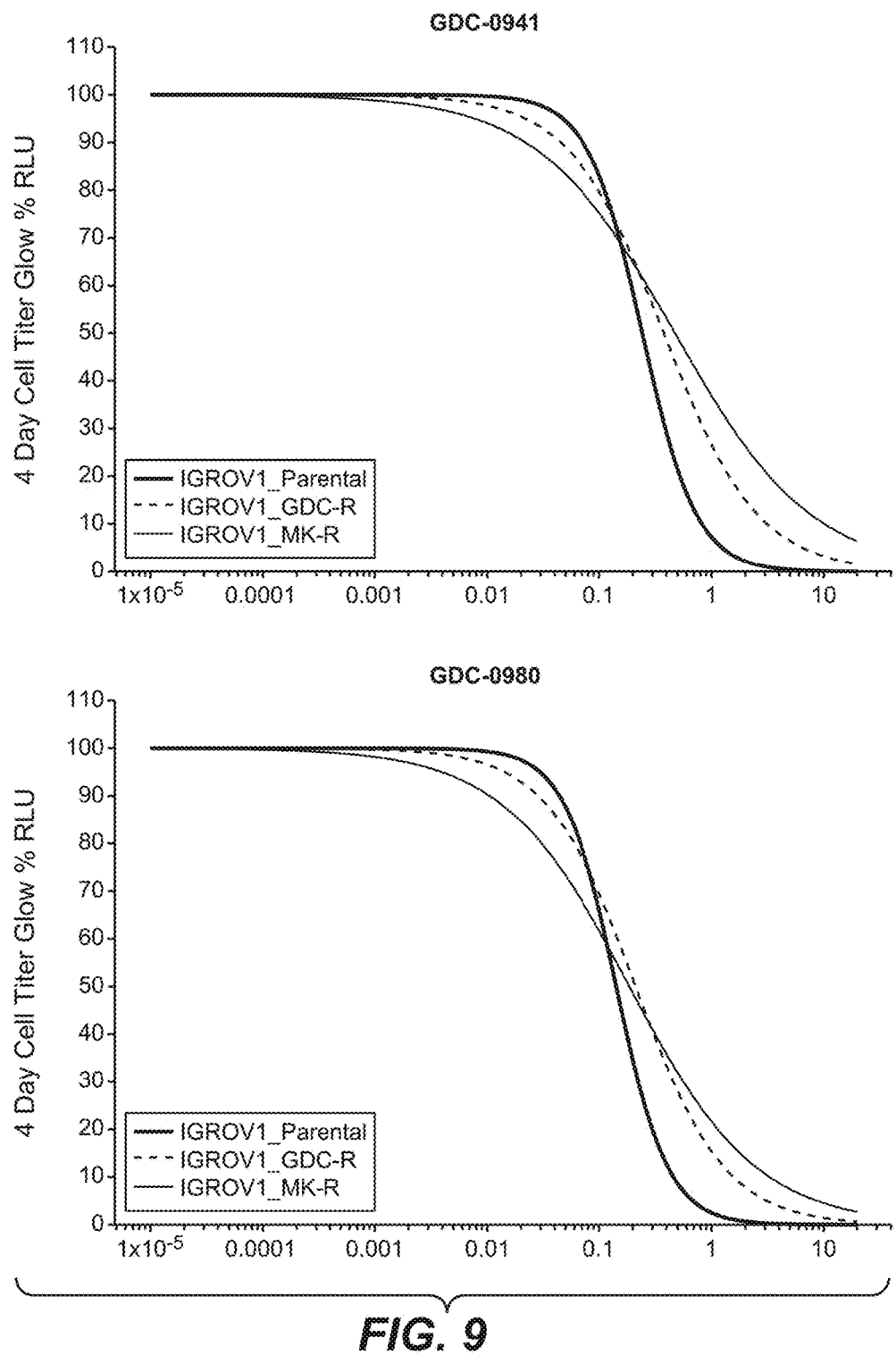

FIG. 9 shows both GDC-0941 and GDC-0980 remain potent to all IGROV1 lines, parental and resistant. This demonstrates that after cells become resistant to AKT inhibitors, a patient's cancer may be treated by administering a PI3k or mTOR inhibitor to treat the AKT-resistant cancer.

DETAILED DESCRIPTION

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture:*

*Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); PCR: *The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); Using Antibodies: A Laboratory Manual (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

Unless defined otherwise, technical and scientific terms used herein have the same meaning as commonly understood by one of ordinary skill in the art. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application. All references cited herein, including patent applications and publications, are incorporated by reference in their entirety.

Definitions

For purposes of interpreting this specification, the following definitions will apply and whenever appropriate, terms used in the singular will also include the plural and vice versa. It is to be understood that the terminology used herein is for the purpose of describing particular embodiments only, and is not intended to be limiting. In the event that any definition set forth below conflicts with any document incorporated herein by reference, the definition set forth below shall control.

"Test sample" or "sample" herein refers to a composition that is obtained or derived from a subject of interest that contains a cellular and/or other molecular entity that is to be characterized and/or identified, for example based on physical, biochemical, chemical and/or physiological characteristics. In one embodiment, the definition encompasses blood and other liquid samples of biological origin and tissue samples such as a biopsy specimen or tissue cultures or cells derived there from. The source of the tissue sample may be solid tissue as from a fresh, frozen and/or preserved organ or tissue sample or biopsy or aspirate; blood or any blood constituents; bodily fluids; and cells from any time in gestation or development of the subject or plasma.

In another embodiment, the definition includes biological samples that have been manipulated in any way after their procurement, such as by treatment with reagents, solubilization, or enrichment for certain components, such as proteins or polynucleotides, or embedding in a semi-solid or solid matrix for sectioning purposes. For the purposes herein a "section" of a tissue sample is meant a single part or piece of a tissue sample, e.g. a thin slice of tissue or cells cut from a tissue sample.

Samples include, but not limited to, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, urine, cerebro-spinal fluid, saliva, sputum, tears, perspiration, mucus, tumor lysates, and tissue culture medium, as well as tissue extracts such as homogenized tissue, tumor tissue, and cellular extracts.

In one embodiment, the test sample is a clinical sample. In another embodiment, the test sample is used in a diagnostic assay. In some embodiments, the test sample is obtained from a primary or metastatic tumor. Tissue biopsy is often used to obtain a representative piece of tumor tissue. Alternatively, tumor cells can be obtained indirectly in the form of tissues or fluids that are known or thought to contain the tumor cells of interest. For instance, biological samples of lung cancer lesions may be obtained by resection, bronchoscopy, fine needle aspiration, bronchial brushings, or from sputum, pleural fluid or blood. In one embodiment, the test sample comprises circulating tumor cells (CTCs), for example those CTCs from a patient's serum.

In one embodiment, a test sample is obtained from a subject or patient prior to, during, and/or after therapy with an AKT inhibitor. In certain embodiments, a test sample is obtained after cancer has metastasized.

A "reference sample", as used herein, refers to reference any sample, standard, or level that is used for comparison purposes. In one embodiment, a reference sample is obtained from a healthy and/or non-diseased part of the body of the same subject or patient. In another embodiment, a reference sample is obtained from an untreated tissue and/or cell of the body of the same subject or patient.

In certain embodiments, a reference sample copmrises a tumor or cancer cell that is responsive to AKT inhibitor therapy. In certain embodiments, the AKT inhibitor therapy comprises GDC-0068, MK2206 or GSK2110183.

In certain embodiments, a reference sample is a single sample or combined multiple samples from the same subject or patient that are obtained at one or more different time points than when the test sample is obtained. For example, a reference sample is obtained at an earlier time point from the same subject or patient than when the test sample is obtained. Such reference sample may be useful if the reference sample is obtained during initial diagnosis of cancer and the test sample is later obtained when the cancer becomes metastatic.

In one embodiment, CTCs are obtained from a patient at various timepoints before, during and after treatment with an AKT inhibitor, e.g. GDC-0068, MK2206 or GSK2110183, and the mutational status of AKT and PRAS40 are detected (e.g. by pCR, Western, or IHC).

In certain embodiments, a reference sample is a combined multiple samples from one or more healthy individuals who are not the subject or patient. In certain embodiments, a reference sample is a combined multiple samples from one or more individuals with cancer who are not the subject or patient. In certain embodiments, a reference sample is pooled RNA samples from normal tissues from one or more individuals who are not the subject or patient. In certain embodiments, a reference sample is pooled RNA samples from tumor tissues from one or more individuals with cancer who are not the subject or patient.

Expression levels/amount of a gene or biomarker can be determined qualitatively and/or quantitatively based on any suitable criterion known in the art, including but not limited to mRNA, cDNA, proteins, protein fragments and/or gene copy number. In certain embodiments, expression/amount of a gene or biomarker in a first sample is increased as compared to expression/amount in a second sample. In certain embodiments, expression/amount of a gene or biomarker in a first sample is decreased as compared to expression/amount in a second sample. In certain embodiments, the second sample is reference sample.

In certain embodiments, the term "increase" refers to an overall increase of 5%, 10%, 15%, 20%, 25%, 30%, 40%, 50%, 60%, 70%, 80%, 85%, 90%, 95%, 96%, 97%, 98%, 99% or greater, in the level of protein or nucleic acid, detected by standard art known methods such as those described herein, as compared to a reference sample. In certain embodiments, the term increase refers to the increase in expression level/amount of a gene or biomarker in the sample wherein the increase is at least about 1.25×, 1.5×, 1.75×, 2×, 3×, 4×, 5×, 6×, 7×, 8×, 9×, 10×, 25×, 50×, 75×, or 100× the expression level/amount of the respective gene or biomarker in the reference sample.

In certain embodiments, the term "decrease" herein refers to an overall reduction of 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or greater, in the level of protein or nucleic acid, detected by standard art known methods such as those described herein, as compared to a reference sample. In certain embodiments, the term decrease refers to the decrease in expression level/amount of a gene or biomarker in the sample wherein the decrease is at least about 0.9×, 0.8×, 0.7×, 0.6×, 0.5×, 0.4×, 0.3×, 0.2×, 0.1×, 0.05×, or 0.01× the expression level/amount of the respective gene or biomarker in the reference sample.

The word "label" when used herein refers to a compound or composition which is conjugated or fused directly or indirectly to a reagent such as a nucleic acid probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable.

In certain embodiments, by "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of gene expression analysis or protocol, one may use the results of the gene expression analysis or protocol to determine whether a specific therapeutic regimen should be performed.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs.

"Oligonucleotide," as used herein, generally refers to short, generally single-stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

An "isolated" nucleic acid molecule is a nucleic acid molecule that is identified and separated from at least one contaminant nucleic acid molecule with which it is ordinarily associated in the natural source of the polypeptide nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the polypeptide where, for example, the nucleic acid molecule is in a chromosomal location different from that of natural cells.

A "primer" is generally a short single stranded polynucleotide, generally with a free 3'-OH group, that binds to a target potentially present in a sample of interest by hybridizing with a target sequence, and thereafter promotes polymerization of a polynucleotide complementary to the target.

The term "housekeeping gene" refers to a group of genes that codes for proteins whose activities are essential for the maintenance of cell function. These genes are typically similarly expressed in all cell types.

The term "array" or "microarray," as used herein refers to an ordered arrangement of hybridizable array elements, preferably polynucleotide probes (e.g., oligonucleotides), on a substrate. The substrate can be a solid substrate, such as a glass slide, or a semi-solid substrate, such as nitrocellulose membrane. The nucleotide sequences can be DNA, RNA, or any permutations thereof.

A "native sequence" polypeptide comprises a polypeptide having the same amino acid sequence as a polypeptide derived from nature. Thus, a native sequence polypeptide can have the amino acid sequence of naturally occurring polypeptide from any mammal. Such native sequence polypeptide can be isolated from nature or can be produced by recombinant or synthetic means. The term "native sequence" polypeptide specifically encompasses naturally occurring truncated or secreted forms of the polypeptide (e.g., an extracellular domain sequence), naturally occurring variant forms (e.g., alternatively spliced forms) and naturally occurring allelic variants of the polypeptide.

An "isolated" polypeptide or "isolated" antibody is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In certain embodiments, the polypeptide will be purified (1) to greater than 95% by weight of polypeptide as determined by the Lowry method, or more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue, or silver stain. Isolated polypeptide includes the polypeptide in situ within recombinant cells since at least one component of the polypeptide's natural environment will not be present. Ordinarily, however, isolated polypeptide will be prepared by at least one purification step.

A "polypeptide chain" is a polypeptide wherein each of the domains thereof is joined to other domain(s) by peptide bond(s), as opposed to non-covalent interactions or disulfide bonds.

A polypeptide "variant" means a biologically active polypeptide having at least about 80% amino acid sequence identity with the corresponding native sequence polypeptide. Such variants include, for instance, polypeptides wherein one or more amino acid (naturally occurring amino acid and/or a non-naturally occurring amino acid) residues are added, or deleted, at the N-and/or C-terminus of the polypeptide. Ordinarily, a variant will have at least about 80% amino acid sequence identity, or at least about 90% amino acid sequence identity, or at least about 95% or more amino acid sequence identity with the native sequence polypeptide. Variants also include polypeptide fragments (e.g., subsequences, truncations, etc.), typically biologically active, of the native sequence.

The term "protein variant" as used herein refers to a variant as described above and/or a protein which includes one or more amino acid mutations in the native protein sequence. Optionally, the one or more amino acid mutations include amino acid substitution(s). Protein and variants thereof can be prepared by a variety of methods well known in the art. Amino acid sequence variants of a protein can be prepared by mutations in the protein DNA. Such variants include, for example, deletions from, insertions into or substitutions of residues within the amino acid sequence of protein. Any combination of deletion, insertion, and substitution may be made to arrive at the final construct having the desired activity. The mutations that will be made in the DNA encoding the variant must not place the sequence out of reading frame and preferably will not create complementary regions that could produce secondary mRNA structure.

The term "antibody" is used in the broadest sense and specifically covers monoclonal antibodies (including full length or intact monoclonal antibodies), polyclonal antibodies, multivalent antibodies, multispecific antibodies (e.g., bispecific antibodies) formed from at least two intact antibodies, and antibody fragments (see below) so long as they exhibit the desired biological activity.

Unless indicated otherwise, the expression "multivalent antibody" is used throughout this specification to denote an antibody comprising three or more antigen binding sites. The multivalent antibody is typically engineered to have the three or more antigen binding sites and is generally not a native sequence IgM or IgA antibody.

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., *Nature* 341, 544-546 (1989)) which consists of a VH domain; (vii) isolated CDR regions; (viii) F(ab')2 fragments, a bivalent fragment including two Fab' fragments linked by a disulphide bridge at the hinge region; (ix) single chain antibody molecules (e.g. single chain Fv; scFv) (Bird et al., *Science* 242:423-426 (1988); and Huston et al., *PNAS (USA)* 85:5879-5883 (1988)); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., *Proc. Natl. Acad. Sci. USA,* 90:6444-6448 (1993)); (xi) "linear antibodies" comprising a pair of tandem Fd segments (VH-CH1-VH-CH1) which, together with complementary light chain polypeptides, form a pair of antigen binding regions (Zapata et al. *Protein Eng.* 8(10):1057 1062 (1995); and U.S. Pat. No. 5,641,870).

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. Monoclonal antibodies are highly specific, being directed against a single antigen. In certain embodiments, a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody. In contrast to polyclonal antibody preparations that typically include different antibodies directed against different determinants (epitopes), each monoclonal antibody is directed against a single determinant on the antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. Monoclonal antibodies may be made by a variety of techniques, including, for example, the hybridoma method (e.g., Kohler and Milstein, *Nature,* 256:495-97 (1975); Hongo et al., *Hybridoma,* 14 (3): 253-260 (1995), Harlow et al., *Antibodies: A Laboratory Manual,* (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature,* 352: 624-628 (1991); Marks et al., *J. Mol. Biol.* 222: 581-597 (1991); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also, e.g., Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409. See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA*, 103:3557-3562 (2006) regarding human ant bodies gencraied via a human B-cell hybridoma technology.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art. In one embodiment, the human antibody is selected from a phage library, where that phage library expresses human antibodies (Vaughan et al. *Nature Biotechnology* 14:309-314 (1996): Sheets et al. *PNAS (USA)* 95:6157-6162 (1998)); Hoogenboom and Winter, *J. Mol. Biol.*, 227:381 (1991); Marks et al., *J. Mol. Biol.*, 222:581 (1991)). Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633, 425; 5,661,016, and in the following scientific publications: Marks et al., *Bio/Technology* 10: 779-783 (1992); Lonberg et al., *Nature* 368: 856-859 (1994); Morrison, *Nature* 368:812-13 (1994); Fishwild et al., *Nature Biotechnology* 14: 845-51 (1996); Neuberger, *Nature Biotechnology* 14: 826 (1996); Lonberg and Huszar, *Intern. Rev. Immunol.* 13:65-93 (1995). Alternatively, the human antibody may be prepared via immortalization of human B lymphocytes producing an antibody directed against a target antigen (such B lymphocytes may be recovered from an individual or may have been immunized in vitro). See, e.g., Cole et al., *Monoclonal Antibodies and Cancer Therapy*, Alan R. Liss, p. 77 (1985); Boerner et al., *J. Immunol.*, 147 (1):86-95 (1991); and U.S. Pat. No. 5,750,373.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of *Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody-dependent cellular toxicity.

The term "hypervariable region," "HVR," or "HV," when used herein refers to the amino acid residues of an antibody which are responsible for antigen-binding. For example, the term hypervariable region refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software.

The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat Numbering) |
| H1 | H31-H35 | H26-H35 | H26-H32 | H30-H35 (Chothia Numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework Region" or "FR" residues are those variable domain residues other than the hypervariable region residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

Throughout the present specification and claims, the Kabat numbering system is generally used when referring to a residue in the variable domain (approximately, residues 1-107 of the light chain and residues 1-113 of the heavy chain) (e.g., Kabat et al., *Sequences of Immunological Interest*. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., *Sequences of Proteins of Immunological Interest*, 5th Ed. Public Health Service, National Institutes of Health, Bethesda, Md. (1991) expressly incorporated herein by reference). Unless stated otherwise herein, references to residues numbers in the variable domain of antibodies means residue numbering by the Kabat numbering system. Unless stated otherwise herein, references to residue numbers in the constant domain of antibodies means residue numbering by the EU numbering system.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., $IgG_1$ (including non-A and A allotypes), $IgG_2$, $IgG_3$, $IgG_4$, $IgA_1$, and $IgA_2$. The heavy chain constant domains that correspond to the different classes of immunoglobulins are called $\alpha$, $\delta$, $\epsilon$, $\gamma$, and $\mu$, respectively. The subunit structures and three-demensional configurations of different classes of immunoglobulins are well known and described generally in, for example, Abbas et al. *Cellular and Mol. Immunology*, 4th ed. (W. B. Saunders, Co., 2000). An antibody may be part of a larger fusion molecule, formed by covalent or non-covalent association of the antibody with one or more other proteins or peptides.

The "light chains" of antibodies (immunoglobulins) from any vertebrate species can be assigned to one of two clearly distinct types, called kappa ($\kappa$) and lambda ($\lambda$), based on the amino acid sequences of their constant domains.

The term "Fc region" is used to define the C-terminal region of an immunoglobulin heavy chain which may be generated by papain digestion of an intact antibody. The Fc region may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from about position Pro230, to the carboxyl-terminus of the Fc region. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. The Fc region of an immunoglobulin generally comprises two constant domains, a CH2 domain and a CH3 domain, and optionally comprises a CH4 domain.

Unless indicated otherwise herein, the numbering of the residues in an immunoglobulin heavy chain is that of the EU index as in Kabat et al., supra. The "EU index as in Kabat" refers to the residue numbering of the human IgG1 EU antibody.

By "Fc region chain" herein is meant one of the two polypeptide chains of an Fc region.

The "CH2 domain" of a human IgG Fc region (also referred to as "Cg2" domain) usually extends from an amino acid residue at about position 231 to an amino acid residue at about position 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec. Immunol.* 22:161-206 (1985). The CH2 domain herein may be a native sequence CH2 domain or variant CH2 domain.

The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a variant CH3 domain (e.g. a CH3 domain with an introduced "protroberance" in one chain thereof and a corresponding introduced "cavity" in the other chain thereof; see U.S. Pat. No. 5,821,333, expressly incorporated herein by reference). Such variant CH3 domains may be used to make multispecific (e.g. bispecific) antibodies as herein described.

"Hinge region" is generally defined as stretching from about Glu216, or about Cys226, to about Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions. The hinge region herein may be a native sequence hinge region or a variant hinge region. The two polypeptide chains of a variant hinge region generally retain at least one cysteine residue per polypeptide chain, so that the two polypeptide chains of the variant hinge region can form a disulfide bond between the two chains. The preferred hinge region herein is a native sequence human hinge region, e.g. a native sequence human IgG1 hinge region.

A "functional Fc region" possesses at least one "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification. In certain embodiments, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide, e.g. from about one to about ten amino acid substitutions, and preferably from about one to about five amino acid substitutions in a native sequence Fc region or in the Fc region of the parent polypeptide. The variant Fc region herein will typically possess, e.g., at least about 80% sequence identity with a native sequence Fc region and/or with an Fc region of a parent polypeptide, or at least about 90% sequence identity therewith, or at least about 95% sequence or more identity therewith.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. Nos. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells and neutrophils; with PBMCs and NK cells being generally preferred. The effector cells may be isolated from a native source thereof, e.g. from blood or PBMCs as described herein.

"Fc receptor" or "FcR" describes a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (see, e.g., Daëron, *Annu. Rev. Immunol.* 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., *J. Immunol.* 117:587 (1976) and Kim et al., J. Immunol. 24:249 (1994)) and regulation of homeostasis of immunoglobulins. Methods of measuring binding to FcRn are known (see, e.g., Ghetie and Ward., *Immunol. Today* 18(12):592-598 (1997); Ghetie et al., *Nature Biotechnology,* 15(7):637-640 (1997); Hinton et al., *J. Biol. Chem.* 279(8):6213-6216 (2004); WO 2004/92219 (Hinton et al.).

Binding to human FcRn in vivo and serum half life of human FcRn high affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with improved or diminished binding to FcRs. See also, e.g., Shields et al. *J. Biol. Chem.* 9(2):6591-6604 (2001).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, e.g., as described in Gazzano-Santoro et al., *J. Immunol. Methods* 202:163 (1996), may be performed. Polypeptide variants with altered Fc region amino acid sequences (polypeptides with a variant Fc region) and increased or decreased Clq binding capability are described, e.g., in U.S. Pat. No. 6,194,551 B1 and WO 1999/51642. See also, e.g., Idusogie et al. *J. Immunol.* 164: 4178-4184 (2000).

An "affinity matured" antibody is one with one or more alterations in one or more CDRs thereof which result an improvement in the affinity of the antibody for antigen, compared to a parent antibody which does not possess those alteration(s). In one embodiment, an affinity matured antibody has nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "functional antigen binding site" of an antibody is one which is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen. Moreover, the antigen binding affinity of each of the antigen binding sites of a multivalent antibody herein need not be quantitatively the same. For the multimeric antibodies herein, the number of functional antigen binding sites can be evaluated using ultracentrifugation analysis. According to this method of analysis, different ratios of target antigen to multimeric antibody are combined and the average molecular weight of the complexes is calculated assuming differing numbers of functional binding sites. These theoretical values are compared to the actual experimental values obtained in order to evaluate the number of functional binding sites.

An antibody having a "biological characteristic" of a designated antibody is one which possesses one or more of the biological characteristics of that antibody which distinguish it from other antibodies that bind to the same antigen.

In order to screen for antibodies which bind to an epitope on an antigen bound by an antibody of interest, a routine cross-blocking assay such as that described in *Antibodies, A Laboratory Manual*, Cold Spring Harbor Laboratory, Ed Harlow and David Lane (1988), can be performed.

The term "antagonist" when used herein refers to a molecule capable of neutralizing, blocking, inhibiting, abrogating, reducing or interfering with the activities of a protein including its binding to one or more receptors in the case of a ligand or binding to one or more ligands in case of a receptor. Antagonists include antibodies and antigen-binding fragments thereof, proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. Antagonists also include small molecule inhibitors of a protein, and fusions proteins, receptor molecules and derivatives which bind specifically to protein thereby sequestering its binding to its target, antagonist variants of the protein, antisense molecules directed to a protein, RNA aptamers, and ribozymes against a protein.

A "blocking" antibody or an "antagonist" antibody is one which inhibits or reduces biological activity of the antigen it binds. Certain blocking antibodies or antagonist antibodies substantially or completely inhibit the biological activity of the antigen The term "anti-angiogenic therapy" refers to a therapy useful for inhibiting angiogenesis which comprises the administration of at least one anti-angiogenesis agent as defined herein. In another embodiment, the anti-VEGF antibody is bevacizumab.

The term "immunosuppressive agent" as used herein refers to substances that act to suppress or mask the immune system of the mammal being treated herein. This would include substances that suppress cytokine production, down-regulate or suppress self-antigen expression, or mask the MHC antigens. Examples of such agents include 2-amino-6-aryl-5-substituted pyrimidines (see U.S. Pat. No. 4,665, 077); nonsteroidal anti-inflammatory drugs (NSAIDs); ganciclovir, tacrolimus, glucocorticoids such as cortisol or aldosterone, anti-inflammatory agents such as a cyclooxygenase inhibitor, a 5-lipoxygenase inhibitor, or a leukotriene receptor antagonist; purine antagonists such as azathioprine or mycophenolate mofetil (MMF); alkylating agents such as cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as corticosteroids or glucocorticosteroids or glucocorticoid analogs, e.g., prednisone, methylprednisolone, and dexamethasone; dihydrofolate reductase inhibitors such as methotrexate (oral or subcutaneous); hydroxycloroquine; sulfasalazine; leflunomide; cytokine or cytokine receptor antibodies including anti-interferon-alpha, -beta, or -gamma antibodies, anti-tumor necrosis factor-alpha antibodies (infliximab or adalimumab), anti-TNF-alpha immunoahesin (etanercept), anti-tumor necrosis factor-beta antibodies, anti-interleukin-2 antibodies and anti-IL-2 receptor antibodies; anti-LFA-1 antibodies, including anti-CD11a and anti-CD18 antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain (WO 1990/08187 published Jul. 26, 1990); streptokinase; TGF-beta; streptodornase; RNA or DNA from the host; FK506; RS-61443; deoxyspergualin; rapamycin; T-cell receptor (Cohen et al., U.S. Pat. No. 5,114,721); T-cell-receptor fragments (Offner et al., *Science*, 251: 430-432 (1991); WO 1990/11294; Ianeway, *Nature*, 341: 482 (1989); and WO 1991/01133); and T-cell-receptor antibodies (EP 340,109) such as T10B9.

Examples of "nonsteroidal anti-inflammatory drugs" or "NSAIDs" are acetylsalicylic acid, ibuprofen, naproxen, indomethacin, sulindac, tolmetin, including salts and derivatives thereof, etc.

The term "cytotoxic agent" as used herein refers to a substance that inhibits or prevents the function of cells and/or causes destruction of cells. The term is intended to include radioactive isotopes (e.g., $^{211}$At, $^{131}$I, $^{125}$I, $^{90}$Y, $^{186}$Re, $^{188}$Re, $^{153}$Sm, $^{212}$Bi, $^{32}$P and radioactive isotopes of Lu), chemotherapeutic agents, and toxins such as small molecule toxins or enzymatically active toxins of bacterial, fungal, plant or animal origin, including fragments and/or variants thereof.

A "growth inhibitory agent" when used herein refers to a compound or composition which inhibits growth of a cell in vitro and/or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTINO®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gamma1I and calicheamicin omega1I (see, e.g., Agnew, *Chem Intl. Ed. Engl.*, 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2', 2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); lapatinib ditosylate (an ErbB-2 and EGFR dual tyrosine kinase small-molecule inhibitor also known as GW572016); COX-2 inhibitors such as celecoxib (CELEBREX®; 4-(5-(4-methylphenyl)-3-(trifluoromethyl)-1H-pyrazol-1-yl)benzenesulfonamide; and pharmaceutically acceptable salts, acids or derivatives of any of the above.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factors (e.g., VEGF, VEGF-B, VEGF-C, VEGF-D, VEGF-E); placental derived growth factor (PlGF); platelet derived growth factors (PDGF, e.g., PDGFA, PDGFB, PDGFC, PDGFD); integrin; thrombopoietin (TPO); nerve growth factors such as NGF-alpha; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta and -gamma, colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20-IL-30; secretoglobin/uteroglobin; oncostatin M (OSM); a tumor necrosis factor such as TNF-alpha or TNF-beta; and other polypeptide factors including LIF and kit ligand (KL). As used herein, the term cytokine includes proteins from natural sources or from recombinant cell culture and biologically active equivalents of the native sequence cytokines By "subject" or "patient" is meant a mammal, including, but not limited to, a human or non-human mammal, such as a bovine, equine, canine, ovine, or feline. In one embodiment, the subject is a human. In another embodiment, the subject is diagnosed with cancer.

"Mammal" for purposes of treatment refers to any animal classified as a mammal, including humans, domestic and farm animals, and zoo, sports, or pet animals, such as dogs, horses, cats, cows, sheep, pigs, etc. In one embodiment, the mammal is a human.

A "disorder" is any condition that would benefit from treatment. This includes chronic and acute disorders or diseases including those pathological conditions which predispose the mammal to the disorder in question. Non-limiting examples of disorders to be treated herein include any form of tumor, benign and malignant tumors; vascularized tumors; hypertrophy; leukemias and lymphoid malignancies; neuronal, glial, astrocytal, hypothalamic and other glandular, macrophagal, epithelial, stromal and blastocoelic disorders; and inflammatory, angiogenic and immunologic disorders, vascular disorders that result from the inappropriate, aberrant, excessive and/or pathological vascularization and/or vascular permeability.

As used herein, "treatment" (and variations such as "treat" or "treating") refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, methods and compositions are used to delay development of a disease or disorder or to slow the progression of a disease or disorder.

The term "effective amount" or "therapeutically effective amount" refers to an amount of a drug effective to treat a disease or disorder in a mammal. In the case of cancer, the effective amount of the drug may reduce the number of cancer cells; reduce the tumor size; inhibit (i.e., slow to some extent and typically stop) cancer cell infiltration into peripheral organs; inhibit (i.e., slow to some extent and typically stop) tumor metastasis; inhibit, to some extent, tumor growth, and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

To "reduce or inhibit" is to decrease or reduce an activity, function, and/or amount as compared to a reference. In certain embodiments, by "reduce or inhibit" is meant the ability to cause an overall decrease of 20% or greater. In another embodiment, by "reduce or inhibit" is meant the ability to cause an overall decrease of 50% or greater. In yet another embodiment, by "reduce or inhibit" is meant the ability to cause an overall decrease of 75%, 85%, 90%, 95%, or greater. Reduce or inhibit can refer to the symptoms of the disorder being treated, the presence or size of metastases, the size of the primary tumor, or the size or number of the blood vessels in angiogenic disorders.

Cancer (cells and/or tumors) having resistance to a therapy as used herein includes a cancer which is not responsive and/or reduced ability of producing a significant response (e.g., partial response and/or complete response) to the therapy. Resistance may be acquired resistance which arises in the course of a treatment method. In some embodiments, the acquired drug resistance is drug tolerance. Drug tolerance to a therapy includes transient and/or reversible resistance to a therapy, which is capable of regaining sensitivity to the therapy after a break in the treatment method. In some embodiments, the acquired resistance is permanent resistance. Permanent resistance to a therapy includes a genetic change conferring drug resistance.

Cancer having sensitivity to a therapy as used herein includes cancer which is responsive and/or capable of producing a significant response (e.g., partial response and/or complete response).

Methods of determining of assessing acquisition of resistance and/or maintenance of sensitivity to a therapy are known in the art. Changes in acquisition of resistance and/or maintenance of sensitivity such as drug tolerance may be assessed by assaying the growth of drug tolerant persisters. Changes in acquisition of resistance and/or maintenance of sensitivity such as permanent resistance may be assessed by assaying the growth of drug tolerant expanded persisters. In addition, changes in acquisition of resistance and/or maintenance of sensitivity may be assessed in vivo for example by assessing response to a therapy, e.g., partial response and complete response. Changes in acquisition of resistance and/or maintenance of sensitivity may be based on changes in response to a therapy in a population of individuals, e.g., number of partial responses and complete responses.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia or lymphoid malignancies. More particular examples of such cancers include kidney or renal cancer, breast cancer, colon cancer, rectal cancer, colorectal cancer, lung cancer including small-cell lung cancer, non-small cell lung cancer, adenocarcinoma of the lung and squamous carcinoma of the lung, squamous cell cancer (e.g. epithelial squamous cell cancer), cervical cancer, ovarian cancer, prostate cancer, liver cancer, bladder cancer, cancer of the peritoneum, hepatocellular cancer, gastric or stomach cancer including gastrointestinal cancer, gastrointestinal stromal tumors (GIST), pancreatic cancer, head and neck cancer, glioblastoma, retinoblastoma, astrocytoma, thecomas, arrhenoblastomas, hepatoma, hematologic malignancies including non-Hodgkins lymphoma (NHL), multiple myeloma and acute hematologic malignancies, endometrial or uterine carcinoma, endometriosis, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, melanoma, skin carcinomas, Schwannoma, oligodendroglioma, neuroblastomas, rhabdomyosarcoma, osteogenic sarcoma, leiomyosarcomas, urinary tract carcinomas, thyroid carcinomas, Wilm's tumor, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

"Tumor", as used herein, refers to all neoplastic cell growth and proliferation, whether malignant or benign, and all pre-cancerous and cancerous cells and tissues.

Examples of neoplastic disorders to be treated include, but are not limited to, those described herein under the terms "cancer" and "cancerous." Non-neoplastic conditions that are amenable to treatment with antagonists include, but are not limited to, e.g., undesired or aberrant hypertrophy, arthritis, rheumatoid arthritis (RA), psoriasis, psoriatic plaques, sarcoidosis, atherosclerosis, atherosclerotic plaques, edema from myocardial infarction, diabetic and other proliferative retinopathies including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, chronic inflammation, lung inflammation, acute lung injury/ARDS, sepsis, primary pulmonary hypertension, malignant pulmonary effusions, cerebral edema (e.g., associated with acute stroke/closed head injury/trauma), synovial inflammation, pannus formation in RA, myositis ossificans, hypertropic bone formation, osteoarthritis (OA), refractory ascites, polycystic ovarian disease, endometriosis, 3rd spacing of fluid diseases (pancreatitis, compartment syndrome, burns, bowel disease), uterine fibroids, premature labor, chronic inflammation such as IBD (Crohn's disease and ulcerative colitis), renal allograft rejection, inflammatory bowel disease, nephrotic syndrome, undesired or aberrant tissue mass growth (non-cancer), obesity, adipose tissue mass growth, hemophilic joints, hypertrophic scars, inhibition of hair growth, Osler-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), and pleural effusion.

The term "cancer therapy" refers to a therapy useful in treating cancer. The term "anti-neoplastic composition" refers to a composition useful in treating cancer comprising at least one active therapeutic agent, e.g., "anti-cancer agent." Examples of therapeutic agents (anti-cancer agents) include, but are limited to, e.g., chemotherapeutic agents, growth inhibitory agents, cytotoxic agents, agents used in radiation therapy, anti-angiogenesis agents, apoptotic agents, anti-tubulin agents, toxins, and other-agents to treat cancer, e.g., anti-VEGF neutralizing antibody, VEGF antagonist, anti-HER-2, anti-CD20, an epidermal growth factor receptor (EGFR) antagonist (e.g., a tyrosine kinase inhibitor), HER1/EGFR inhibitor, erlotinib (Tarceva®), a COX-2 inhibitor (e.g., celecoxib), interferons, cytokines, antagonists (e.g., neutralizing antibodies) that bind to one or more of the ErbB2, ErbB3, ErbB4, or VEGF receptor(s), inhibitors for receptor tyrosine kinases for platelet-derived growth factor (PDGF) and/or stem cell factor (SCF) (e.g., imatinib mesylate (Gleevec® Novartis)), TRAIL/Apo2, and other bioactive and organic chemical agents, etc, and any combinations thereof.

The term "diagnosis" is used herein to refer to the identification of a molecular or pathological state, disease or condition, such as the identification of cancer or to refer to identification of a cancer patient who may benefit from a particular treatment regimen. In one embodiment, diagnosis refers to the identification of a particular type of tumor. In yet another embodiment, diagnosis refers to the identification of a cancer cell resistant to AKT inhibitor in a subject.

The term "prognosis" is used herein to refer to the prediction of the likelihood of clinical benefit from anti-cancer therapy.

The term "prediction" is used herein to refer to the likelihood that a patient will respond either favorably or unfavorably to a particular anti-cancer therapy. In one embodiment, the prediction relates to the extent of those responses. In one embodiment, the prediction relates to whether and/or the probability that a patient will survive or improve following treatment, for example treatment with a particular therapeutic agent, and for a certain period of time without disease recurrence.

"pAKT profile" refers to the level of activation or phosphorylation of AKT ("pAKT") compared to the level of non-activated or non-phosphorylated AKT in a given sample. In one example, the sample is a tumor cell. The pAKT profile can be expressed in terms of a ratio (e.g. amount of pAKT in a tumor cell divided by amount of non-phosphorylated AKT in the cell or in a non-tumorous cell of the same type) or a subtraction (e.g. amount of pAKT in a tumor cell minus amount of non-phosphorylated AKT in the cell or in a non-tumorous cell of the same type). The pAKT profile can also be expressed in terms of the level of activation of the pathway by measuring amounts of phosphorylated downstream targets of AKT (for example, pGSK or PRAS40). A "high pAKT profile" refers to activation or phosphorylation levels of overall AKT in the sample that are higher than a baseline value. In one example, the baseline value is the basal levels of pAKT for a given cell type. In another example, the baseline value is average or mean level of pAKT in a given population of sample cells. In another example, a "high pAKT profile" refers to a tumor cell that overexpresses or has amplified phosphorylated or activated AKT in the cell, when compared to an average of normal, healthy (e.g. non-tumorous) cells of the same type from either the same mammal or a patient popluation, The pAKT profile can also be used in conjunction with other markers (for example PTEN loss, mutations to PI3K, Kras or Brafkinases, or FOXO3 localization profiles) for predicting efficacy of AKT inhibitors.

In one embodiment, the AKT or PRAS40 mutational status can also be used in coinunction with other markers (Tor example PTEN status (e.g. loss or null), mutations to PI3K, Kras or Braf kinase, or FOXO3 localization profiles) or HER2 status for predicting efficacy of AKT inhibitors or resistance of cancer cells to AKT inhibitors.

Methods of measuring levels of AKT activation and amounts of pAKT in a sample are known in the art. For example, immunoprecipitation assays can be used, such as the AKT Activity Assay Kit (available from abcam®, San Francisco, Calif.). In another example, Western blot assays can be used, such as the AKT Western Blot Assay Kit (available from Cell Signaling Technology, Danvers, Mass.). Other assay formats known for measuring pAKT levels include chemiluminescence-linked immunosorbent assays, see Cicenas, J, et. al., "Increased level of phosphorylated akt measured by chemiluminescence-linked immunosorbent assay is a predictor of poor prognosis in primary breast cancer overexpressing ErbB-2," Breast Can. Res., 7(4), R394, 2005. Other assays are available that can be used, for example the AlphaScreen SureFire Akt 1 (p-Thr30) Assay Kit (available from Perkin Elmer, Waltham, Mass.).

Methods of determining presence of PI3K mutations are known in the art. For example, assays for detection of specific mutations in the PIK3CA gene (on exons 9 and 20, and also H1047R or H1047L mutations), using real-time PCR are known (available from Qiagen, Valencia, Calif.).

Nucleic acid, may be e.g., genomic DNA, RNA transcribed from genomic DNA, or cDNA generated from RNA. Nucleic acid may be derived from a vertebrate, e.g., a mammal. A nucleic acid is said to be "derived from" a particular source if it is obtained directly from that source or if it is a copy of a nucleic acid found in that source.

Variations in nucleic acids and amino acid sequences may be detected by certain methods known to those skilled in the art. Such methods include, but are not limited to, DNA sequencing; primer extension assays, including allele-specific nucleotide incorporation assays and allele-specific primer extension assays (e.g., allele-specific PCR, allele-specific ligation chain reaction (LCR), and gap-LCR); allele-specific oligonucleotide hybridization assays (e.g., oligonucleotide ligation assays); cleavage protection assays in which protection from cleavage agents is used to detect mismatched bases in nucleic acid duplexes; analysis of MutS protein binding; electrophoretic analysis comparing the mobility of variant and wild type nucleic acid molecules; denaturing-gradient gel electrophoresis (DGGE, as in, e.g., Myers et al. (1985) Nature 313:495); analysis of RNase cleavage at mismatched base pairs; analysis of chemical or enzymatic cleavage of heteroduplex DNA; mass spectrometry (e.g., MALDI-TOF); genetic bit analysis (GBA); 5' nuclease assays (e.g., TaqMan®)); and assays employing molecular beacons. Certain of these methods are discussed in further detail below.

Detection of variations in target nucleic acids may be accomplished by molecular cloning and sequencing of the target nucleic acids using techniques well known in the art. Alternatively, amplification techniques such as the polymerase chain reaction (PCR) can be used to amplify target nucleic acid sequences directly from a genomic DNA preparation from tumor tissue. The nucleic acid sequence of the amplified sequences can then be determined and variations identified therefrom. Amplification techniques are well known in the art, e.g., polymerase chain reaction is described in Saiki et al., Science 239:487, 1988; U.S. Pat. Nos. 4,683,203 and 4,683,195.

The ligase chain reaction, which is known in the art, can also be used to amplify target nucleic acid sequences. See, e.g., Wu et al., Genomics 4:560-569 (1989). In addition, a technique known as allele-specific PCR can also be used to detect variations (e.g., substitutions). See, e.g., Ruano and Kidd (1989) Nucleic Acids Research 17:8392; McClay et al. (2002) Analytical Biochem. 301:200-206. In certain embodiments of this technique, an allele-specific primer is used wherein the 3' terminal nucleotide of the primer is complementary to (i.e., capable of specifically base-pairing with) a particular variation in the target nucleic acid. If the particular variation is not present, an amplification product is not observed. Amplification Refractory Mutation System (ARMS) can also be used to detect variations (e.g., substitutions). ARMS is described, e.g., in European Patent Application Publication No. 0332435, and in Newton et al., Nucleic Acids Research, 17:7, 1989.

Other methods useful for detecting variations (e.g., substitutions) include, but are not limited to, (1) allele-specific nucleotide incorporation assays, such as single base extension assays (see, e.g., Chen et al. (2000) Genome Res. 10:549-557; Fan et al. (2000) Genome Res. 10:853-860; Pastinen et al. (1997) Genome Res. 7:606-614; and Ye et al. (2001) Hum. Mut. 17:305-316); (2) allele-specific primer extension assays (see, e.g., Ye et al. (2001) i Hum. Mut. 17:305-316; and Shen et al. Genetic Engineering News, vol. 23, Mar. 15, 2003), including allele-specific PCR; (3) 5'nuclease assays (see, e.g., De La Vega et al. (2002) BioTechniques 32:S48-S54 (describing the TaqMan® assay); Ranade et al. (2001) Genome Res. 11:1262-1268; and Shi (2001) Clin. Chem. 47:164-172); (4) assays employing molecular beacons (see, e.g., Tyagi et al. (1998) Nature Biotech. 16:49-53; and Mhlanga et al. (2001) Methods 25:463-71); and (5) oligonucleotide ligation assays (see, e.g., Grossman et al. (1994) Nuc. Acids Res. 22:4527-4534; patent application Publication No. US 2003/0119004 A1; PCT International Publication No. WO 01/92579 A2; and U.S. Pat. No. 6,027,889).

Variations may also be detected by mismatch detection methods. Mismatches are hybridized nucleic acid duplexes which are not 100% complementary. The lack of total complementarity may be due to deletions, insertions, inversions, or substitutions. One example of a mismatch detection method is the Mismatch Repair Detection (MRD) assay described, e.g., in Faham et al., *Proc. Natl Acad. Sci. USA* 102:14717-14722 (2005) and Faham et al., *Hum. Mol. Genet.* 10:1657-1664 (2001). Another example of a mismatch cleavage technique is the RNase protection method, which is described in detail in Winter et al., *Proc. Natl. Acad. Sci. USA,* 82:7575, 1985, and Myers et al., *Science* 230: 1242, 1985. For example, a method may involve the use of a labeled riboprobe which is complementary to the human wild-type target nucleic acid. The riboprobe and target nucleic acid derived from the tissue sample are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full-length duplex RNA for the riboprobe and the mRNA or DNA. The riboprobe need not be the full length of the target nucleic acid, but can a portion of the target nucleic acid, provided it encompasses the position suspected of having a variation.

In a similar manner, DNA probes can be used to detect mismatches, for example through enzymatic or chemical cleavage. See, e.g., Cotton et al., *Proc. Natl. Acad. Sci. USA,* 85:4397, 1988; and Shenk et al., *Proc. Natl. Acad. Sci. USA,* 72:989, 1975. Alternatively, mismatches can be detected by shifts in the electrophoretic mobility of mismatched duplexes relative to matched duplexes. See, e.g., Cariello, *Human Genetics,* 42:726, 1988. With either riboprobes or DNA probes, the target nucleic acid suspected of comprising a variation may be amplified before hybridization. Changes in target nucleic acid can also be detected using Southern hybridization, especially if the changes are gross rearrangements, such as deletions and insertions.

Restriction fragment length polymorphism (RFLP) probes for the target nucleic acid or surrounding marker genes can be used to detect variations, e.g., insertions or deletions. Insertions and deletions can also be detected by cloning, sequencing and amplification of a target nucleic acid. Single stranded conformation polymorphism (SSCP) analysis can also be used to detect base change variants of an allele. See, e.g. Orita et al., *Proc. Natl. Acad. Sci. USA* 86:2766-2770, 1989, and *Genomics,* 5:874-879, 1989.

Another aspect provides arrays that can be used in such methods. In one embodiment, an array comprises individual or collections of nucleic acid molecules useful for detecting variations. For instance, an array may comprise a series of discretely placed individual allele-specific oligonucleotides or sets of allele-specific oligonucleotides. Several techniques are well-known in the art for attaching nucleic acids to a solid substrate such as a glass slide. One method is to incorporate modified bases or analogs that contain a reactive moiety that is capable of attachment to a solid substrate, such as an amine group, a derivative of an amine group, or another group with a positive charge, into nucleic acid molecules that are synthesized. The synthesized product is then contacted with a solid substrate, such as a glass slide coated with an aldehyde or other reactive group. The aldehyde or other reactive group will form a covalent link with the reactive moiety on the amplified product, which will become covalently attached to the glass slide. Other methods, such as those using amino propryl silican surface chemistry are also known in the art.

A biological sample, according to any of the above methods, may be obtained using certain methods known to those skilled in the art. Biological samples may be obtained from vertebrate animals, and in particular, mammals. Tissue biopsy is often used to obtain a representative piece of tumor tissue. Alternatively, tumor cells can be obtained indirectly in the form of tissues or fluids that are known or thought to contain the tumor cells of interest. For instance, samples of lung cancer lesions may be obtained by resection, bronchoscopy, fine needle aspiration, bronchial brushings, or from sputum, pleural fluid or blood. Variations in target nucleic acids (or encoded polypeptides) may be detected from a tumor sample or from other body samples such as urine, sputum or serum. (Cancer cells are sloughed off from tumors and appear in such body samples.) By screening such body samples, a simple early diagnosis can be achieved for diseases such as cancer. In addition, the progress of therapy can be monitored more easily by testing such body samples for variations in target nucleic acids (or encoded polypeptides). Additionally, methods for enriching a tissue preparation for tumor cells are known in the art. For example, the tissue may be isolated from paraffin or cryostat sections. Cancer cells may also be separated from normal cells by flow cytometry or laser capture microdissection.

AKT Kinase Inhibitors

Certain AKT kinase inhibitors are known as ATP-competitive inhibitors, for their ability to compete with ATP for binding to the active site of AKT. Certain AKT kinase inhibitors known as allosteric inhibitors do not bind to the active site of AKT. Also, AKT kinase inhibitors can be pan-AKT inhibitors, wherein the inhibitor can inhibit the activity of two or more of AKT-1, AKT-2 and AKT-3. AKT kinase inhibitors can be selective AKT inhibitors, wherein the inhibitor can inhibit the activity of one of AKT-1, AKT-2 and AKT-3, without inhibiting the activity of the other two.

In one embodiment, the AKT kinase inhibitor is an ATP-competitive inhibitor. In another embodiment, the ATP-competitive inhibitor is a pan-AKT inhibitor. For example, in certain embodiments, the AKT inhibitor is an ATP-competitive, pan-AKT inhibitor of Formula I:

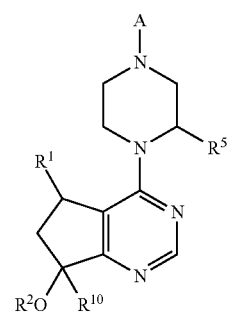

and tautomers, resolved enantiomers, resolved diastereomers, solvates, and salts thereof, wherein, $R^1$ is H, Me, Et and $CF_3$;

$R^2$ is H or Me; $R^5$ is H or Me;

A is:

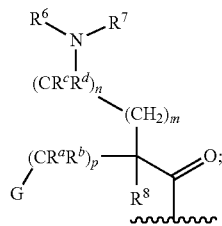

wherein G is phenyl optionally substituted by one to four $R^9$ groups or a 5-6 membered heteroaryl optionally substituted by a halogen;

$R^6$ and $R^7$ are independently H, $OCH_3$, $(C_3-C_6$ cycloalkyl)-$(CH_2)$, $(C_3-C_6$ cycloalkyl)-$(CH_2CH_2)$, V—$(CH_2)_{0-1}$ wherein V is a 5-6 membered heteroaryl, W—$(CH_2)_{1-2}$ wherein W is phenyl optionally substituted with F, Cl, Br, I, OMe, $CF_3$ or Me, $C_3-C_6$-cycloalkyl optionally substituted with $C_1-C_3$ alkyl or O ($C_1-C_3$ alkyl), hydroxy-($C_3-C_6$-cycloalkyl), fluoro-($C_3-C_6$-cycloalkyl), $CH(CH_3)CH(OH)$phenyl, 4-6 membered heterocycle optionally substituted with F, OH, $C_1-C_3$ alkyl, cyclopropylmethyl or C(=O)($C_1-C_3$ alkyl), or $C_1-C_6$-alkyl optionally substituted with one or more groups independently selected from OH, oxo, O($C_1-C_6$-alkyl), CN, F, $NH_2$, NH($C_1-C_6$-alkyl), N($C_1-C_6$-alkyl)$_2$, cyclopropyl, phenyl, imidazolyl, piperidinyl, pyrrolidinyl, morpholinyl, tetrahydrofuranyl, oxetanyl or tetrahydropyranyl, or $R^6$ and $R^7$ together with the nitrogen to which they are attached form a 4-7 membered heterocyclic ring optionally substituted with one or more groups independently selected from OH, halogen, oxo, $CF_3$, $CH_2CF_3$, $CH_2CH_2OH$, O($C_1-C_3$ alkyl), C(=O)$CH_3$, $NH_2$, NHMe, N(Me)$_2$, S(O)$_2CH_3$, cyclopropylmethyl and $C_1-C_3$ alkyl;

$R^a$ and $R^b$ are H, or $R^a$ is H, and $R^b$ and $R^6$ together with the atoms to which they are attached form a 5-6 membered heterocyclic ring having one or two ring nitrogen atoms;

$R^c$ and $R^d$ are H or Me, or $R^c$ and $R^d$ together with the atom to which they are attached from a cyclopropyl ring;

$R^8$ is H, Me, F or OH, or $R^8$ and $R^6$ together with the atoms to which they are attached form a 5-6 membered heterocyclic ring having one or two ring nitrogen atoms;

each $R^9$ is independently halogen, $C_1-C_6$-alkyl, $C_3-C_6$-cycloalkyl, O—($C_1-C_6$-alkyl), $CF_3$, $OCF_3$, S($C_1-C_6$-alkyl), CN, $OCH_2$-phenyl, $CH_2O$-phenyl, $NH_2$, NH—($C_1-C_6$-alkyl), N—($C_1-C_6$-alkyl)$_2$, piperidine, pyrrolidine, $CH_2F$, $CHF_2$, $OCH_2F$, $OCHF_2$, OH, $SO_2$($C_1-C_6$-alkyl), C(O)$NH_2$, C(O)NH($C_1-C_6$-alkyl), and C(O)N($C_1-C_6$-alkyl)$_2$;

$R^{10}$ is H or Me; and m, n and p are independently 0 or 1.

Another embodiment includes AKT inhibitors of Formula I, wherein $R^1$ is methyl; $R^2$, $R^5$ and $R^{10}$ are H; G is phenyl optionally substituted with 1-3 $R^9$; $R^9$ is halogen, $C_1-C_3$ alkyl, CN, $CF_3$, $OCF_3$ $OCH_3$ or $OCH_2$Phenyl; $R_c$ and $R_d$ are H or methyl; m, n and p are 0 or 1; and $R^8$ is H or methyl.

Another embodiment includes AKT inhibitors of Formula I, selected from:

2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one dihydrochloride;

(R)-2-amino-3-(4-chlorophenyl)-1-((S)-4-((5R,7R)-7-hydroxy-5-methyl-6,7-dihydro-5H-cyclopenta[d]pyrimidin-4-yl)-3-methylpiperazin-1-yl)propan-1-one dihydrochloride;

(R)-2-amino-3-(4-chloro-3-fluorophenyl)-1-((S)-4-((5R,7R)-7-hydroxy-5-methyl-6,7-dihydro-5H-cyclopenta[d]pyrimidin-4-yl)-3-methylpiperazin-1-yl)propan-1-one dihydrochloride;

(R)-2-amino-3-(4-chloro-3-fluorophenyl)-1-((S)-4-((5R,7R)-7-methoxy-5-methyl-6,7-dihydro-5H-cyclopenta[d]pyrimidin-4-yl)-3-methylpiperazin-1-yl)propan-1-one dihydrochloride;

(S)-3-amino-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one dihydrochloride;

(R)-2-amino-3-(4-chlorophenyl)-1-((S)-4-((S)-7-hydroxy-6,7-dihydro-5H-cyclopenta[d]pyrimidin-4-yl)-3-methylpiperazin-1-yl)propan-1-one;

(R)-2-amino-3-(4-chloro-3-fluorophenyl)-1-((S)-4-((S)-7-hydroxy-6,7-dihydro-5H-cyclopenta[d]pyrimidin-4-yl)-3-methylpiperazin-1-yl)propan-1-one;

(2R)-2-amino-3-(4-chloro-3-fluorophenyl)-1-((3S)-4-((5R)-7-hydroxy-5-methyl-6,7-dihydro-5H-cyclopenta[d]pyrimidin-4-yl)-3-methylpiperazin-1-yl)propan-1-one;

(2R)-2-amino-3-(4-chlorophenyl)-1-(4-(7-hydroxy-6,7-dihydro-5H-cyclopenta[d]pyrimidin-4-yl)piperazin-1-yl)propan-1-one;

(R)-2-amino-1-(4-((5R,7R)-7-hydroxy-5-methyl-6,7-dihydro-5H-cyclopenta[d]pyrimidin-4-yl)piperazin-1-yl)-3-(4-methoxyphenyl)propan-1-one;

2-(4-chlorophenyl)-1-((S)-4-((R)-7-hydroxy-6,7-dihydro-5H-cyclopenta[d]pyrimidin-4-yl)-3-methylpiperazin-1-yl)-3-(isopropylamino)prop an-1-one;

2-(4-chlorophenyl)-1-(4-(7-hydroxy-6,7-dihydro-5H-cyclopenta[d]pyrimidin-4-yl)piperazin-1-yl)-3-(isopropylamino)propan-1-one dihydrochloride;

2-(4-chlorophenyl)-3-(isopropylamino)-1-(4-(7-methoxy-6,7-dihydro-5H-cyclopenta[d]pyrimidin-4-yl)piperazin-1-yl)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

2-(4-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

2-(3,4-difluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

2-(4-chlorophenyl)-1-(4-((5R,7R)-7-hydroxy-5-methyl-6,7-dihydro-5H-cyclopenta[d]pyrimidin-4-yl)piperazin-1-yl)-3-(pyridin-3-ylmethylamino)propan-1-one;

2-(2,4-dichlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

2-(4-chlorophenyl)-1-(4-((5R,7R)-7-hydroxy-5-methyl-6,7-dihydro-5H-cyclopenta[d]pyrimidin-4-yl)piperazin-1-yl)-3-(pentan-3-ylamino)propan-1-one;

2-(4-chlorophenyl)-3-((1S,2R)-1-hydroxy-1-phenylpropan-2-ylamino)-1-(4-((5R,7R)-7-hydroxy-5-methyl-6,7-dihydro-5H-cyclopenta[d]pyrimidin-4-yl)piperazin-1-yl)propan-1-one;

2-(4-chlorophenyl)-1-(4-((5R,7R)-7-hydroxy-5-methyl-6,7-dihydro-5H-cyclopenta[d]pyrimidin-4-yl)piperazin-1-yl)-3-((1R,4R)-4-hydroxycyclohexylamino)propan-1-one;

((3S,4R)-4-(3,4-dichlorophenyl)pyrrolidin-3-yl)(4-45R,7R)-7-hydroxy-5-methyl-6,7-dihydro-5H-cyclopenta[d]pyrimidin-4-yl)piperazin-1-yl)methanone;

((3R,4S)-4-(3,4-dichlorophenyl)pyrrolidin-3-yl)(4-45R,7R)-7-hydroxy-5-methyl-6,7-dihydro-5H-cyclopenta[d]pyrimidin-4-yl)piperazin-1-yl)methanone;

2-(4-chlorophenyl)-2-hydroxy-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

4-amino-2-(4-chlorophenyl)-1-(4-((5R,7R)-7-hydroxy-5-methyl-6,7-dihydro-5H-cyclopenta[d]pyrimidin-4-yl)piperazin-1-yl)-4-methylpentan-1-one;

4-amino-2-(3,4-difluorophenyl)-1-(4-((5R,7R)-7-hydroxy-5-methyl-6,7-dihydro-5H-cyclopenta[d]pyrimidin-4-yl)piperazin-1-yl)-4-methylpentan-1-one;

(4-(4-chloro-3-fluorophenyl)piperidin-4-yl)(4-(5R,7R)-7-hydroxy-5-methyl-6,7-dihydro-5H-cyclopenta[d]pyrimidin-4-yl)piperazin-1-yl)methanone;

(3-(4-chlorophenyl)pyrrolidin-3-yl)(4-(5R,7R)-7-hydroxy-5-methyl-6,7-dihydro-5H-cyclopenta[d]pyrimidin-4-yl)piperazin-1-yl)methanone;

1-(4-((5R,7R)-7-hydroxy-5-methyl-6,7-dihydro-5H-cyclopenta[d]pyrimidin-4-yl)piperazin-1-yl)-3-(isopropylamino)-2-p-tolylpropan-1-one;

1-(4-((5R,7R)-7-hydroxy-5-methyl-6,7-dihydro-5H-cyclopenta[d]pyrimidin-4-yl)piperazin-1-yl)-3-(isopropylamino)-2-(4-methoxyphenyl)propan-1-one;

3-(ethylamino)-2-(4-fluorophenyl)-1-(4-((5R,7R)-7-hydroxy-5-methyl-6,7-dihydro-5H-cyclopenta[d]pyrimidin-4-yl)piperazin-1-yl)propan-1-one;

2-(4-fluorophenyl)-1-(4-((5R,7R)-7-hydroxy-5-methyl-6,7-dihydro-5H-cyclopenta[d]pyrimidin-4-yl)piperazin-1-yl)-3-(methylamino)propan-1-one;

(S)-3-amino-2-(3,4-dichlorophenyl)-1-(4-((5R,7R)-7-hydroxy-5-methyl-6,7-dihydro-5H-cyclopenta[d]pyrimidin-4-yl)piperazin-1-yl)propan-1-one;

2-(4-chlorophenyl)-3-(cyclopropylmethylamino)-1-(4-((5R,7R)-7-hydroxy-5-methyl-6,7-dihydro-5H-cyclopenta[d]pyrimidin-4-yl)piperazin-1-yl)propan-1-one;

2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

2-(4-chlorophenyl)-1-(4-((5R,7R)-7-hydroxy-5-methyl-6,7-dihydro-5H-cyclopenta[d]pyrimidin-4-yl)piperazin-1-yl)-3-(pyrrolidin-1-yl)propan-1-one;

(R)-2-amino-3-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

2-(4-chlorophenyl)-1-((S)-4-((S)-7-hydroxy-6,7-dihydro-5H-cyclopenta[d]pyrimidin-4-yl)-3-methylpiperazin-1-yl)-3-(isopropylamino)propan-1-one;

(R)-2-amino-3-(4-chlorophenyl)-1-((S)-4-((R)-7-hydroxy-6,7-dihydro-5H-cyclopenta[d]pyrimidin-4-yl)-3-methylpiperazin-1-yl)propan-1-one;

(R)-2-amino-3-(4-chloro-3-fluorophenyl)-1-((S)-4-((R)-7-hydroxy-6,7-dihydro-5H-cyclopenta[d]pyrimidin-4-yl)-3-methylpiperazin-1-yl)propan-1-one;

2-(4-chlorophenyl)-1-(4-((5R)-7-hydroxy-5,7-dimethyl-6,7-dihydro-5H-cyclopenta[d]pyrimidin-4-yl)piperazin-1-yl)-3-(isopropylamino)propan-1-one;

(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(4-(3,4-dichlorophenyl)piperidin-4-yl)(4((5R,7R)-7-hydroxy-5-methyl-6,7-dihydro-5H-cyclopenta[d]pyrimidin-4-yl)piperazin-1-yl)methanone dihydrochloride;

4-(3,4-dichlorophenyl)pyrrolidin-3-yl)(4((5R,7R)-7-hydroxy-5-methyl-6,7-dihydro-5H-cyclopenta[d]pyrimidin-4-yl)piperazin-1-yl)methanone dihydrochloride;

1-(4-((5R,7R)-7-hydroxy-5-methyl-6,7-dihydro-5H-cyclopenta[d]pyrimidin-4-yl)piperazin-1-yl)-2-(4-methoxyphenyl)-3-(pyrrolidin-1-yl)propan-1-one;

2-(4-chlorophenyl)-1-(4-((5R,7R)-7-hydroxy-5-methyl-6,7-dihydro-5H-cyclopenta[d]pyrimidin-4-yl)piperazin-1-yl)-3-(2,2,2-trifluoroethylamino)propan-1-one;

3-(tert-butylamino)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(methyl(tetrahydro-2H-pyran-4-yl)amino)propan-1-one;

(S)-2-(4-chlorophenyl)-3-(cyclopropylmethylamino)-1-(4-((5R,7S)-7-hydroxy-5-methyl-6,7-dihydro-5H-cyclopenta[d]pyrimidin-4-yl)piperazin-1-yl)propan-1-one;

(S)-2-(5-chlorothiophen-2-yl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(R)-2-amino-3-(4-chlorophenyl)-1-(4-((5R,7S)-7-hydroxy-5-methyl-6,7-dihydro-5H-cyclopenta[d]pyrimidin-4-yl)piperazin-1-yl)propan-1-one;

1-(4-((5R,7R)-7-hydroxy-5-methyl-6,7-dihydro-5H-cyclopenta[d]pyrimidin-4-yl)piperazin-1-yl)-3-(isopropylamino)-2-(4-(trifluoromethyl)phenyl)propan-1-one;

4-(1-(4-((5R,7R)-7-hydroxy-5-methyl-6,7-dihydro-5H-cycloenta[d]pyrimidin-4-yl)piperazin-1-yl)-3-(isopropylamino)-1-oxopropan-2-yl)benzonitrile;

(S)-2-(4-chlorophenyl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one;

3-(azetidin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

2-(4-chlorophenyl)-1-(4-((5R,7R)-7-hydroxy-5-methyl-6,7-dihydro-5H-cyclopenta[d]pyrimidin-4-yl)piperazin-1-yl)-3-(3-hydroxyazetidin-1-yl)propan-1-one;

2-(4-chlorophenyl)-1-(4-((5R,7R)-7-hydroxy-5-methyl-6,7-dihydro-5H-cyclopenta[d]pyrimidin-4-yl)piperazin-1-yl)-3-(neopentylamino)propan-1-one;

2-(4-bromophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

2-(4-chlorophenyl)-3-(4-fluoropiperidin-1-yl)-1-(4-((5R,7R)-7-hydroxy-5-methyl-6,7-dihydro-5H-cyclopenta[d]pyrimidin-4-yl)piperazin-1-yl)propan-1-one;

2-(4-chlorophenyl)-3-((S)-3-fluoropyrrolidin-1-yl)-1-(4-((5R,7R)-7-hydroxy-5-methyl-6,7-dihydro-5H-cyclopenta[d]pyrimidin-4-yl)piperazin-1-yl)propan-1-one;

2-(4-chlorophenyl)-3-(ethylamino)-1-(4-((5R,7R)-7-hydroxy-5-methyl-6,7-dihydro-5H-cyclopenta[d]pyrimidin-4-yl)piperazin-1-yl)propan-1-one;

2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropyl(methyl)amino)propan-1-one;

2-(4-chlorophenyl)-3-(4,4-difluoropiperidin-1-yl)-1-(4-((5R,7R)-7-hydroxy-5-methyl-6,7-dihydro-5H-cyclopenta[d]pyrimidin-4-yl)piperazin-1-yl)propan-1-one;

2-(4-chlorophenyl)-3-(3,3-difluoropyrrolidin-1-yl)-1-(4-((5R,7R)-7-hydroxy-5-methyl-6,7-dihydro-5H-cyclopenta[d]pyrimidin-4-yl)piperazin-1-yl)propan-1-one;

2-(4-bromo-3-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(R)-2-amino-3-(4-fluorophenyl)-1-(4-((5R,7S)-7-hydroxy-5-methyl-6,7-dihydro-5H-cyclopenta[d]pyrimidin-4-yl)piperazin-1-yl)propan-1-one;

(R)-2-amino-3-(3,4-dichlorophenyl)-1-(4-((5R,7S)-7-hydroxy-5-methyl-6,7-dihydro-5H-cyclopenta[d]pyrimidin-4-yl)piperazin-1-yl)propan-1-one;

(R)-2-amino-3-(3,4-difluorophenyl)-1-(4-((5R,7S)-7-hydroxy-5-methyl-6,7-dihydro-5H-cyclopenta[d]pyrimidin-4-yl)piperazin-1-yl)propan-1-one;

(R)-2-(4-chlorophenyl)-3-(cyclopropylmethylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chlorophenyl)-3-(cyclopropylmethylamino)-1-(4-((5R,7R)-7-hydroxy-5-methyl-6,7-dihydro-5H-cyclopenta[d]pyrimidin-4-yl)piperazin-1-yl)propan-1-one;

2-(4-chlorophenyl)-3-((R)-3-fluoropyrrolidin-1-yl)-1-(4-((5R,7R)-7-hydroxy-5-methyl-6,7-dihydro-5H-cyclopenta[d]pyrimidin-4-yl)piperazin-1-yl)propan-1-one;

(S)-1-(4-((5R,7R)-7-hydroxy-5-methyl-6,7-dihydro-5H-cyclopenta[d]pyrimidin-4-yl)piperazin-1-yl)-3-(isopropylamino)-2-(4-(trifluoromethoxy)phenyl)propan-1-one;

(S)-2-(4-chlorophenyl)-3-(cyclopropylamino)-1-(4-((5R,7R)-7-hydroxy-5-methyl-6,7-dihydro-5H-cyclopenta[d]pyrimidin-4-yl)piperazin-1-yl)propan-1-one;

(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(3-hydroxyazetidin-1-yl)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(3-hydroxyazetidin-1-yl)propan-1-one;

(R)-4-amino-2-(4-chlorophenyl)-1-(4-((5R,7R)-7-hydroxy-5-methyl-6,7-dihydro-5H-cyclopenta[d]pyrimidin-4-yl)piperazin-1-yl)-4-methylpentan-1-one;

(S)-4-amino-2-(4-chlorophenyl)-1-(4-((5R,7R)-7-hydroxy-5-methyl-6,7-dihydro-5H-cyclopenta[d]pyrimidin-4-yl)piperazin-1-yl)-4-methylpentan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-((R)-pyrrolidin-3-ylamino)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-((S)-pyrrolidin-3-ylamino)propan-1-one;

(S)-3-((R)-1-acetylpyrrolidin-3-ylamino)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

(S)-3-((S)-1-acetylpyrrolidin-3-ylamino)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

(S)-2-(4-bromophenyl)-3-(cyclopropylmethylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(piperidin-4-ylamino)propan-1-one;

(S)-3-(1-acetylpiperidin-4-ylamino)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(2-methoxyethylamino)propan-1-one;

(R)-2-(4-chlorophenyl)-4-(dimethylamino)-1-(4-((5R,7R)-7-hydroxy-5-methyl-6,7-dihydro-5H-cyclopenta[d]pyrimidin-4-yl)piperazin-1-yl)butan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-((1r,4S)-4-hydroxycyclohexylamino)propan-1-one;

(S)-3-(azetidin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

(R)-3-(azetidin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

2-((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropylamino)acetamide;

2-((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropylamino)-N,N-dimethylacetamide;

2-((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropylamino)-N-methylacetamide;

(R)-2-(4-bromophenyl)-1-(4-((5R,7R)-7-hydroxy-5-methyl-6,7-dihydro-5H-cyclopenta[d]pyrimidin-4-yl)piperazin-1-yl)-4-(isopropylamino)butan-1-one;

(R)-2-(4-bromophenyl)-4-(dimethylamino)-1-(4-((5R,7R)-7-hydroxy-5-methyl-6,7-dihydro5H-cyclopenta[d]pyrimidin-4-yl)piperazin-1-yl)butan-1-one;

(R)-2-(4-bromophenyl)-1-(4-((5R,7R)-7-hydroxy-5-methyl-6,7-dihydro-5H-cyclopenta[d]pyrimidin-4-yl)piperazin-1-yl)-4-(isobutylamino)butan-1-one;

(R)-2-(4-chlorophenyl)-1-(4-((5R,7R)-7-hydroxy-5-methyl-6,7-dihydro-5H-cyclopenta[d]pyrimidin-4-yl)piperazin-1-yl)-4-((2-methoxyethyl)(methyl)amino)butan-1-one;

(R)-2-(4-chlorophenyl)-1-(4-((5R,7R)-7-hydroxy-5-methyl-6,7-dihydro-5H-cyclopenta[d]pyrimidin-4-yl)piperazin-1-yl)-4-(isopropylamino)butan-1-one;

(R)-2-(4-chlorophenyl)-1-(4-((5R,7R)-7-hydroxy-5-methyl-6,7-dihydro-5H-cyclopenta[d]pyrimidin-4-yl)piperazin-1-yl)-4-(3-hydroxyazetidin-1-yl)butan-1-one;

2-((R)-3-(4-bromophenyl)-4-(4-((5R,7R)-7-hydroxy-5-methyl-6,7-dihydro-5H-cyclopenta[d]pyrimidin-4-yl)piperazin-1-yl)-4-oxobutylamino)-N,N-dimethylacetamide;

(R)-2-(4-bromophenyl)-1-(4-((5R,7R)-7-hydroxy-5-methyl-6,7-dihydro-5H-cyclopenta[d]pyrimidin-4-yl)piperazin-1-yl)-4-(2-hydroxyethylamino)butan-1-one;

(2R)-2-(4-bromophenyl)-4-(2-hydroxy-1-(tetrahydro-2H-pyran-4-yl)ethylamino)-1-(4-((5R,7R)-7-hydroxy-5-methyl-6,7-dihydro-5H-cyclopenta[d]pyrimidin-4-yl)piperazin-1-yl)butan-1-one;

(R)-2-amino-1-(4-((5R,7R)-7-hydroxy-5-methyl-6,7-dihydro-5H-cyclopenta[d]pyrimidin-4-yl)piperazin-1-yl)-3-(4-iodophenyl)propan-1-one;

4-((R)-2-amino-3-(4-((5R,7R)-7-hydroxy-5-methyl-6,7-dihydro-5H-cyclopenta[d]pyrimidin-4-yl)piperazin-1-yl)-3-oxopropyl)benzonitrile;

(R)-2-amino-1-(4-((5R,7R)-7-hydroxy-5-methyl-6,7-dihydro-5H-cyclopenta[d]pyrimidin-4-yl)piperazin-1-yl)-3-(4-(trifluoromethyl)phenyl)propan-1-one;

(S)-3-(4-acetylpiperazin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

(R)-3-(4-acetylpiperazin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

(R)-3-(4-chlorophenyl)-1-(4-((5R,7R)-7-hydroxy-5-methyl-6,7-dihydro-5H-cyclopenta[d]pyrimidin-4-yl)piperazin-1-yl)-2-(methylamino)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-(2-hydroxyethyl)piperazin-1-yl)propan-1-one;

(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-(2-hydroxyethyl)piperazin-1-yl)propan-1-one;

2-(4-chlorophenyl)-1-(4-((5R,7R)-7-hydroxy-5-methyl-6,7-dihydro-5H-cyclopenta[d]pyrimidin-4-yl)piperazin-1-yl)-3-(3-methoxyazetidin-1-yl)propan-1-one;

(R)-2-(4-chlorophenyl)-4-(cyclohexylamino)-1-(4-((5R,7R)-7-hydroxy-5-methyl-6,7-dihydro-5H-cyclopenta[d]pyrimidin-4-yl)piperazin-1-yl)butan-1-one;

(R)-2-(4-chlorophenyl)-1-(4-((5R,7R)-7-hydroxy-5-methyl-6,7-dihydro-5H-cyclopenta[d]pyrimidin-4-yl)piperazin-1-yl)-4-(tetrahydro-2H-pyran-4-ylamino)butan-1-one;

(2R)-2-(4-chlorophenyl)-1-(4-((5R,7R)-7-hydroxy-5-methyl-6,7-dihydro-5H-cyclopenta[d]pyrimidin-4-yl)piperazin-1-yl)-4-(2-hydroxypropylamino)butan-1-one;

(2R)-2-(4-chlorophenyl)-4-(2-hydroxy-1-(tetrahydro-2H-pyran-4-yl)ethylamino)-1-(4-((5R,7R)-7-hydroxy-5-methyl-6,7-dihydro-5H-cyclopenta[d]pyrimidin-4-yl)piperazin-1-yl)butan-1-one;

(2R)-2-(4-chlorophenyl)-4-(2-hydroxy-1-phenylethylamino)-1-(4-((5R,7R)-7-hydroxy-5-methyl-6,7-dihydro-5H-cyclopenta[d]pyrimidin-4-yl)piperazin-1-yl)butan-1-one;

(S)-2-(4-chlorophenyl)-3-(ethyl(tetrahydro-2H-pyran-4-yl)amino)-1-(4-((5R,7R)-7-hydroxy-5-methyl-6,7-dihydro-5H-cyclopenta[d]pyrimidin-4-yl)piperazin-1-yl)propan-1-one;

(R)-2-(4-bromophenyl)-1-(4-((5R,7R)-7-hydroxy-5-methyl-6,7-dihydro-5H-cyclopenta[d]pyrimidin-4-yl)piperazin-1-yl)-4-(2-methoxyethylamino)butan-1-one;

(2R)-2-(4-bromophenyl)-1-(4-((5R,7R)-7-hydroxy-5-methyl-6,7-dihydro-5H-cyclopenta[d]pyrimidin-4-yl)piperazin-1-yl)-4-(3,3,3-trifluoro-2-hydroxypropylamino)butan-1-one;

(R)-2-(4-bromophenyl)-1-(4-((5R,7R)-7-hydroxy-5-methyl-6,7-dihydro-5H-cyclopenta[d]pyrimidin-4-yl)piperazin-1-yl)-4-((1-hydroxycycloprop yl)methylamino)butan-1-one;

2-((R)-3-(4-bromophenyl)-4-(4-((5R,7R)-7-hydroxy-5-methyl-6,7-dihydro-5H-cyclopenta[d]pyrimidin-4-yl)piperazin-1-yl)-4-oxobutylamino)acetamide;

(R)-2-(4-bromophenyl)-1-(4-((5R,7R)-7-hydroxy-5-methyl-6,7-dihydro-5H-cyclopenta[d]pyrimidin-4-yl)piperazin-1-yl)-4-(tetrahydro-2H-pyran-4-ylamino)butan-1-one;

(R)-4-(3-(1H-imidazol-1-yl)propylamino)-2-(4-bromophenyl)-1-(4-((5R,7R)-7-hydroxy-5-methyl-6,7-dihydro-5H-cyclopenta[d]pyrimidin-4-yl)piperazin-1-yl)butan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-morpholinopropan-1-one;

(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-morpholinopropan-1-one;

(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-methylpiperazin-1-yl)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-methylpiperazin-1-yl)propan-1-one;

(S)-3-(3-aminoazetidin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

(R)-3-(3-aminoazetidin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-thiomorpholinopropan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(piperazin-1-yl)propan-1-one;

(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(piperazin-1-yl)propan-1-one;

(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-thiomorpholinopropan-1-one;

(R)-2-(4-chlorophenyl)-3-(4-fluoropiperidin-1-yl)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chlorophenyl)-3-(4-fluoropiperidin-1-yl)-1-(4-((5R,7R)-7-hydroxy-5-methyl-6,7-dihydro-5H-cyclopenta[d]pyrimidin-4-yl)piperazin-1-yl)propan-1-one;

(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(3-methoxyazetidin-1-yl)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(3-methoxyazetidin-1-yl)propan-1-one;

(S)-2-(3,4-dichlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(4-chlorophenyl)-3-(dimethylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-fluoro-3-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(methoxyamino)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-methoxypiperidin-1-yl)propan-1-one;

(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-methoxypiperidin-1-yl)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one;

(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one;

(S)-3-(4-aminopiperidin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

(R)-3-(4-aminopiperidin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chlorophenyl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(4-chlorophenyl)-1-(4-((5R,7S)-7-hydroxy-5-methyl-6,7-dihydro-5H-cyclopenta[d]pyrimidin-4-yl)piperazin-1-yl)-3-(methyl(tetrahydro-2H-pyran-4-yl)amino)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropyl(methyl)amino)propan-1-one;
(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-(methylsulfonyl)piperazin-1-yl)propan-1-one;
(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-(methylamino)piperidin-1-yl)propan-1-one;
(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-(methylamino)piperidin-1-yl)propan-1-one;
(S)-2-(4-chloro-3-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;
(S)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;
(S)-2-(4-chloro-3-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;
(R)-2-(4-chlorophenyl)-3-(4-ethylpiperazin-1-yl)-1-(4-((5R,7R)-7-hydroxy-5-methyl-6,7-dihydro-5H-cyclopenta[d]pyrimidin-4-yl)piperazin-1-yl)propan-1-one;
(S)-2-(4-chlorophenyl)-3-(4-ethylpiperazin-1-yl)-1-(4-((5R,7R)-7-hydroxy-5-methyl-6,7-dihydro-5H-cyclopenta[d]pyrimidin-4-yl)piperazin-1-yl)propan-1-one;
(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-isopropylpiperazin-1-yl)propan-1-one;
(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-isopropylpiperazin-1-yl)propan-1-one;
(R)-2-(4-chlorophenyl)-3-((S)-3-(dimethylamino)pyrrolidin-1-yl)-1-(4-((5R,7R)-7-hydroxy-5-methyl-6,7-dihydro-5H-cyclopenta[d]pyrimidin-4-yl)piperazin-1-yl)propan-1-one;
(S)-2-(4-chlorophenyl)-3-((S)-3-(dimethylamino)pyrrolidin-1-yl)-1-(4-((5R,7R)-7-hydroxy-5-methyl-6,7-dihydro-5H-cyclopenta[d]pyrimidin-4-yl)piperazin-1-yl)propan-1-one;
(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-((R)-tetrahydrofuran-3-ylamino)propan-1-one;
(S)-2-(4-chlorophenyl)-1-(4-((5R,7S)-7-hydroxy-5-methyl-6,7-dihydro-5H-cyclopenta[d]pyrimidin-4-yl)piperazin-1-yl)-3-((R)-tetrahydrofuran-3-ylamino)propan-1-one;
(S)-2-(4-chlorophenyl)-3-(2-fluoroethylamino)-1-(4-((5R,7R)-7-hydroxy-5-methyl-6,7-dihydro-5H-cyclopenta[d]pyrimidin-4-yl)piperazin-1-yl)propan-1-one;
(S)-2-(4-fluoro-3-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;
(S)-2-(3,5-bis(trifluoromethyl)phenyl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one;
(S)-2-(3-fluoro-4-methoxyphenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;
4-((R)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)piperazin-2-one;
(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-((R)-3-hydroxypyrrolidin-1-yl)propan-1-one;
(S)-2-(4-chlorophenyl)-3-(4-(dimethylamino)piperidin-1-yl)-1-(4-((5R,7R)-7-hydroxy-5-methyl-6,7-dihydro-5H-cyclopenta[d]pyrimidin-4-yl)piperazin-1-yl)propan-1-one;
(R)-2-(4-chlorophenyl)-3-(4-(dimethylamino)piperidin-1-yl)-1-(4-((5R,7R)-7-hydroxy-5-methyl-6,7-dihydro-5H-cyclopenta[d]pyrimidin-4-yl)piperazin-1-yl)propan-1-one;
(S)-2-(3-chloro-5-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;
(S)-2-(3-bromo-4-methoxyphenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;
(R)-3-(4-chlorophenyl)-1-(4-((5R,7R)-7-hydroxy-5-methyl-6,7-dihydro-5H-cyclopenta[d]pyrimidin-4-yl)piperazin-1-yl)-2-(piperidin-4-ylamino)propan-1-one;
(R)-2-(1-acetylpiperidin-4-ylamino)-3-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;
2-((R)-3-(4-chlorophenyl)-1-(4-((5R,7R)-7-hydroxy-5-methyl-6,7-dihydro-5H-cyclopenta[d]pyrimidin-4-yl)piperazin-1-yl)-1-oxopropan-2-ylamino)-N-isopropylacetamide;
(R)-3-(4-chlorophenyl)-2-(dimethylamino)-1-(4-((5R,7R)-7-hydroxy-5-methyl-6,7-dihydro-5H-cyclopenta[d]pyrimidin-4-yl)piperazin-1-yl)propan-1-one;
(R)-3-(4-chlorophenyl)-1-(4-((5R,7R)-7-hydroxy-5-methyl-6,7-dihydro-5H-cyclopenta[d]pyrimidin-4-yl)piperazin-1-yl)-2-(2-morpholinoethylamino)propan-1-one;
(R)-3-(4-chlorophenyl)-1-(4-((5R,7R)-7-hydroxy-5-methyl-6,7-dihydro-5H-cyclopenta[d]pyrimidin-4-yl)piperazin-1-yl)-2-(isopropylamino)propan-1-one;
(R)-3-(4-chlorophenyl)-1-(4-((5R,7R)-7-hydroxy-5-methyl-6,7-dihydro-5H-cyclopenta[d]pyrimidin-4-yl)piperazin-1-yl)-2-(tetrahydro-2H-pyran-4-ylamino)propan-1-one;
(R)-3-(4-chlorophenyl)-1-((S)-4-((5R,7R)-7-hydroxy-5-methyl-6,7-dihydro-5H-cyclopenta[d]pyrimidin-4-yl)-3-methylpiperazin-1-yl)-2-(isopropylamino)propan-1-one;
2-((R)-3-(4-chlorophenyl)-1-(4-((5R,7R)-7-hydroxy-5-methyl-6,7-dihydro-5H-cyclopenta[d]pyrimidin-4-yl)piperazin-1-yl)-1-oxopropan-2-ylamino)-N,N-dimethylacetamide;
(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(1,4-oxazepan-4-yl)propan-1-one;
(R)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(1,4-oxazepan-4-yl)propan-1-one;
(R)-2-(4-chloro-2-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;
(S)-2-(4-chloro-2-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;
(S)-2-(2-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;
(S)-2-(4-chlorophenyl)-3-(cyclohexylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chlorophenyl)-3-(cyclohexylamino)-1-(4-((5R,7S)-7-hydroxy-5-methyl-6,7-dihydro-5H-cyclopenta[d]pyrimidin-4-yl)piperazin-1-yl)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-methoxycyclohexylamino)propan-1-one;

(S)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-((S)-tetrahydrofuran-3-ylamino)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(4-methyltetrahydro-2H-pyran-4-ylamino)propan-1-one;

(R)-3-(4-chlorophenyl)-1-(4-((5R,7R)-7-hydroxy-5-methyl-6,7-dihydro-5H-cyclopenta[d]pyrimidin-4-yl)piperazin-1-yl)-2-(2-(tetrahydro-2H-pyran-4-yl)ethylamino)propan-1-one;

(R)-3-(4-chlorophenyl)-1-(4-((5R,7R)-7-hydroxy-5-methyl-6,7-dihydro-5H-cyclopenta[d]pyrimidin-4-yl)piperazin-1-yl)-2-(3,3,3-trifluoropropylamino)propan-1-one;

(R)-3-(4-chlorophenyl)-1-(4-((5R,7R)-7-hydroxy-5-methyl-6,7-dihydro-5H-cyclopenta[d]pyrimidin-4-yl)piperazin-1-yl)-2-((tetrahydro-2H-pyran-4-yl)methylamino)propan-1-one;

(R)-3-(4-chlorophenyl)-1-(4-((5R,7R)-7-hydroxy-5-methyl-6,7-dihydro-5H-cyclopenta[d]pyrimidin-4-yl)piperazin-1-yl)-2-(isopropyl(methyl)amino)propan-1-one;

(S)-3-(tert-butylamino)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

(R)-3-(tert-butylamino)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(4-methylpiperazin-1-yl)propan-1-one;

(R)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(4-methylpiperazin-1-yl)propan-1-one;

(S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one;

(R)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-morpholinopropan-1-one;

(R)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one;

(S)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(4-methylpiperazin-1-yl)propan-1-one;

(R)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(4-methylpiperazin-1-yl)propan-1-one;

(S)-3-(cyclopropylmethylamino)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)propan-1-one;

(S)-3-(cyclopropylmethylamino)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)propan-1-one;

(S)-1-(4-((5R,7R)-7-hydroxy-5-methyl-6,7-dihydro-5H-cyclopenta[d]pyrimidin-4-yl)piperazin-1-yl)-3-(isopropylamino)-2-(4-(trifluoromethyl)phenyl)propan-1-one;

(S)-3-amino-2-(4-bromophenyl)-1-(4-((5R,7S)-7-hydroxy-5-methyl-6,7-dihydro-5H-cyclopenta[d]pyrimidin-4-yl)piperazin-1-yl)propan-1-one;

(S)-3-amino-2-(4-chloro-3-fluorophenyl)-1-(4-((5R,7S)-7-hydroxy-5-methyl-6,7-dihydro-5H-cyclopenta[d]pyrimidin-4-yl)piperazin-1-yl)propan-1-one;

(S)-2-(4-bromophenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

3-((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropylamino)propanamide;

3-((S)-2-(4-chlorophenyl)-3-(4-((5R,7S)-7-hydroxy-5-methyl-6,7-dihydro-5H-cyclopenta[d]pyrimidin-4-yl)piperazin-1-yl)-3-oxopropylamino)propanamide;

(4-(4-chlorophenyl)piperidin-4-yl)(4-((5R,7R)-7-hydroxy-5-methyl-6,7-dihydro-5H-cyclopenta[d]pyrimidin-4-yl)piperazin-1-yl)methanone;

(S)-2-(4-bromophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-3-amino-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)propan-1-one;

(S)-3-amino-2-(4-bromophenyl)-1-(4-((5R,7R)-7-hydroxy-5-methyl-6,7-dihydro-5H-cyclopenta[d]pyrimidin-4-yl)piperazin-1-yl)propan-1-one;

(S)-2-(4-bromophenyl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(4-chloro-3-fluorophenyl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(3,4-dichlorophenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-3-amino-2-(3,4-dichlorophenyl)-1-(4-((5R,7S)-7-hydroxy-5-methyl-6,7-dihydro-5H-cyclopenta[d]pyrimidin-4-yl)piperazin-1-yl)propan-1-one;

(R)-2-(3,4-dichlorophenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one;

(S)-2-(3,4-dichlorophenyl)-1-(4-((5R,7R)-7-hydroxy-5-methyl-6,7-dihydro-5H-cyclopenta[d]pyrimidin-4-yl)piperazin-1-yl)-3-(4-isopropylpiperazin-1-yl)propan-1-one;

(S)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one;

(R)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one;

(S)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-(4-isopropylpiperazin-1-yl)propan-1-one;

(S)-2-(3,5-difluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-3-((R)-3-aminopyrrolidin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

(R)-3-((R)-3-aminopyrrolidin-1-yl)-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(4-isopropylpiperazin-1-yl)propan-1-one;

(S)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-morpholinopropan-1-one;

(R)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)-3-morpholinopropan-1-one;

(S)-3-(4-ethylpiperazin-1-yl)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)propan-1-one;

(R)-3-(4-ethylpiperazin-1-yl)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)propan-1-one;

(S)-3-(4-acetylpiperazin-1-yl)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)propan-1-one;

(R)-3-(4-acetylpiperazin-1-yl)-2-(3-fluoro-4-(trifluoromethoxy)phenyl)-1-(4-((5R,7R)-7-hydroxy-5-methyl-6,7-dihydro-5H-cyclopenta[d]pyrimidin-4-yl)piperazin-1-yl)propan-1-one;

(S)-2-(3,4-dichlorophenyl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(4-bromophenyl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one;

(S)-2-(4-chloro-3-fluorophenyl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one;

(S)-2-(4-chloro-3-fluorophenyl)-3-(cyclopropylmethylamino)-1-(4-((5R,7S)-7-hydroxy-5-methyl-6,7-dihydro-5H-cyclopenta[d]pyrimidin-4-yl)piperazin-1-yl)propan-1-one;

(S)-3-(bis(cyclopropylmethyl)amino)-2-(4-chloro-3-fluorophenyl)-1-(4-((5R,7S)-7-hydroxy-5-methyl-6,7-dihydro-5H-cyclopenta[d]pyrimidin-4-yl)piperazin-1-yl)propan-1-one;

(S)-2-(4-bromophenyl)-3-(cyclopropylmethylamino)-1-(4-((5R,7S)-7-hydroxy-5-methyl-6,7-dihydro-5H-cyclopenta[d]pyrimidin-4-yl)piperazin-1-yl)propan-1-one;

(S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(4-bromophenyl)-3-((cyclopropylmethyl)(methyl)amino)-1-(4-((5R,7S)-7-hydroxy-5-methyl-6,7-dihydro-5H-cyclopenta[d]pyrimidin-4-yl)piperazin-1-yl)propan-1-one;

(S)-2-(4-chloro-3-fluorophenyl)-3-(cyclopropylmethylamino)-1-(4-((5R,7R)-7-hydroxy-5-methyl-6,7-dihydro-5H-cyclopenta[d]pyrimidin-4-yl)piperazin-1-yl)propan-1-one;

(S)-3-(cyclopropylmethylamino)-2-(3,4-dichlorophenyl)-1-(4-((5R,7R)-7-hydroxy-5-methyl-6,7-dihydro-5H-cyclopenta[d]pyrimidin-4-yl)piperazin-1-yl)propan-1-one;

(S)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)-2-(4-(trifluoromethoxy)phenyl)propan-1-one;

(R)-2-(4-chlorophenyl)-3-((3S,5R)-3,5-dimethylpiperazin-1-yl)-1-(4-((5R,7R)-7-hydroxy-5-methyl-6,7-dihydro-5H-cyclopenta[d]pyrimidin-4-yl)piperazin-1-yl)propan-1-one;

(R)-2-(4-chlorophenyl)-3-((2S,6R)-2,6-dimethylmorpholino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chlorophenyl)-3-((2S,6R)-2,6-dimethylmorpholino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chlorophenyl)-3-((3S,5R)-3,5-dimethylpiperazin-1-yl)-1-(4-((5R,7R)-7-hydroxy-5-methyl-6,7-dihydro-5H-cyclopenta[d]pyrimidin-4-yl)piperazin-1-yl)propan-1-one;

(S)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one;

(R)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one;

(S)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(4-methylpiperazin-1-yl)propan-1-one;

(R)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(4-methylpiperazin-1-yl)propan-1-one;

(S)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(4-isopropylpiperazin-1-yl)propan-1-one;

(R)-2-(3-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(4-isopropylpiperazin-1-yl)propan-1-one;

(S)-3-(cyclopropylmethylamino)-1-(4-((5R,7R)-7-hydroxy-5-methyl-6,7-dihydro-5H-cyclopenta[d]pyrimidin-4-yl)piperazin-1-yl)-2-(4-(trifluoromethoxy)phenyl)propan-1-one;

(S)-3-amino-2-(4-bromo-3-fluorophenyl)-1-(4-((5R,7R)-7-hydroxy-5-methyl-6,7-dihydro-5H-cyclopenta[d]pyrimidin-4-yl)piperazin-1-yl)propan-1-one;

(S)-3-amino-2-(4-bromo-3-fluorophenyl)-1-(4-((5R,7S)-7-hydroxy-5-methyl-6,7-dihydro-5H-cyclopenta[d]pyrimidin-4-yl)piperazin-1-yl)propan-1-one;

(S)-2-(3,4-dichlorophenyl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one;

(S)-2-(4-bromo-3-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(4-bromo-3-fluorophenyl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one;

(S)-2-(4-bromo-3-fluorophenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(4-bromo-3-fluorophenyl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(4-bromo-3-fluorophenyl)-3-(cyclopropylmethylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-bromo-3-fluorophenyl)-3-(cyclopropylmethylamino)-1-(4-((5R,7S)-7-hydroxy-5-methyl-6,7-dihydro-5H-cyclopenta[d]pyrimidin-4-yl)piperazin-1-yl)propan-1-one;

(S)-2-(3-fluoro-4-(trifluoromethyl)phenyl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one;

(S)-2-(4-bromophenyl)-1-(4-((5R,7R)-7-hydroxy-5-methyl-6,7-dihydro-5H-cyclopenta[d]pyrimidin-4-yl)piperazin-1-yl)-3-(4-isopropylpiperazin-1-yl)propan-1-one;

(S)-2-(4-bromophenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one;

(S)-3-(cyclopropylmethylamino)-1-(4-((5R,7R)-7-hydroxy-5-methyl-6,7-dihydro-5H-cyclopenta[d]pyrimidin-4-yl)piperazin-1-yl)-2-(4-(trifluoromethyl)phenyl)propan-1-one;

(S)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)-2-(4-(trifluoromethyl)phenyl)propan-1-one;

(S)-3-(cyclopropylmethylamino)-2-(2-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)propan-1-one;

(R)-2-(4-bromo-3-fluorophenyl)-1-(4-((5R,7R)-7-hydroxy-5-methyl-6,7-dihydro-5H-cyclopenta[d]pyrimidin-4-yl)piperazin-1-yl)-3-(4-hydroxypiperidin-1-yl)propan-1-one;

(S)-2-(4-bromophenyl)-1-(4-((5R,7S)-7-hydroxy-5-methyl-6,7-dihydro-5H-cyclopenta[d]pyrimidin-4-yl)piperazin-1-yl)-3-(isopropyl(methyl)amino)propan-1-one;

(S)-3-amino-2-(4-bromo-2-fluorophenyl)-1-(4-((5R,7R)-7-hydroxy-5-methyl-6,7-dihydro-5H-cyclopenta[d]pyrimidin-4-yl)piperazin-1-yl)propan-1-one;

(S)-3-amino-2-(4-bromo-2-fluorophenyl)-1-(4-((5R,7S)-7-hydroxy-5-methyl-6,7-dihydro-5H-cyclopenta[d]pyrimidin-4-yl)piperazin-1-yl)propan-1-one;

(S)-2-(4-bromophenyl)-1-(4-((5R,7R)-7-hydroxy-5-methyl-6,7-dihydro-5H-cyclopenta[d]pyrimidin-4-yl)piperazin-1-yl)-3-(isopropyl(methyl)amino)propan-1-one;

(S)-2-(4-bromo-2-fluorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(4-bromo-2-fluorophenyl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one;

(S)-3-amino-2-(4-chloro-2-fluorophenyl)-1-(4-((5R,7R)-7-hydroxy-5-methyl-6,7-dihydro-5H-cyclopenta[d]pyrimidin-4-yl)piperazin-1-yl)propan-1-one;

2-(4-chlorophenyl)-3-((3S,4R)-4-(dimethylamino)-3-fluoropiperidin-1-yl)-1-(4-((5R,7R)-7-hydroxy-5-methyl-6,7-dihydro-5H-cyclopenta[d]pyrimidin-4-yl)piperazin-1-yl)propan-1-one;

(S)-2-(4-bromo-2-fluorophenyl)-3-(cyclopropylmethylamino)-1-(4-((5R,7S)-7-hydroxy-5-methyl-6,7-dihydro-5H-cyclopenta[d]pyrimidin-4-yl)piperazin-1-yl)propan-1-one;

(S)-3-(tert-butylamino)-1-(4-((5R,7R)-7-hydroxy-5-methyl-6,7-dihydro-5H-cyclopenta[d]pyrimidin-4-yl)piperazin-1-yl)-2-(4-(trifluoromethyl)phenyl)propan-1-one;

(S)-2-(3-fluoro-4-(trifluoromethoxy)phenyl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(3-fluoro-4-(trifluoromethyl)phenyl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(4-chloro-2-fluorophenyl)-3-(cyclopropylmethylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-bromo-2-fluorophenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(4-chloro-2-fluorophenyl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(4-chloro-2-fluorophenyl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)-2-(4-(trifluoromethyl)phenyl)propan-1-one;

(S)-3-(cyclopropylmethylamino)-1-(4-((5R,7S)-7-hydroxy-5-methyl-6,7-dihydro-5H-cyclopenta[d]pyrimidin-4-yl)piperazin-1-yl)-2-(4-(trifluoromethyl)phenyl)propan-1-one;

(S)-2-(4-bromophenyl)-3-(tert-butylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-(isobutylamino)propan-1-one;

(S)-2-(4-chloro-3-fluorophenyl)-3-(cyclopentylmethylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chloro-3-fluorophenyl)-3-(cyclopentylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(2-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)-3-(isopropyl(methyl)amino)propan-1-one;

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-((2-hydroxyethyl)(isopropyl)amino)propan-1-one;

(S)-2-(2-fluoro-4-(trifluoromethyl)phenyl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one;

(S)-2-(2-fluoro-4-(trifluoromethyl)phenyl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-3-amino-2-(2-fluoro-4-(trifluoromethyl)phenyl)-1-(4-((5R,7R)-7-hydroxy-5-methyl-6,7-dihydro-5H-cyclopenta[d]pyrimidin-4-yl)piperazin-1-yl)propan-1-one;

(S)-3-(cyclopropylmethylamino)-2-(3-fluoro-4-(trifluoromethyl)phenyl)-1-(4-((5R,7S)-7-hydroxy-5-methyl-6,7-dihydro-5H-cyclopenta[d]pyrimidin-4-yl)piperazin-1-yl)propan-1-one;

(S)-3-(cyclopropylmethylamino)-2-(3-fluoro-4-(trifluoromethoxy)phenyl)-1-(4-((5R,7S)-7-hydroxy-5-methyl-6,7-dihydro-5H-cyclopenta[d]pyrimidin-4-yl)piperazin-1-yl)propan-1-one;

(S)-2-(4-bromophenyl)-3-(4,4-dimethylcyclohexylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-bromophenyl)-3-(3,3-dimethylcyclohexylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chlorophenyl)-3-(4,4-dimethylcyclohexylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(4-chlorophenyl)-3-(3,3-dimethylcyclohexylamino)-1-(4-((5R,7R)-7-hydroxy-5-methyl-6,7-dihydro-5H-cyclopenta[d]pyrimidin-4-yl)piperazin-1-yl)propan-1-one;

(S)-1-(4-((5R,7R)-7-hydroxy-5-methyl-6,7-dihydro-5H-cyclopenta[d]pyrimidin-4-yl)piperazin-1-yl)-3-(isopropylamino)-2-(thiophen-2-yl)propan-1-one;

(S)-2-(5-bromothiophen-2-yl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(5-bromothiophen-2-yl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one;

(S)-2-(5-bromothiophen-2-yl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(R)-2-(5-bromopyridin-2-yl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(5-bromopyridin-2-yl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one;

(S)-2-(5-bromothiophen-2-yl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(5-bromothiophen-2-yl)-3-(cyclopropylmethylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(5-chlorothiophen-2-yl)-1-(4-((5R,7S)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(5-chlorothiophen-2-yl)-1-(4-((5R,7S)-7-hydroxy-5-methyl-6,7-dihydro-5H-cyclopenta[d]pyrimidin-4-yl)piperazin-1-yl)-3-(isopropylamino)propan-1-one;

(S)-2-(5-chlorothiophen-2-yl)-1-(4-((5R,7R)-7-hydroxy-5-methyl-6,7-dihydro-5H-cyclopenta[d]pyrimidin-4-yl)piperazin-1-yl)-3-(tetrahydro-2H-pyran-4-ylamino)propan-1-one;

(S)-2-(5-chlorothiophen-2-yl)-3-(cyclopropylmethylamino)-1-(4-((5R,7R)-7-hydroxy-5-methyl-6,7-dihydro-5H-cyclopenta[d]pyrimidin-4-yl)piperazin-1-yl)propan-1-one;

(S)-2-(5-chlorothiophen-2-yl)-3-(cyclopropylmethylamino)-1-(4-((5R,7S)-7-hydroxy-5-methyl-6,7-dihydro-5H-cyclopenta[d]pyrimidin-4-yl)piperazin-1-yl)propan-1-one; and salts thereof.

Another embodiment includes AKT inhibitors of Formula I, including the compounds:

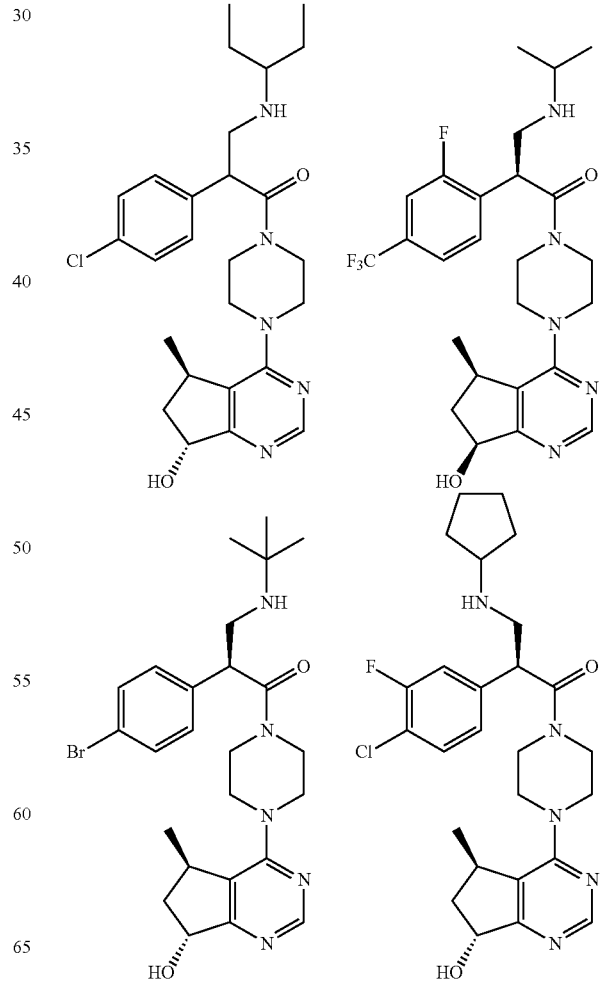

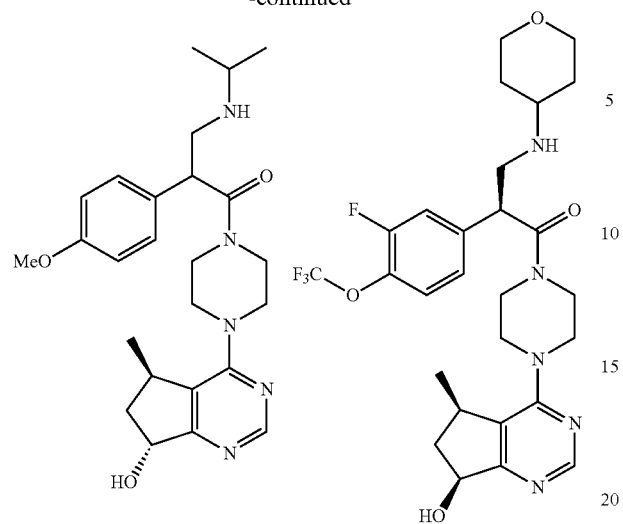
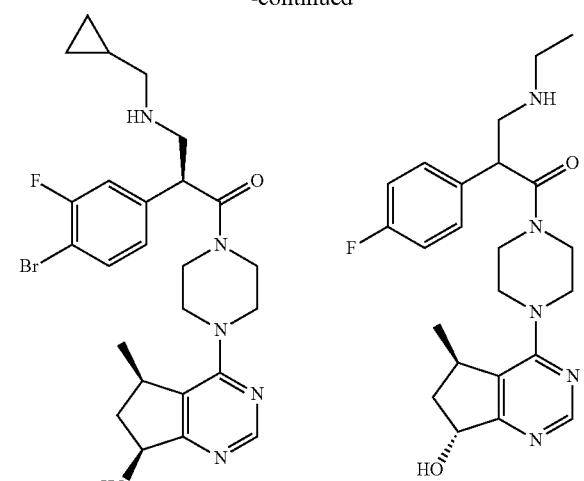
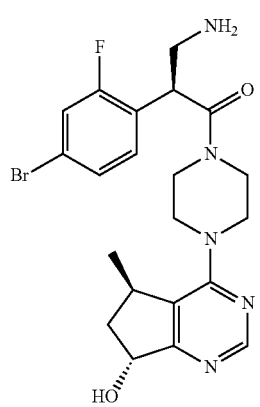
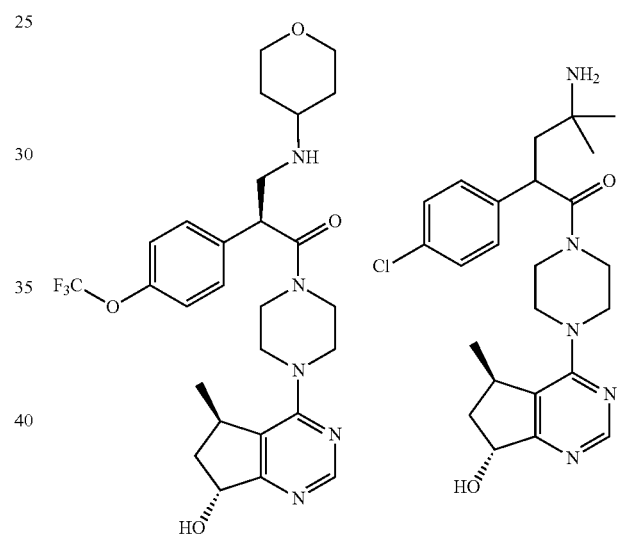
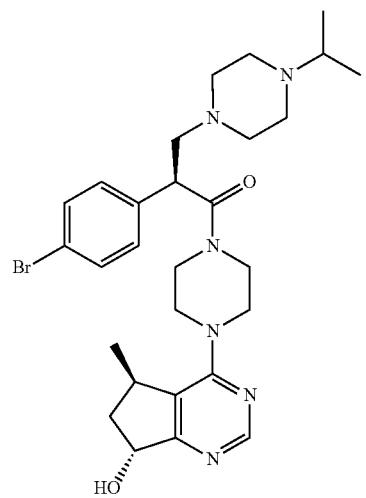
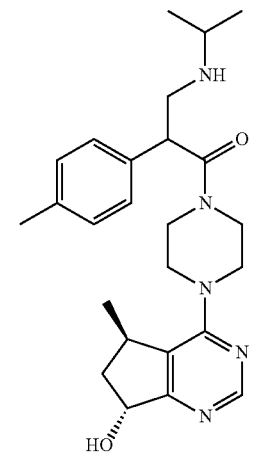

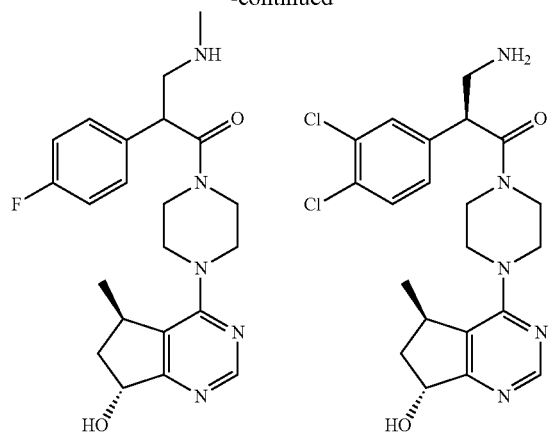
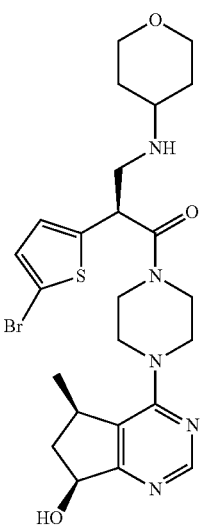
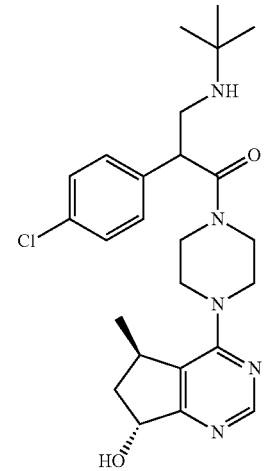
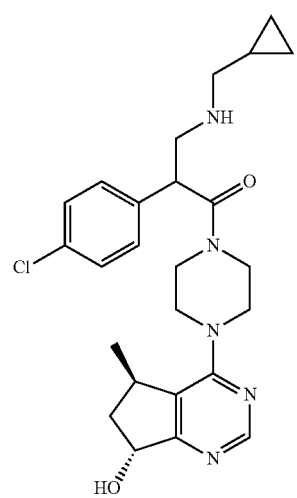
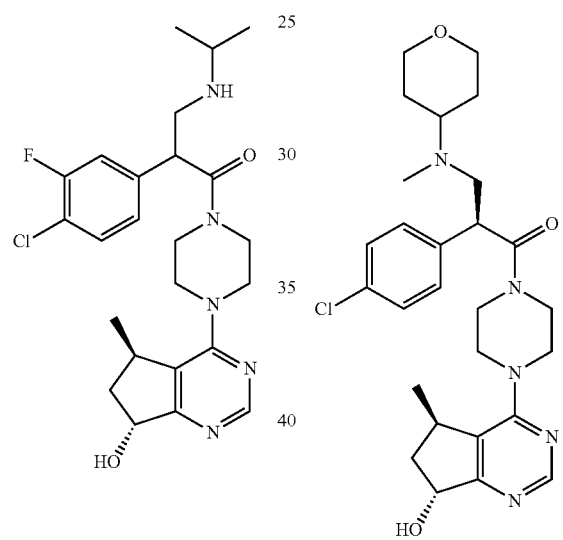
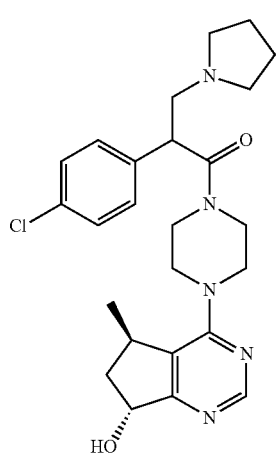
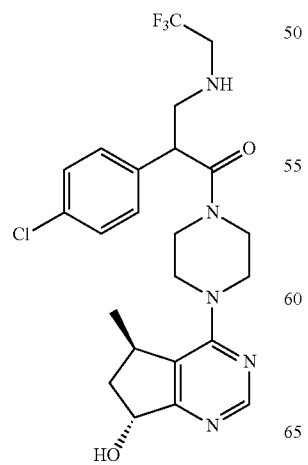
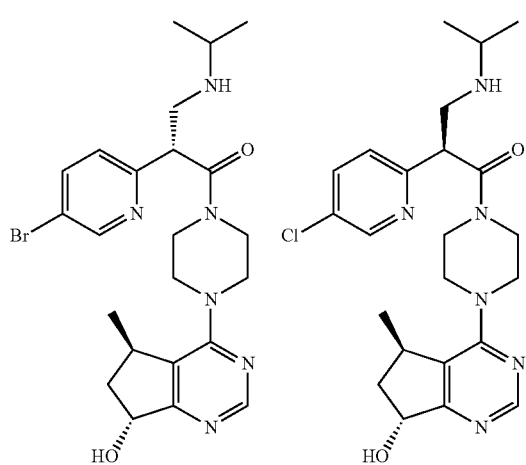

-continued

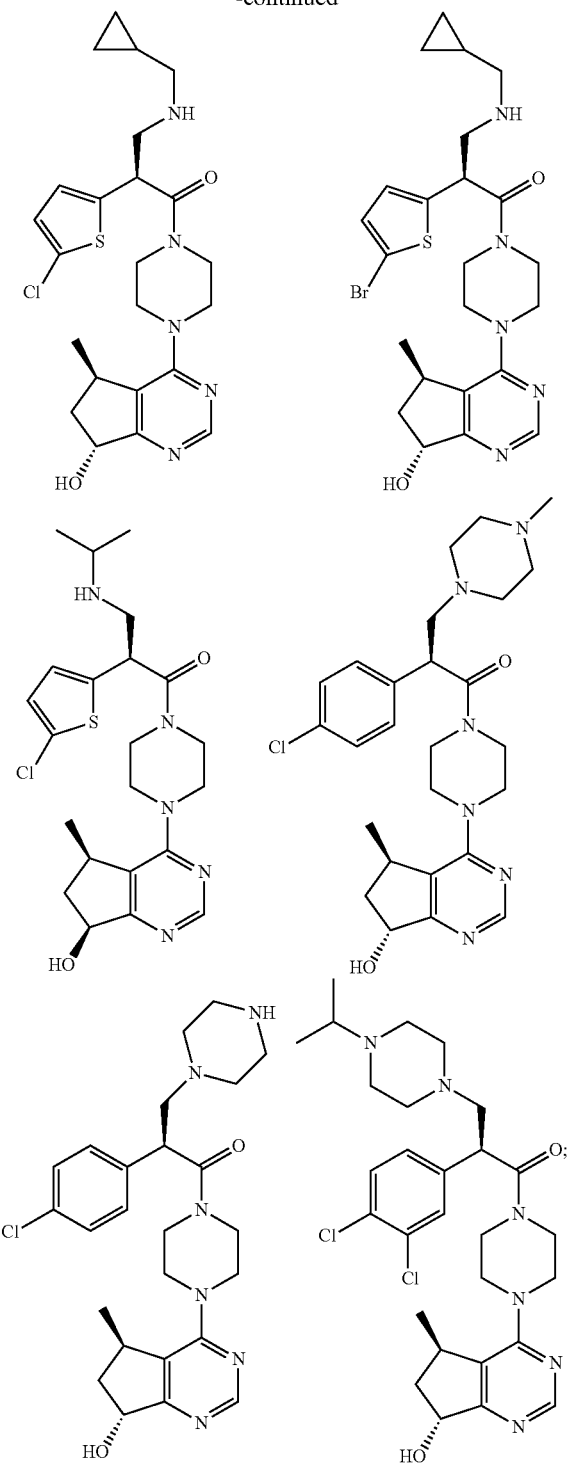

and salts thereof.

Preparation of Formula I Compounds

Compounds of Formula I may be prepared according to methods described in U.S. Patent Publication No. 2008/0051399 (U.S. patent application Ser. No. 11/773,949, filed Jul. 5, 2007, entitled "Hydroxylated and Methoxylated Pyrimidyl Cyclopentanes as AKT Protein Kinase Inhibitors"), which is incorporated by reference herein, for all purposes.

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry.

For illustrative purposes, Schemes 1-4 show a general method for preparing the compounds of Formula I as well as key intermediates. Those skilled in the art will appreciate that other synthetic routes may be used. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

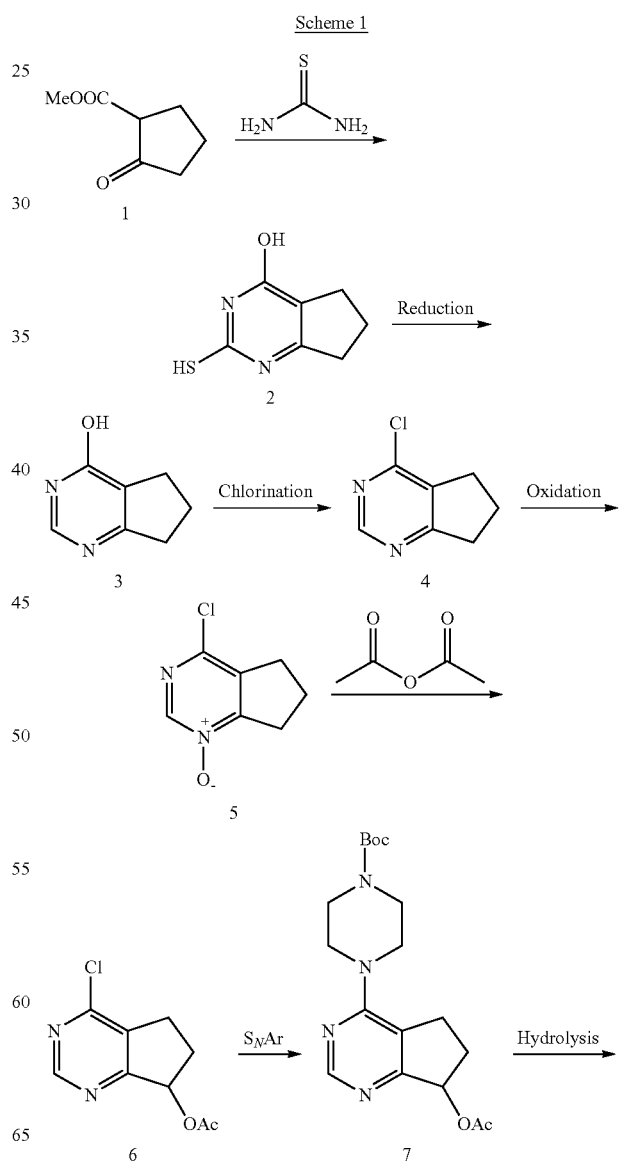

Scheme 1

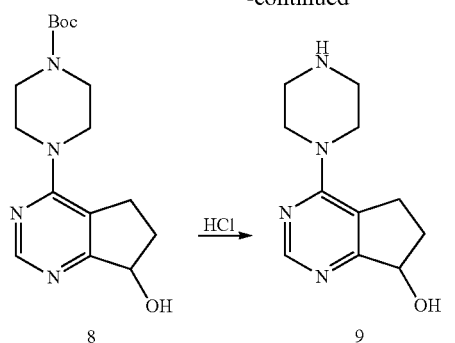

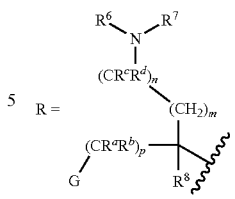

$$R = \begin{array}{c} R^6\diagdown N \diagup R^7 \\ (CR^cR^d)_n \\ | \\ (CH_2)_m \\ | \\ (CR^aR^b)_p \diagup C \diagdown R^8 \\ G \end{array}$$

Scheme 1 shows a method of preparing compound 10 of Formula I wherein $R^1$ is H, $R^2$ is OH and $R^5$ is H. Formation of pyrimidine 2 can be accomplished by the reaction of the keto ester 1 with thiourea in the presence of a base such as KOH in an appropriate solvent, such as ethanol. After reduction of the mercapto group of compound 2 under standard reducing conditions (e.g., Raney Ni and NH₄OH) to provide compound 3, the hydroxypyrimidine 3 can be chlorinated under standard conditions (e.g., POCl₃ in DIEA/DCE) to provide compound 4. Compound 4 is then oxidized under standard conditions (e.g., MCPBA in an appropriate solvent such as CHCl₃) to give the pyrimidine-oxide 5. Treatment of the pyrimidine-oxide with acetic anhydride gives the rearrangement product 6. Compound 7 is obtained by reacting compound 6 with an appropriately substituted piperidine under standard $S_NAr$ reaction conditions to provide compound 7. Compound 7 is hydrolyzed to provide compound 8, which is then deprotected to yield the intermediate 9. Acylation of the piperazinyl cyclopenta[d]pyrimidine 9 with an appropriated amino acid in the presence of a coupling reagent such as HBTU, followed by deprotection if necessary, gives compound 10 of Formula I.

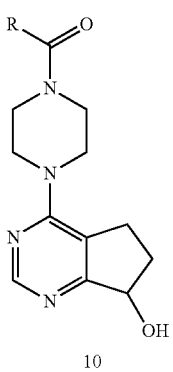

Scheme 2

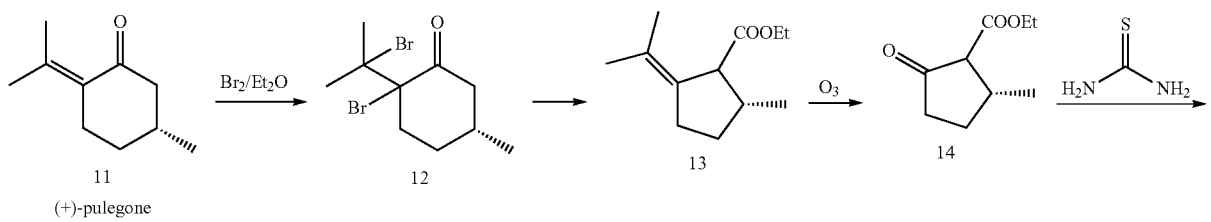

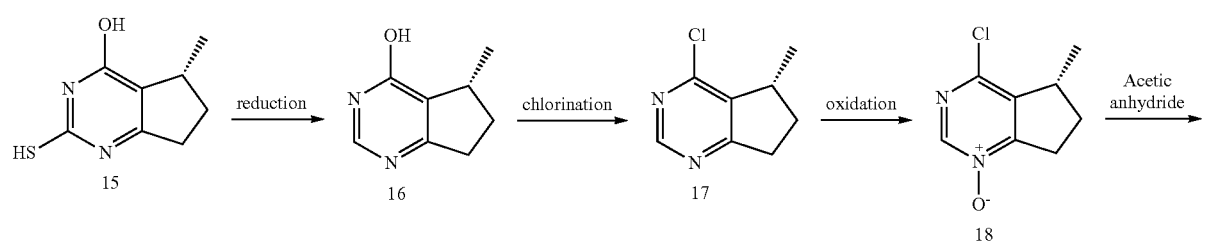

-continued

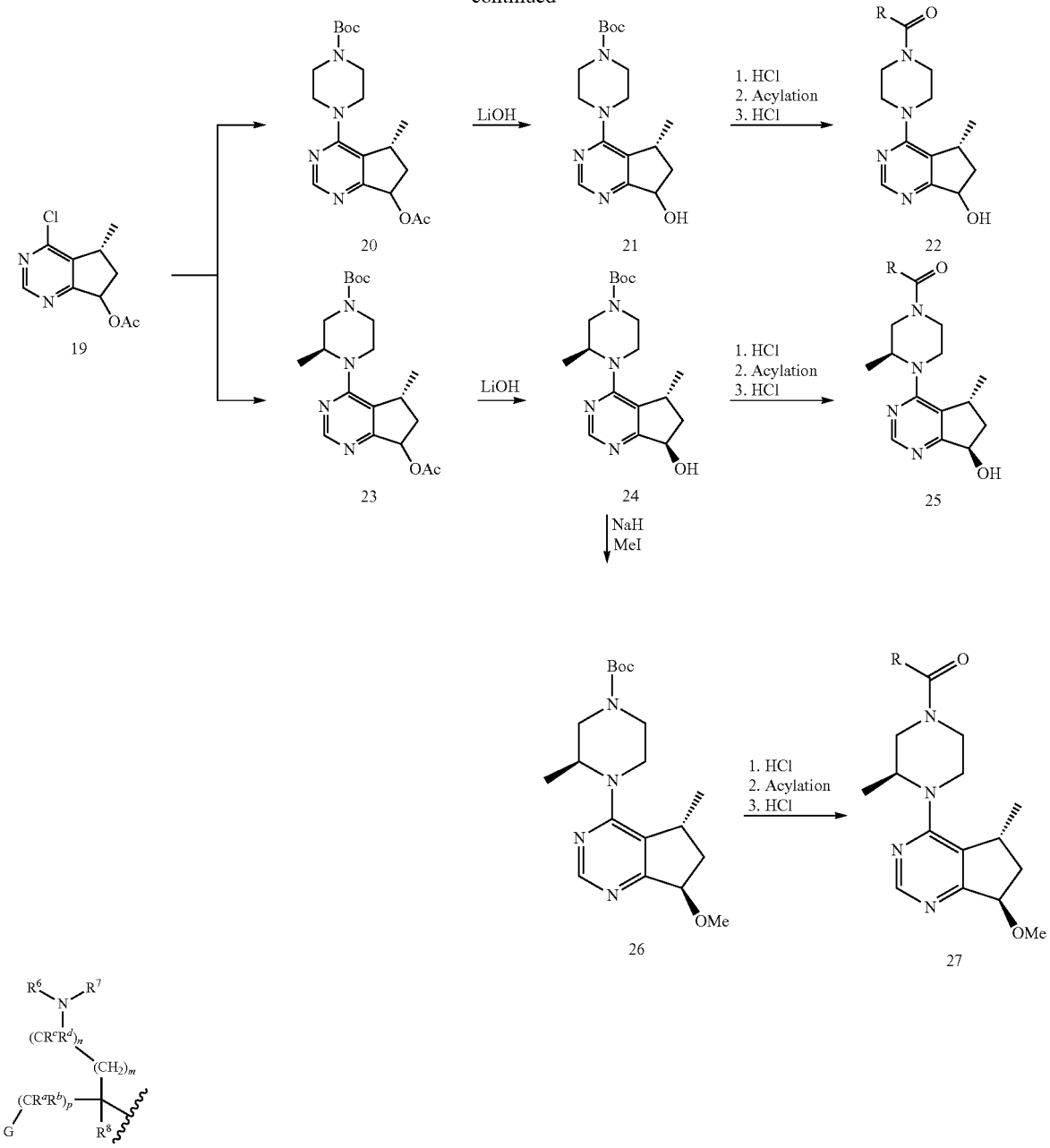

Scheme 2 shows a method of preparing compounds 22, 25 and 27 of Formula I wherein $R^1$, $R^2$ and $R^5$ are methyl. According to Scheme 2, bromination of (+)-pulegone 11 with bromine gives the dibromide 12. The treatment of the dibromide 12 with a base such as sodium ethoxide provides the pulegenate 13. Ozonolysis of the pulegenate 13 gives the ketoester 14. Treatment of the keto ester 14 with thiourea in the presence of a base such as KOH in ethanol, followed by reduction of the mercapto group under standard conditions (e.g. Raney Ni catalyst in ammonia) affords the hydroxypyrimidine 16. Chlorination of the hydroxypyrimidine 16 under standard conditions (e.g., $POCl_3$) provides the 4-chloropyrimidine 17. The oxidation of the 4-chloropyrimidine 17 with an oxidizing agent such as MCPBA or hydrogen peroxide provides the N-oxide 18. Rearrangement of the N-oxide 18 with acetic anhydride yields the intermediate 19. Compound 19 is reacted with the desired piperazine according to the procedure described in Scheme 1 to provide compound 20 where $R^5$ is H and 23 where $R^5$ is Me. Compounds 20 and 23 are subjected to chiral separation using HPLC with chiral stationary and then hydrolyzed upon treatment with a base such as lithium hydroxide to provide compounds 21 and 24, respectively. After deprotection, compounds 21 and 24 are then reacted with the appropriate amino acid to provide compounds 22 and 25, respectively.

Alternatively, the 7-hydroxy group of compound 24 may be alkylated with alkylation reagent such as alkyl halide in the presence of a base such as NaH or KOH to provide compound 26 where $R^2$ is Me. After deprotection, compound 26 is then reacted with the appropriate amino acid to provide compound 27.

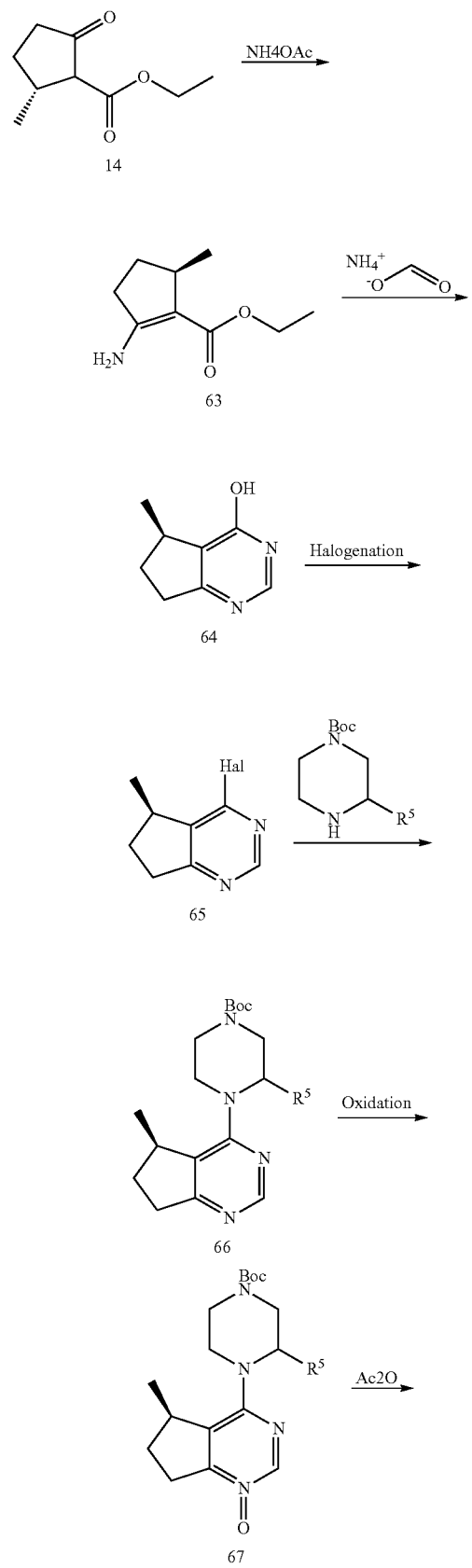

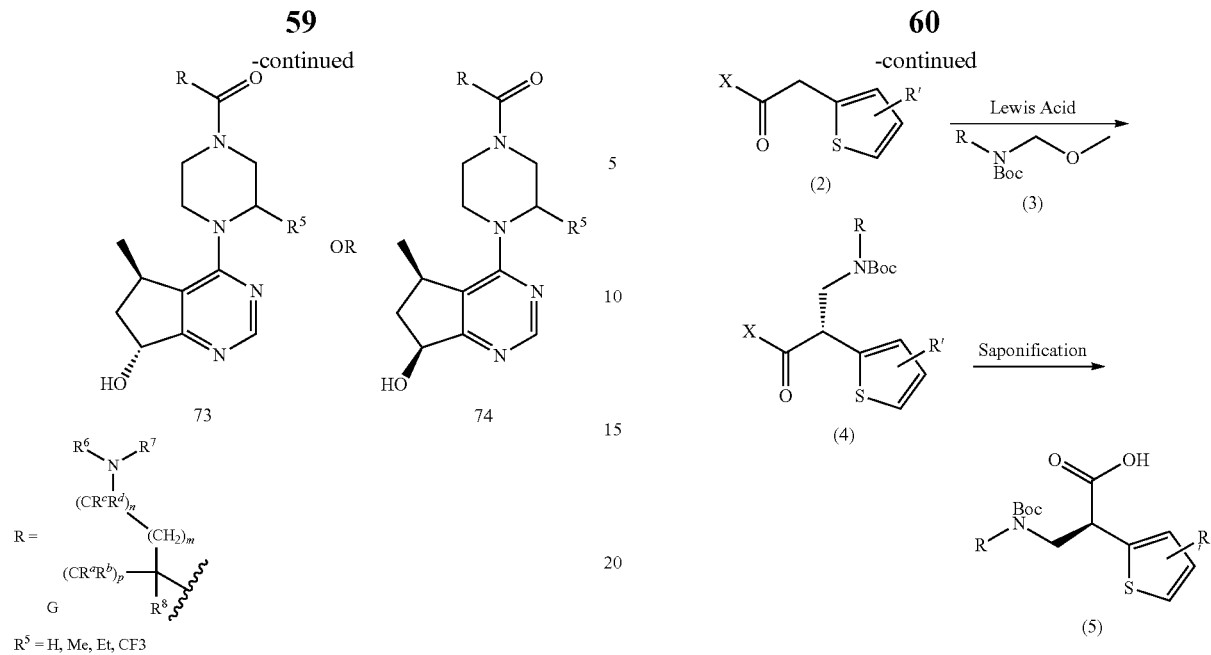

Scheme 3 shows an alternative method of preparing compounds 73 and 74. According to Scheme 3, amination of 14 using an ammonia synthon gives 63. Pyrimidine formation using, for example, ammonium formate in the presence of formamide at 50° C.-250° C. and/or at high pressure gives the bicyclic unit 64. Activation of 64 using, for example, POCl₃ or SOCl₂ gives the activated pyrimidine 65. Displacement of this leaving group, using a suitable protected/substituted piperidine at 0° C. to 150° C. gives the piperidine 66. Oxidation, using, for example, m-chloroperoxybenzoic acid ("MCPBA" or "m-CPBA") or Oxone® at −20° C. to 50° C. gives the N-oxide 67. Treatment with an acylating agent (eg. acetic anhydride) followed by heating (40° C. to 200° C.) causes rearrangement to give 68. Hydrolysis, using, for example LiOH or NaOH at 0° C. to 50° C. gives the alcohol 69. Oxidation, using for example, Swern conditions, MnO₄ or pyridine-SO₃ complex at appropriate temperatures gives the ketone 70. Asymmetric reduction using, for example, a catalytic chiral catalyst in the presence of hydrogen, the CBS catalyst or a borohydride reducing agent in the presence of a chiral ligand gives rise to either the (R) or the (S) stereochemistry at the alcohol 71 or 72. Alternatively, a non-chiral reducing agent could be used (eg. H₂, Pd/C), allowing the methyl group on the cyclopentane unit to provide facial selectivity and ultimately diastereoselectivity. If the reduction gives a lower diastereoselctivity, the diastereomers could be separated by (for example) chromatography, crystallization or derivitization. Finally deprotection of the Boc-group, using, for example, acid at 0° C. to 50° C., acylation using an appropriately functionalized amino acid and final functionalization of the amine of this amino acid (eg. removal of any protecting group, alkylation, reductive amination or acylation to introduce new substituents) gives rise to the final compounds 73 and 74.

Scheme 4

Introduction of a chiral auxiliary (e.g. Evans oxazolidinone, etc.) to compound (1) may be accomplished by standard acylation procedures to give the conjugate (2). For example, treatment of the acid with an activating agent (e.g. COCl₂) or mixed anhydride formation (e.g. 2,2-dimethylpropanoyl chloride) in the presence of an amine base at −20° C. to 100° C. followed by treatment with the appropriate chiral auxiliary (X) gives compound (2). The stereochemistry and choice of the chiral auxiliary may determine the stereochemistry of the newly created chiral center and the diastereoselectivity. Treatment of compound (2) with a Lewis acid (eg. TiCl₄) at low temperature (e.g. −20° C. to −100° C.) and an amine base (e.g. Hunig's base) followed by the use of an appropriately substituted imminium ion precursor (3) at low temperature then gives rise to compound (4). The temperature, Lewis acid and chiral auxiliary may all be expected to influence the diastereoselectivity of the addition adduct. Finally, saponification under mild conditions (e.g. LiOH/H₂O at −10° C. to 30° C.) gives rise to the desired acid (5).

In another embodiment, the AKT kinase inhibitor is an ATP-competitive, pan-AKT inhibitor of Formula II:

stereoisomers, tautomers or pharmaceutically acceptable salts thereof, wherein:

G is phenyl optionally substituted with one to three $R^a$ groups or a 5-6 membered heteroaryl optionally substituted by a halogen;

$R^1$ and $R^{1a}$ are independently selected from H, Me, $CF_3$, $CHF_2$ or $CH_2F$;

$R^2$ is H, For —OH;

$R^2a$ is H;

$R^3$ is H;

$R^4$ is H, or $C_1$-$C_4$ alkyl optionally substituted with F, —OH or —O($C_1$-$C_3$ alkyl);

$R^5$ and $R^{5a}$ are independently selected from H and $C_1$-$C_4$ alkyl, or $R^5$ and $R^{5a}$ together with the atom to which they are attached form a 5-6 membered cycloalkyl or 5-6 membered heterocycle, wherein the heterocycle has an oxygen heteroatom;

each $R^a$ is independently halogen, $C_1$-$C_6$-alkyl, $C_3$-$C_6$-cycloalkyl, —O—($C_1$-$C_6$-alkyl), $CF_3$, —$OCF_3$, S($C_1$-$C_6$-alkyl), CN, —$OCH_2$-phenyl, $NH_2$, —$NO_2$, —NH—($C_1$-$C_6$-alkyl), —N—($C_1$-$C_6$-alkyl)$_2$, piperidine, pyrrolidine, $CH_2F$, $CHF_2$, —$OCH_2F$, —$OCHF_2$, —OH, —$SO_2$($C_1$-$C_6$-alkyl), C(O)$NH_2$, C(O)NH($C_1$-$C_6$-alkyl), and C(O)N($C_1$-$C_6$-alkyl)$_2$; and j is 1 or 2.

Another embodiment includes AKT inhibitor compounds, including:

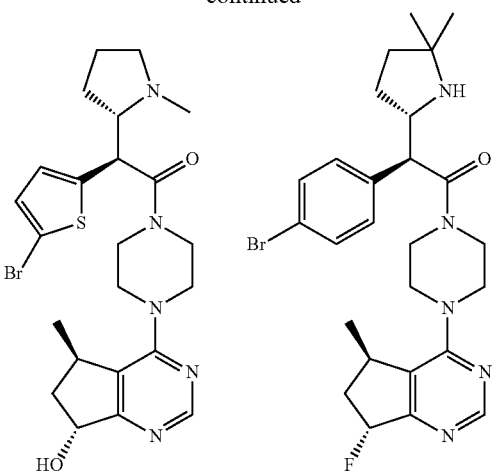

-continued

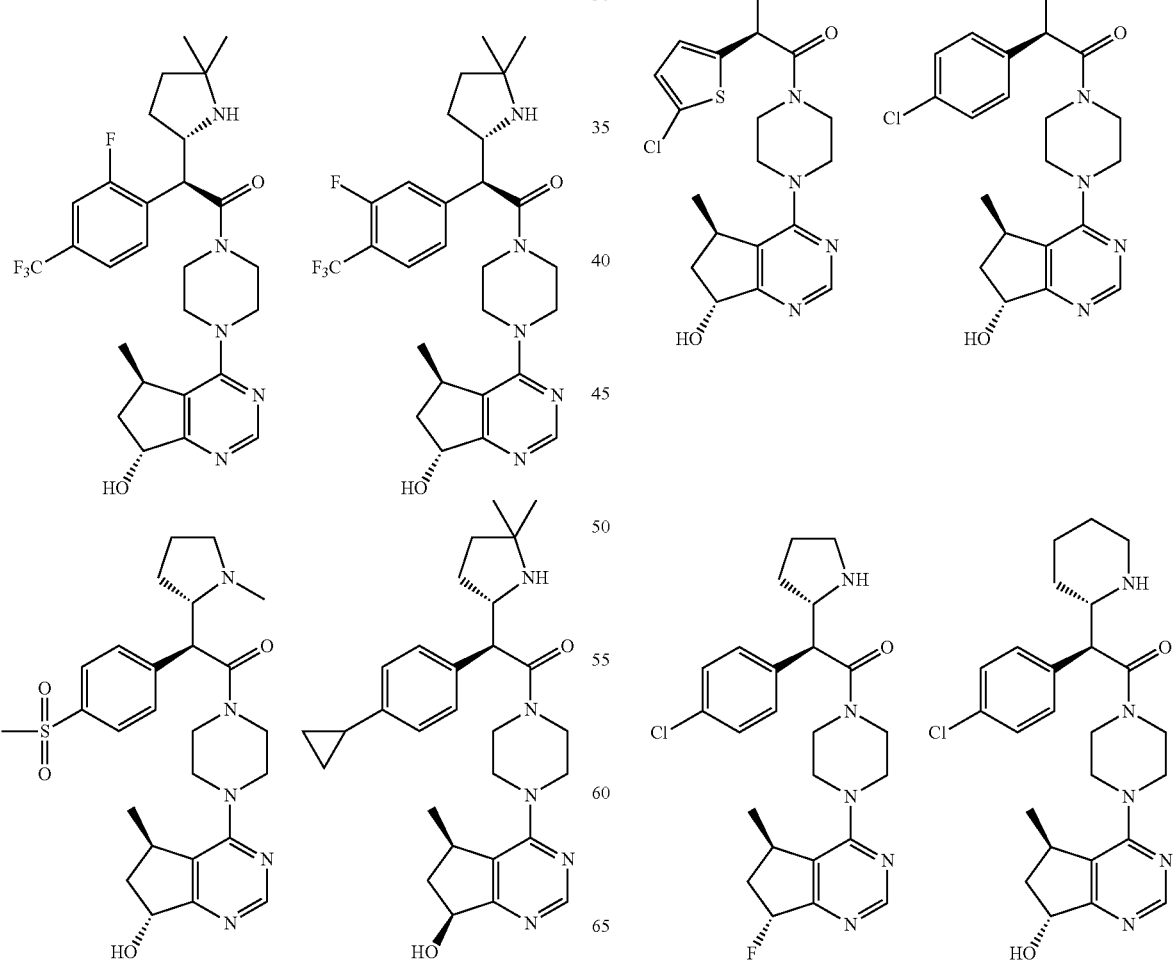

63
-continued
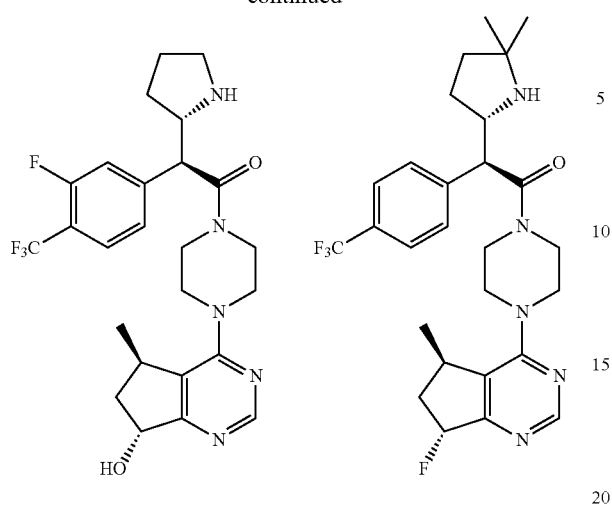
64
-continued
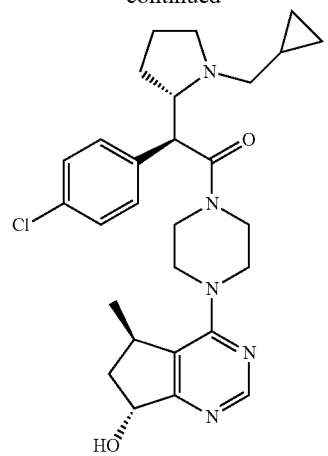
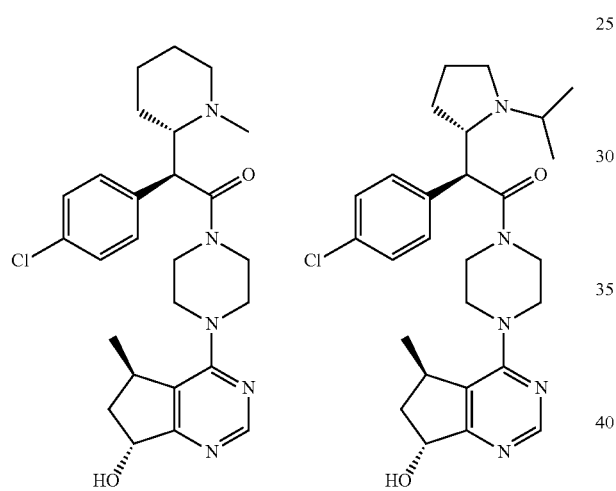
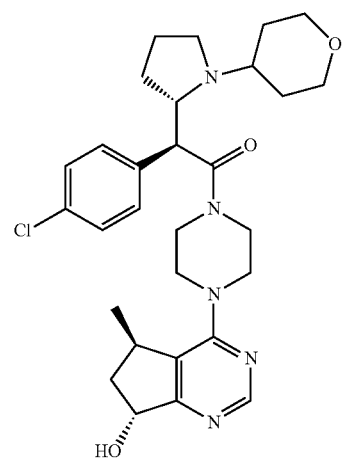
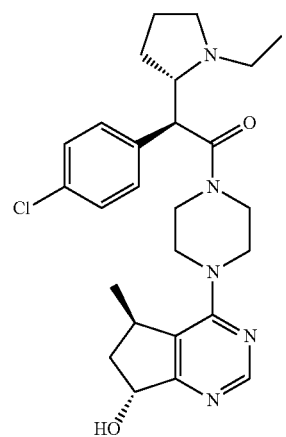
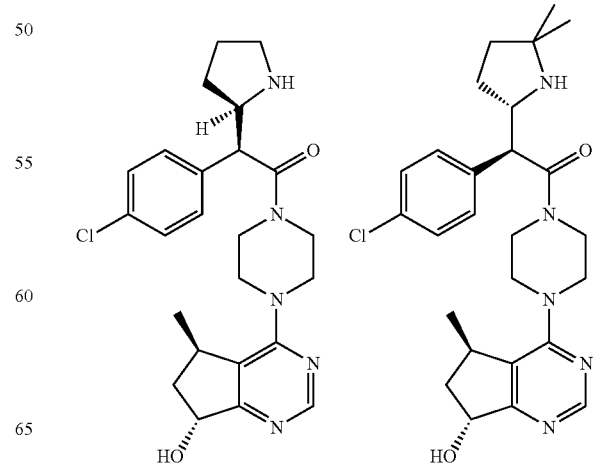

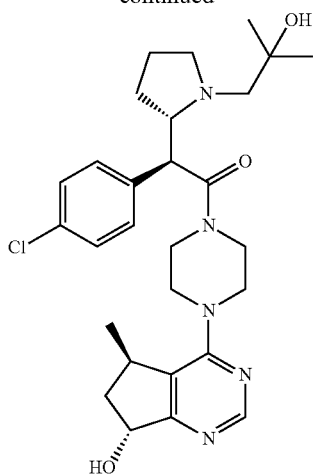

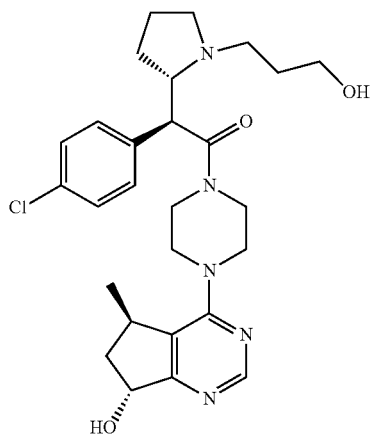

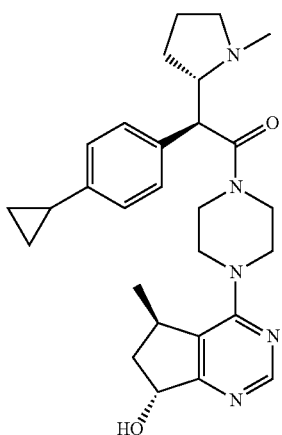

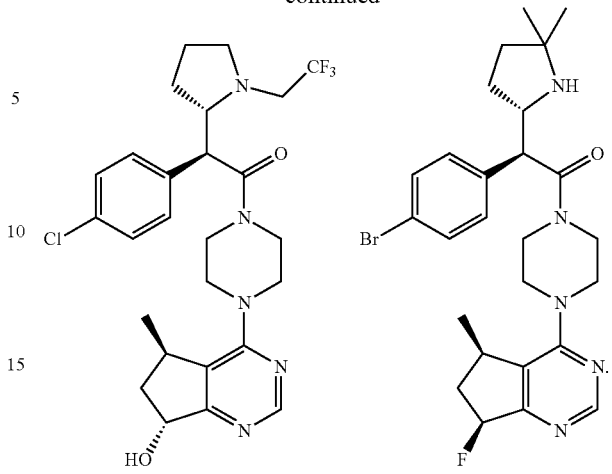

In one embodiment, the AKT inhibitor is a compound of the above formulas selected from GDC-0068 and salts thereof, the formula of GDC-0068 is:

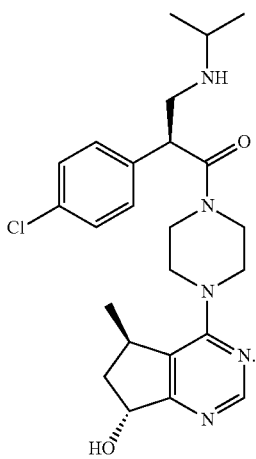 [SMILES: CC(C)NC[C@@H](C(=O)N1CCN(c2ncnc3c2[C@H](C)C[C@H]3O)CC1)c1ccc(Cl)cc1]

Compounds of Formula II may be prepared according to methods described in WO 2009006567, which is incorporated by reference herein, for all purposes.

In one embodiment, the AKT inhibitor is an allosteric AKT inhibitor of Formula III:

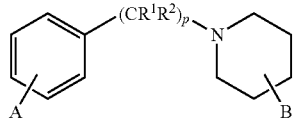

wherein, $R^1$ and $R^2$ are independently hydrogen, $C_1$-$C_5$ alkyl, hydroxyl, $C_{1-5}$ alkoxy or amine; p is an integer from 1 to 6; A is a 5-14 carbon cyclic, bicyclic or tricyclic aromatic or heteroaromatic ring, which can be optionally substituted with halogen, OH, amino, dialkylamino, monoalkylamino, $C_1$-$C_6$-alkyl or phenyl, which is optionally substituted with halogen, OH, $C_1$-$C_3$ alkyl or cyclopropylmethyl; and in one embodiment A has one of the following structures:

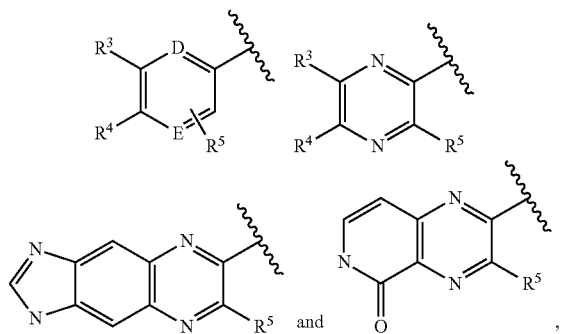

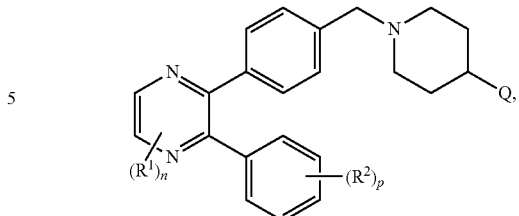

wherein: a is 0 or 1; b is 0 or 1; m is 0, 1 or 2; n is 0, 1 or 2; p is 0, 1 or 2; r is 0 or 1; s is 0 or 1;

Q is selected from: —$NR^7R^8$,

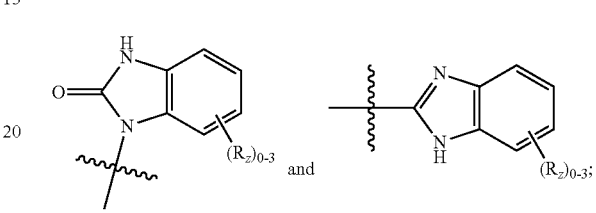

wherein D and E are independently —CH or N;

wherein $R^3$ and $R^4$ are each independently hydrogen, halogen, OH, amino, dialkylamino, monoalkylamino or $C_1$-$C_6$-alkyl, which is optionally substituted with halogen, OH, $C_1$-$C_3$ alkyl or cyclopropylmethyl;

$R^5$ is a 5 or 6 membered aromatic or heteroaromatic ring optionally substituted with halogen, OH, amino, dialkylamino, monoalkylamino or $C_1$-$C_6$-alkyl, which is optionally substituted with halogen, OH, $C_1$-$C_3$ alkyl or cyclopropylmethyl; in one embodiment $R^5$ is phenyl;

B is an aromatic, heteroaromatic, cyclic or heterocyclic ring having the formula:

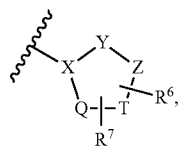

wherein, Q, T, X and Y are each independently selected from the group consisting of —CH, —$CH_2$, C═O, N or O;

Z is —CH, —$CH_2$, C═O, N, O or —C═C—;

$R^6$ and $R^7$ are independently selected from the group consisting of hydrogen, halogen, carbonyl and a 5 or 6 membered aromatic or heteroaromatic ring optionally substituted with halogen, OH, amino, dialkylamino, monoalkylamino or $C_1$-$C_6$-alkyl, which is optionally substituted with halogen, OH, $C_1$-$C_3$ alkyl or cyclopropylmethyl; in one embodiment $R^6$ or $R^7$ is pyridinyl, or $R^6$ and $R^7$ are taken together to form a 5-6 membered aromatic, heteroaromatic, cyclic or heterocyclic ring, which can be optionally substituted with halogen, OH, amino, dialkylamino, monoalkylamino or $C_1$-$C_6$-alkyl, which is optionally substituted with halogen, OH, $C_1$-$C_3$ alkyl or cyclopropylmethyl; in one embodiment, B has one of the following structures:

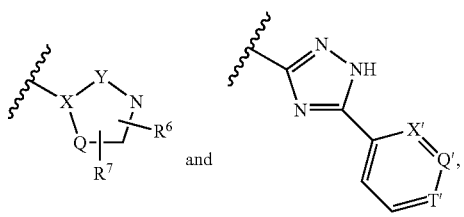

wherein X, Y, Q, $R^6$ and $R^7$ are as described above, and X', Q' and T' are —CH or N.

Another embodiment includes an allosteric AKT inhibitor having the formula:

$R^1$ is independently selected from (C═O)$_a$O$_b$$C_1$-$C_6$ alkyl, (C═O)$_a$O$_b$aryl, $C_2$-$C_6$ alkenyl, $C_2$-$C_6$ alkynyl, (C═O)$_a$O$_b$-heterocyclyl, (C═O)$_a$O$_b$$C_3$-$C_6$ cycloalkyl, $CO_2$H, halogen, CN, OH, O$_b$$C_1$-$C_6$perfluoroalkyl, O$_a$(C═O)$_b$$NR^7R^8$, $NR^c$(C═O)$NR^7R^8$, S(O)$_m$$R^a$, S(O)$_2$$NR^7R^8$, $NR^c$S(O)$_m$$R^a$, oxo, CHO, $NO_2$, $NR^c$(C═O)O$_b$$R^a$, O(C═O)O$_b$$C_1$-$C_6$ alkyl, O(C═O)O$_b$$C_3$-$C_6$ cycloalkyl, O(C═O)O$_b$aryl, and O(C═O)O$_b$-heterocycle, wherein said alkyl, aryl, alkenyl, alkynyl, heterocyclyl, and cycloalkyl are optionally substituted with one or more substituents selected from $R^z$;

$R^2$ is independently selected from $C_1$-$C_6$ alkyl, aryl, heterocyclyl, $CO_2$H, halo, CN, OH and S(O)$_2$$NR^7R^8$, wherein said alkyl, aryl and heterocyclyl are optionally substituted with one, two or three substituents selected from $R^z$;

$R^7$ and $R^8$ are independently selected from H, (C═O)O$_b$$C_1$-$C_{10}$ alkyl, (C═O)O$_b$$C_3$-$C_8$ cycloalkyl, (C═O)O$_b$aryl, (C═O)O$_b$heterocyclyl, $C_1$-$C_{10}$ alkyl, aryl, $C_2$-$C_{10}$ alkenyl, $C_2$-$C_{10}$ alkynyl, heterocyclyl, $C_3$-$C_8$ cycloalkyl, $SO_2R^a$ and (C═O)$NR^b_2$, wherein said alkyl, cycloalkyl, aryl, heterocylyl, alkenyl, and alkynyl is optionally substituted with one or more substituents selected from $R^z$, or $R^7$ and $R^8$ can be taken together with the nitrogen to which they are attached to form a monocyclic or bicyclic heterocycle with 5-7 members in each ring and optionally containing, in addition to the nitrogen, one or two additional heteroatoms selected from N, O and S, said monocyclic or bicyclic heterocycle optionally substituted with one or more substituents selected from $R^z$;

$R^z$ is selected from: (C═O)$_r$O$_s$($C_1$-$C_{10}$) alkyl, O$_r$($C_1$-$C_3$) perfluoroalkyl, ($C_0$-$C_6$)alkylene-S(O)$_m$$R^a$, oxo, OH, halo, CN, (C═O)$_r$O$_s$($C_2$-$C_{10}$) alkenyl, (C═O)$_r$O$_s$($C_2$-$C_{10}$) alkynyl, (C═O)$_r$O$_s$($C_3$-$C_6$) cycloalkyl, (C═O)$_r$O$_s$($C_0$-$C_6$) alkylene-aryl, (C═O)$_r$O$_s$($C_0$-$C_6$) alkylene-heterocyclyl, (C═O)$_r$O$_s$($C_0$-$C_6$) alkylene-N($R^b$)$_2$, C(O)$R^a$, ($C_0$-$C_6$)alkylene-$CO_2R^a$, C(O)H, ($C_0$-$C_6$)alkylene-$CO_2$H, C(O)N($R^b$)$_2$, S(O)$_m$$R^a$, and S(O)$_2$N($R^b$)$_2$$NR^c$(C═O)O$_b$$R^a$, O(C═O)O$_b$$C_1$-$C_{10}$ alkyl, O(C═O)O$_b$$C_3$-$C_8$ cycloalkyl, O(C═O)O$_b$aryl, and O(C═O)O$_b$-heterocycle, wherein said alkyl, alkenyl, alkynyl, cycloalkyl, aryl, and heterocyclyl are optionally substituted with up to three substituents selected from $R^b$, OH, ($C_1$-$C_6$)alkoxy, halogen, $CO_2$H, CN, O(C═O) $C_1$-$C_6$ alkyl, oxo, and N($R^b$)$_2$;

$R^a$ is $(C_1-C_6)$alkyl, $(C_3-C_6)$cycloalkyl, aryl or heterocyclyl; and $R^b$ is H, $(C_1-C_6)$alkyl, aryl, heterocyclyl, $(C_3-C_6)$cycloalkyl, $(C=O)OC_1-C_6$ alkyl, $(C=O)C_1-C_6$ alkyl or $S(O)_2R^a$;

$R^c$ is selected from: H, $C_1-C_6$ alkyl, aryl, $C_2-C_6$ alkenyl, $C_2-C_6$ alkynyl, heterocyclyl, $C_3-C_8$ cycloalkyl and $C_1-C_6$perfluoroalkyl, wherein said alkyl, cycloalkyl, aryl, heterocylyl, alkenyl, and alkynyl is optionally substituted with one or more substituents selected from $R^z$;

or a pharmaceutically acceptable salt or a stereoisomer thereof.

Another embodiment includes an allosteric AKT inhibitor having the formula:

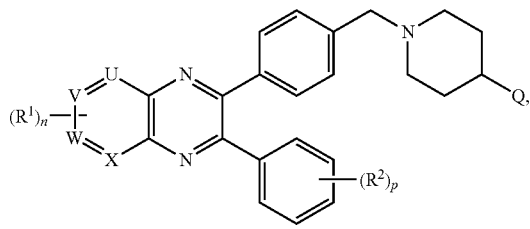

wherein a is 0 or 1; b is 0 or 1; m is 0, 1 or 2; n is 0, 1, 2 or 3; p is 0, 1 or 2; r is 0 or 1; s is 0 or 1; u, v, w and x are independently selected from: CH and N, provided that only one of u, v, w and x may be N;

Q is selected from: —NR$^5$R$^6$,

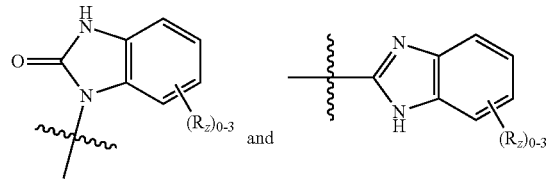

$R^1$ is independently selected from $(C=O)_aO_bC_1-C_6$ alkyl, $(C=O)_aO_b$aryl, $C_2-C_6$ alkenyl, $C_2-C_6$ alkynyl, $(C=O)_aO_b$-heterocyclyl, $(C=O)_aO_bC_3-C_6$ cycloalkyl, $CO_2H$, halogen, CN, OH, $O_bC_1-C_6$perfluoroalkyl, $O_a(C=O)_bNR^7R^8$, $NR^c(C=O)NR^7R^8$, $S(O)_mR^a$, $S(O)_2NR^7R^8$, $NR^cS(O)_mR^a$, oxo, CHO, $NO_2$, $NR^c(C=O)O_bR^a$, $O(C=O)O_bC_1-C_6$ alkyl, $O(C=O)O_bC_3-C_6$ cycloalkyl, $O(C=O)O_b$aryl, and $O(C=O)O_b$-heterocycle, wherein said alkyl, aryl, alkenyl, alkynyl, heterocyclyl, and cycloalkyl are optionally substituted with one or more substituents selected from $R^z$;

$R^2$ is independently selected from $C_1-C_6$ alkyl, aryl, heterocyclyl, $CO_2H$, halo, CN, OH and $S(O)_2NR^7R^8$, wherein said alkyl, aryl and heterocyclyl are optionally substituted with one, two or three substituents selected from $R^z$;

$R^7$ and $R^8$ are independently selected from H, $(C=O)O_bC_1-C_{10}$ alkyl, $(C=O)O_bC_3-C_8$ cycloalkyl, $(C=O)O_b$aryl, $(C=O)O_b$heterocyclyl, $C_1-C_{10}$ alkyl, aryl, $C_2-C_{10}$ alkenyl, $C_2-C_{10}$ alkynyl, heterocyclyl, $C_3-C_8$ cycloalkyl, $SO_2R^a$ and $(C=O)NR^b{}_2$, wherein said alkyl, cycloalkyl, aryl, heterocylyl, alkenyl, and alkynyl is optionally substituted with one or more substituents selected from $R^z$, or $R^7$ and $R^8$ can be taken together with the nitrogen to which they are attached to form a monocyclic or bicyclic heterocycle with 5-7 members in each ring and optionally containing, in addition to the nitrogen, one or two additional heteroatoms selected from N, O and S, said monocyclic or bicyclic heterocycle optionally substituted with one or more substituents selected from $R^z$;

$R^z$ is selected from: $(C=O)_rO_s(C_1-C_{10})$ alkyl, $O_r(C_1-C_3)$ perfluoroalkyl, $(C_0-C_6)$alkylene-$S(O)_mR^a$, oxo, OH, halo, CN, $(C=O)_rO_s(C_2-C_{10})$ alkenyl, $(C=O)_rO_s(C_2-C_{10})$ alkynyl, $(C=O)_rO_s(C_3-C_6)$ cycloalkyl, $(C=O)_rO_s(C_0-C_6)$ alkylene-aryl, $(C=O)_rO_s(C_0-C_6)$ alkylene-heterocyclyl, $(C=O)_rO_s(C_0-C_6)$ alkylene-$N(R^b)_2$, $C(O)R^a$, $(C_0-C_6)$alkylene-$CO_2R^a$, $C(O)H$, $(C_0-C_6)$alkylene-$CO_2H$, $C(O)N(R^b)_2$, $S(O)_mR^a$, and $S(O)_2N(R^b)_2NR^c(C=O)O_bR^a$, $O(C=O)$ $O_bC_1-C_{10}$ alkyl, $O(C=O)O_bC_3-C_8$ cycloalkyl, $O(C=O)$ $O_b$aryl, and $O(C=O)O_b$-heterocycle, wherein said alkyl, alkenyl, alkynyl, cycloalkyl, aryl, and heterocyclyl are optionally substituted with up to three substituents selected from $R^b$, OH, $(C_1-C_6)$alkoxy, halogen, $CO_2H$, CN, O $(C=O)C_1-C_6$ alkyl, oxo, and $N(R^b)_2$;

$R^a$ is $(C_1-C_6)$alkyl, $(C_3-C_6)$cycloalkyl, aryl or heterocyclyl; and $R^b$ is H, $(C_1-C_6)$alkyl, aryl, heterocyclyl, $(C_3-C_6)$cycloalkyl, $(C=O)OC_1-C_6$ alkyl, $(C=O)C_1-C_6$ alkyl or $S(O)_2R^a$;

$R^c$ is selected from: H, $C_1-C_6$ alkyl, aryl, $C_2-C_6$ alkenyl, $C_2-C_6$ alkynyl, heterocyclyl, $C_3-C_8$ cycloalkyl and $C_1-C_6$perfluoroalkyl, wherein said alkyl, cycloalkyl, aryl, heterocylyl, alkenyl, and alkynyl is optionally substituted with one or more substituents selected from $R^z$;

or a pharmaceutically acceptable salt or a stereoisomer thereof.

Another embodiment includes an allosteric AKT inhibitor having the formula:

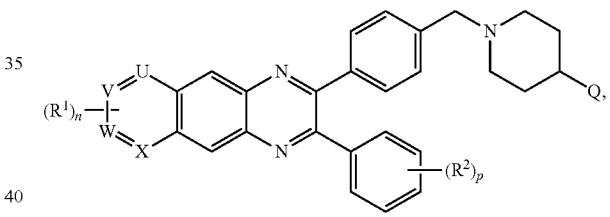

wherein a is 0 or 1; b is 0 or 1; m is 0, 1 or 2; n is 0, 1, 2 or 3; p is 0, 1 or 2; r is 0 or 1; s is 0 or 1; u, v, and x are independently selected from CH and N; W is a bond, CH or N;

Q is selected from: —NR$^5$R$^6$,

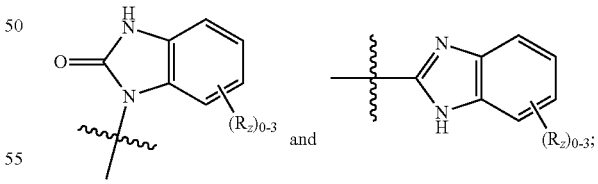

$R^1$ is independently selected from $(C=O)_aO_bC_1-C_6$ alkyl, $(C=O)_aO_b$aryl, $C_2-C_6$ alkenyl, $C_2-C_6$ alkynyl, $(C=O)_aO_b$-heterocyclyl, $(C=O)_aO_bC_3-C_6$ cycloalkyl, $CO_2H$, halogen, CN, OH, $O_bC_1-C_6$perfluoroalkyl, $O_a(C=O)_bNR^7R^8$, $NR^c$ $(C=O)NR^7R^8$, $S(O)_mR^a$, $S(O)_2NR^7R^8$, $NR^cS(O)_mR^a$, oxo, CHO, $NO_2$, $NR^c(C=O)O_bR^a$, $O(C=O)O_bC_1-C_6$ alkyl, $O(C=O)O_bC_3-C_6$ cycloalkyl, $O(C=O)O_b$aryl, and $O(C=O)O_b$-heterocycle, wherein said alkyl, aryl, alkenyl, alkynyl, heterocyclyl, and cycloalkyl are optionally substituted with one or more substituents selected from $R^z$;

$R^2$ is independently selected from $C_1$-$C_6$ alkyl, aryl, heterocyclyl, $CO_2H$, halo, CN, OH and $S(O)_2NR^7R^8$, wherein said alkyl, aryl and heterocyclyl are optionally substituted with one, two or three substituents selected from $R^z$;

$R^7$ and $R^8$ are independently selected from H, (C=O)$O_bC_1$-$C_{10}$ alkyl, (C=O)$O_bC_3$-$C_8$ cycloalkyl, (C=O)$O_b$aryl, (C=O)$O_b$heterocyclyl, $C_1$-$C_{10}$ alkyl, aryl, $C_2$-$C_{10}$ alkenyl, $C_2$-$C_{10}$ alkynyl, heterocyclyl, $C_3$-$C_8$ cycloalkyl, $SO_2R^a$ and (C=O)$NR^b{}_2$, wherein said alkyl, cycloalkyl, aryl, heterocylyl, alkenyl, and alkynyl is optionally substituted with one or more substituents selected from $R^z$, or $R^7$ and $R^8$ can be taken together with the nitrogen to which they are attached to form a monocyclic or bicyclic heterocycle with 5-7 members in each ring and optionally containing, in addition to the nitrogen, one or two additional heteroatoms selected from N, O and S, said monocyclic or bicyclic heterocycle optionally substituted with one or more substituents selected from $R^z$;

$R^z$ is selected from: (C=O)$_rO_s(C_1$-$C_{10})$ alkyl, $O_r(C_1$-$C_3)$ perfluoroalkyl, $(C_0$-$C_6)$alkylene-$S(O)_mR^a$, oxo, OH, halo, CN, (C=O)$_rO_s(C_2$-$C_{10})$ alkenyl, (C=O)$_rO_s(C_2$-$C_{10})$ alkynyl, (C=O)$_rO_s(C_3$-$C_6)$ cycloalkyl, (C=O)$_rO_s(C_0$-$C_6)$ alkylene-aryl, (C=O)$_rO_s(C_0$-$C_6)$ alkylene-heterocyclyl, (C=O)$_rO_s(C_0$-$C_6)$ alkylene-$N(R^b)_2$, $C(O)R^a$, $(C_0$-$C_6)$alkylene-$CO_2R^a$, C(O)H, $(C_0$-$C_6)$alkylene-$CO_2H$, $C(O)N(R^b)_2$, $S(O)_mR^a$, and $S(O)_2N(R^b)_2NR^c(C=O)O_bR^a$, O (C=O)$O_bC_1$-$C_{10}$ alkyl, O(C=O)$O_bC_3$-$C_8$ cycloalkyl, O(C=O)$O_b$aryl, and O(C=O)$O_b$-heterocycle, wherein said alkyl, alkenyl, alkynyl, cycloalkyl, aryl, and heterocyclyl are optionally substituted with up to three substituents selected from $R^b$, OH, $(C_1$-$C_6)$alkoxy, halogen, $CO_2H$, CN, O (C=O)$C_1$-$C_6$ alkyl, oxo, and $N(R^b)_2$;

$R^a$ is $(C_1$-$C_6)$alkyl, $(C_3$-$C_6)$cycloalkyl, aryl or heterocyclyl; and $R^b$ is H, $(C_1$-$C_6)$alkyl, aryl, heterocyclyl, $(C_3$-$C_6)$cycloalkyl, (C=O)$OC_1$-$C_6$ alkyl, (C=O)$C_1$-$C_6$ alkyl or $S(O)_2R^a$;

$R^c$ is selected from: H, $C_1$-$C_6$ alkyl, aryl, $C_2$-$C_6$ alkenyl, $C_2$-$C_6$ alkynyl, heterocyclyl, $C_3$-$C_8$ cycloalkyl and $C_1$-$C_6$perfluoroalkyl, wherein said alkyl, cycloalkyl, aryl, heterocylyl, alkenyl, and alkynyl is optionally substituted with one or more substituents selected from $R^z$;

or a pharmaceutically acceptable salt or a stereoisomer thereof. Another embodimemt includes an allosteric AKT inhibitor selected from:

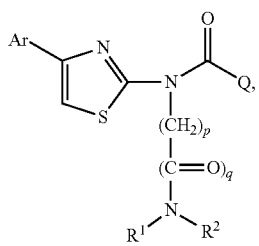

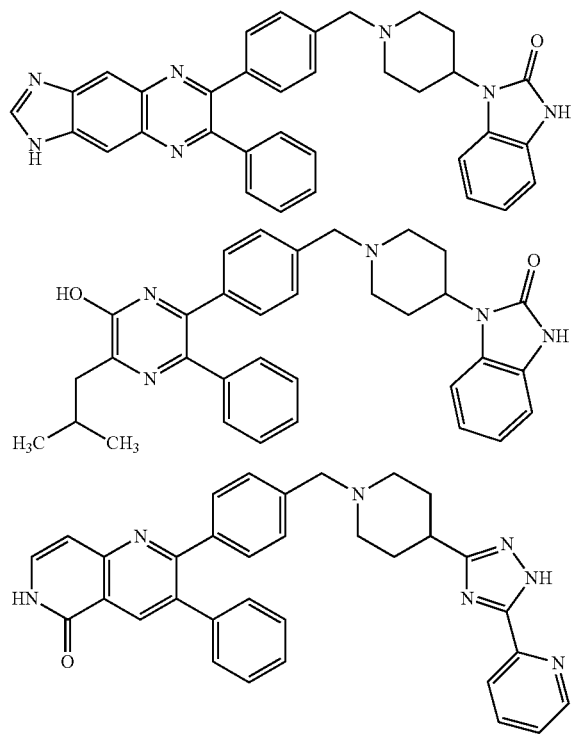

and salts thereof.

In one embodiment, the kinase inhibitor is an AKT-1 selective ATP-competitive inhibitor, and is a compound of Formula IV:

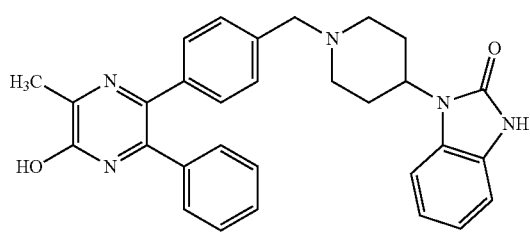

and pharmaceutically acceptable salts thereof, wherein

Ar is selected from aryl, substituted aryl, heteroaryl, and substituted heteroaryl;

Q is selected from cycloalkyl, substituted cycloalkyl, cycloheteroalkyl, substituted cycloheteroalkyl, aryl, substituted aryl, heteroaryl, and substituted heteroaryl;

$R^1$ and $R^2$ are independently selected from hydrogen, alkyl, substituted alkyl, cycloalkyl, substituted cycloalkyl, heterocycloalkyl, substituted heterocycloalkyl, aryl, substituted aryl, heteroaryl, and substituted heteroaryl; or $R^1$ and $R^2$ together with the nitrogen to which $R^1$ and $R_2$ are attached form a ring chosen from cycloheteroalkyl, substituted cycloheteroalkyl, heteroaryl, and substituted heteroaryl;

p is selected from 2, 3, 4, and 5; and q is 0 or 1.

Compounds of Formula IV include:

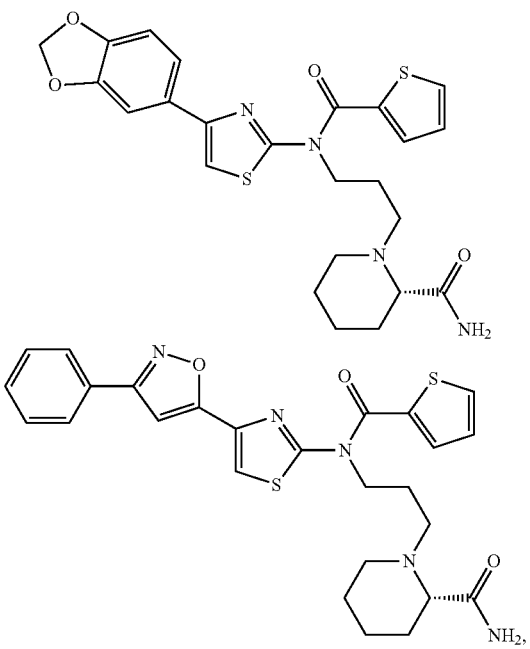

and salts thereof

Another embodiment includes AKT inhibitors such as perifosine having the formula:

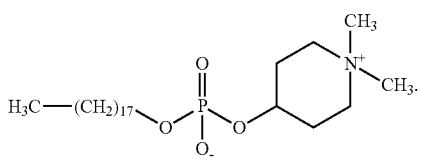

Another embodiment includes AKT inhibitors such as anti-AKT antibodies and anti-AKT DNA or RNA.

Another embodiment includes AKT inhibitors such as oligonucleotides, including antisense oligonucleotides having the sequences: 5' ccagccccaccagtccact 3' (SEQ ID NO: 1), 5' cgccaaggagatcatgcagc 3' (SEQ ID NO: 2), 5' gctgcatgatctccttggcg 3' (SEQ ID NO: 3), 5' agatagctggtgacagacag 3' (SEQ ID NO: 4), 5' cgtggagagatcatctgagg 3' (SEQ ID NO: 5), 5' tcgaaaaggtcaagtgctac 3' (SEQ ID NO: 6), 5' tggtgcagcggcagcggcag 3' (SEQ ID NO: 7) and 5' ggcgcgagcgcgggcctagc 3' (SEQ ID NO: 8).

In one embodiment, the kinase inhibitor is a compound of Formula III. In one example, compounds of Formula III include PI3-k inhibitors. In another example, compounds of Formula III include mTOR inhibitors. Compounds of Formula III have the formula:

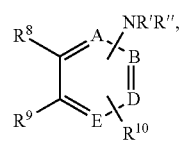

III wherein, A, B, D and E are independently —CH or N;

$R^8$ and $R^9$ are taken together to form a 5 or 6 membered aromatic, heteroaromatic, cyclic or heterocyclic ring, which can be optionally substituted. For example, $R^8$ and $R^9$ can be taken together with the carbons in formula III to which they are attached to form a 9-10 member bicyclic ring system. Embodiments of the bicyclic ring systems include the following structures, wherein

indicates a bond in the formula III ring:

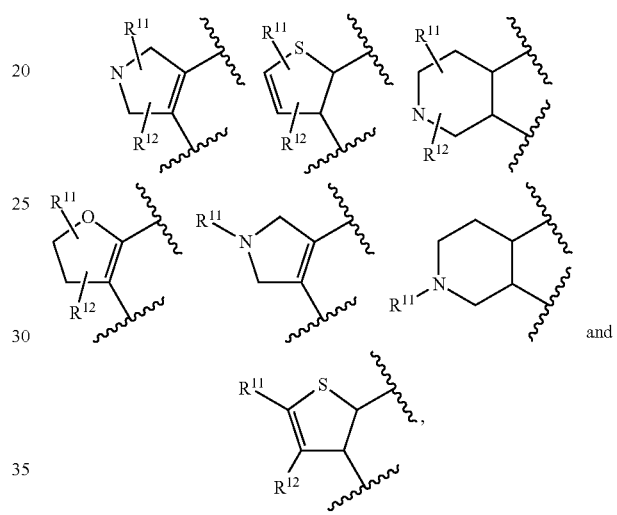

wherein $R^{11}$ and $R^{12}$ are independently selected from the group consisting of hydrogen, halogen, OH, amino, dialkylamino, monoalkylamino, $C_1$-$C_6$-alkyl, —C(=O)O—$(CR^yR^z)_n$-W or phenyl, which is optionally substituted with halogen, OH, $C_1$-$C_3$ alkyl or cyclopropylmethyl, wherein W is $C_{5-12}$ aryl or heteroaryl, $R^y$ and $R^z$ are independently hydrogen, halogen, —OH or $C_{1-6}$ alkyl; or $R^{11}$ and $R^{12}$ are taken together to form a 5-14 membered aromatic or heteroaromatic ring. For example, $R^{11}$ and $R^{12}$ can be taken together with the carbons to which they are attached and the ring in Formula III above to form a 12-14 member tricyclic ring system, and in one embodiment has the following structure:

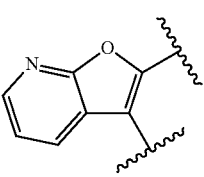 [SMILES: *c1oc2ncccc2c1*]

R' and R" are taken together with the N to which they are bound to form a 5, 6 or 7 member heterocyclic ring, which can be optionally substituted with halogen, OH, amino, dialkylamino, monoalkylamino, $C_1$-$C_6$-alkyl, having one of the following structures, which can further contain the above-listed substituents:

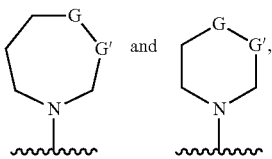

wherein, G and G' are independently C, O or N;
R$^{10}$ is an aromatic or heteroaromatic ring, having the structure:

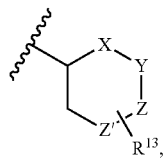

wherein, X, Y, Z and Z' are independently —CH or N;
R$^{13}$ is hydrogen, halogen, OH, amino, dialkylamino, monoalkylamino, C$_1$-C$_6$-alkyl or —N—(C=O)—N—R$^{14}$, wherein R$^{14}$ is C$_1$-C$_6$-alkyl. An example of R$^{10}$ is:

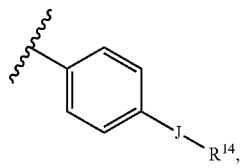

wherein, J is —N—(C=O)—N—, and R$^{14}$ is C$_1$-C$_6$-alkyl.
An example compound of Formula III includes the PI13-k inhibitor:

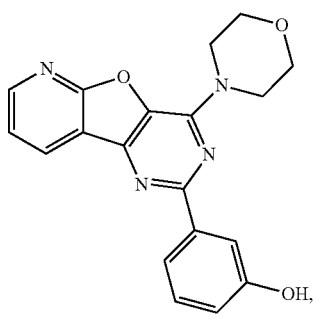

III-5

Another embodiment includes mTOR inhibitors having the following formula:

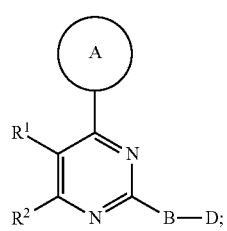

stereoisomers, tautomers or a pharmaceutically acceptable salt thereof, wherein:

A is a ring selected from the group consisting of morpholin-4-yl, 3,4-dihydro-2H-pyran-4-yl, 3,6-dihydro-2H-pyran-4-yl, tetrahydro-2H-pyran-4-yl, 1,4-oxazepan-4-yl, piperidin-1-yl, and is optionally substituted with from 1 to 2 substituents selected from the group consisting of —C(O)OR$^a$, —C(O)NR$^a$R$^b$, —NR$^a$R$^b$, —OR$^a$, —SR$^a$, —S(O)$_2$R$^c$, —S(O)R$^c$, —R$^c$, halogen, —NO$_2$, —CN and —N$_3$, wherein R$^a$ and R$^b$ are each independently selected from hydrogen, C$_{1-6}$ alkyl, C$_{1-6}$ haloalkyl, C$_{2-6}$ alkenyl and C$_{3-6}$ cycloalkyl, or R$^a$ and R$^b$, together with the nitrogen atom to which each is attached, are combined to form a 3- to 6-membered ring, and R$^c$ is selected from C$_{1-6}$ alkyl, C$_{1-6}$ haloalkyl, C$_{2-6}$ alkenyl, C$_{3-6}$ cycloalkyl;

R$^1$ and R$^2$ are combined with the atoms to which they are attached to form an optionally substituted pyrrolidine, piperidine or homopiperidine ring, wherein the nitrogen atom of said pyrrolidine, piperidine or homopiperidine ring is substituted by the group:

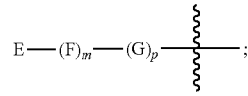

wherein E is hydrogen, C$_{6-10}$ aryl, C$_{5-10}$ heteroaryl, C$_{3-10}$ cycloalkyl, C$_{3-10}$ heterocycloalkyl, C$_{1-6}$ alkyl or C$_{1-6}$ heteroalkyl; and wherein E is optionally substituted with 1 to 5 substituents selected from halogen, C$_{1-6}$ alkyl, —NR$^d$R$^e$, —SR$^d$, —OR$^d$, —C(O)OR$^d$, —C(O)NR$^d$R$^e$, —C(O)R$^d$, —NR$^d$C(O)R$^e$, —OC(O)R$^f$, —NR$^d$C(O)NR$^d$R$^e$, —OC(O)NR$^d$R$^e$, —C(=NOR$^d$)NR$^d$R$^e$, —NR$^d$C(=N—CN)NR$^d$R$^e$, —NR$^d$S(O)$_2$NR$^d$R$^e$, —S(O)$_2$R$^d$, —S(O)$_2$NR$^d$R$^e$, —R$^f$, —NO$_2$, —N$_3$, =O, —CN, —(CH$_2$)$_{1-4}$—NR$^d$R$^e$, —(CH$_2$)$_{1-4}$—SR$^d$, —(CH$_2$)$_{1-4}$—OR$^d$, —(CH$_2$)$_{1-4}$—C(O)OR$^d$, —(CH$_2$)$_{1-4}$—C(O)NR$^d$R$^e$, —(CH$_2$)$_{1-4}$—C(O)R$^d$, —(CH$_2$)$_{1-4}$—NR$^d$C(O)R$^e$, —(CH$_2$)$_{1-4}$—OC(O)R$^f$, —(CH$_2$)$_{1-4}$—NR$^d$C(O)NR$^d$R$^e$, —(CH$_2$)$_{1-4}$—OC(O)NR$^d$R$^e$, —(CH$_2$)$_{1-4}$—C(=NOR$^d$)NR$^d$R$^e$, —(CH$_2$)$_{1-4}$—NR$^d$C(=N—CN)NR$^d$R$^e$, —(CH$_2$)$_{1-4}$—NR$^d$S(O)$_2$NR$^d$R$^e$, —(CH$_2$)$_{1-4}$—S(O)$_2$R$^d$, —(CH$_2$)$_{1-4}$—S(O)$_2$NR$^d$R$^e$, —(CH$_2$)$_{1-4}$—NO$_2$, —(CH$_2$)$_{1-4}$—N$_3$ or —(CH$_2$)$_{1-4}$—CN; wherein R$^d$ and R$^e$ are each independently selected from hydrogen, C$_{1-6}$ alkyl, C$_{1-6}$ haloalkyl, C$_{2-6}$ alkenyl, C$_{2-6}$ alkynyl, C$_{3-7}$ cycloalkyl, C$_{3-7}$ heterocycloalkyl, phenyl and —(CH$_2$)$_{1-4}$-phenyl, or R$^d$ and R$^e$, when attached to the same nitrogen atom are combined to form a 3- to 6-membered ring; R$^f$ is selected from C$_{1-6}$ alkyl, C$_{1-6}$ haloalkyl, C$_{2-6}$ alkenyl, C$_{2-6}$ alkynyl, C$_{3-7}$ cycloalkyl, C$_{3-7}$ heterocycloalkyl, phenyl and —(CH$_2$)$_{1-4}$-phenyl;

F is a member selected from the group consisting of C$_{1-6}$ alkylene, C$_{2-6}$ alkenylene, C$_{2-6}$ alkynylene and C$_{1-6}$ heteroalkylene; wherein F is independently substituted with from 0 to 3 substituents selected from the group consisting of halogen, —NR$^g$R$^h$, —SR$^g$, —OR$^g$, —C(O)OR$^g$, —C(O)NR$^g$R$^h$, —NR$^g$C(O)R$^i$, —OC(O)R$^i$, —NR$^g$C(O)NR$^g$R$^h$, —OC(O)NR$^g$R$^h$, NR$^g$S(O)$_2$NR$^g$R$^h$, —S(O)$_2$R$^g$, —S(O)$_2$NR$^g$R$^h$, —R$^i$, —NO$_2$, N$_3$, =O, —CN, —(CH$_2$)$_{1-4}$—NR$^g$R$^h$, —(CH$_2$)$_{1-4}$—SR$^g$, —(CH$_2$)$_{1-4}$—OR$^g$, —(CH$_2$)$_{1-4}$—C(O)OR$^g$, —(CH$_2$)$_{1-4}$—C(O)NR$^g$R$^h$, —(CH$_2$)$_{1-4}$—C(O)R$^g$, —(CH$_2$)$_{1-4}$—NR$^g$C(O)R$^h$, —(CH$_2$)$_{1-4}$—OC(O)R$^i$, —(CH$_2$)$_{1-4}$—NR$^g$C(O)NR$^g$R$^h$, —(CH$_2$)$_{1-4}$—OC(O)NR$^g$R$^h$, —(CH$_2$)$_{1-4}$—NR$^g$S(O)$_2$NR$^g$R$^h$, —(CH$_2$)$_{1-4}$—S(O)$_2$R$^g$, —(CH$_2$)$_{1-4}$—S(O)$_2$NR$^g$R$^h$, —(CH$_2$)$_{1-4}$—NO$_2$, —(CH$_2$)$_{1-4}$—N$_3$ and —(CH$_2$)$_{1-4}$—CN;

wherein $R^g$ and $R^h$ are each independently selected from hydrogen, $C_{1-6}$ alkyl, $C_{1-6}$ haloalkyl, $C_{1-6}$ heteroalkyl, $C_{3-7}$ cycloalkyl, $C_{3-7}$ heterocycloalkyl, phenyl and —$(CH_2)_{1-4}$-phenyl, and optionally $R^g$ and $R^h$, when attached to the same nitrogen atom are combined to form a 3- to 6-membered ring; $R^i$ is selected from $C_{1-6}$ alkyl, $C_{1-6}$ haloalkyl, $C_{3-7}$ cycloalkyl, $C_{3-7}$ heterocycloalkyl, phenyl and —$(CH_2)_{1-4}$-phenyl;

G is a member selected from the group consisting of —C(O)—, —OC(O)—, —NHC(O)—, —NHC(=NOH)—, —S(O)$_2$— and —NHS(O)$_2$—;

m and p are each independently an integer from 0 to 1, wherein if m and p are both the integer 0, then E is not $C_{1-6}$ alkyl or $C_{1-6}$ heteroalkyl;

wherein pyrrolidine, piperidine or homopiperidine ring formed by combining $R^1$ and $R^2$ is further substituted with from 0 to 5 substituents selected from the group consisting of halogen, —$NR^jR^k$, —$SR^j$, —$OR^j$, —$C(O)OR^j$, —$C(O)NR^jR^k$, —$NHC(O)R^j$, —$OC(O)R^j$, —$R^m$, —CN and =O, wherein $R^j$ and $R^k$ are each independently selected from hydrogen, $C_{1-6}$ alkyl, $C_{1-6}$ haloalkyl, $C_{2-6}$ alkenyl, $C_{2-6}$ alkynyl, $C_{3-5}$ cycloalkyl and $C_{3-5}$ heterocycloalkyl, and $R^j$ and $R^k$, when attached to the same nitrogen atom, are optionally combined to form a 3- to 6-membered ring; and $R^m$ is selected from $C_{1-6}$ alkyl, $C_{1-6}$ haloalkyl, $C_{2-6}$ alkenyl, $C_{2-6}$ alkynyl, $C_{3-5}$ cycloalkyl and $C_{3-5}$ heterocycloalkyl;

B is selected from the group consisting of phenylene, pyridylene, pyrimidylene, pyridazinylene and pyrazinyline and is substituted with from 0 to 4 substituents selected from halogen, —CN, —$N_3$, —$NO_2$, —$C(O)OR^n$, —$C(O)NR^nR_o$, —$NR^nC(O)R^o$, —$NR^nC(O)NR^nR^o$, —$OR^n$, —$NR^nR^o$ and $R^p$; wherein $R^n$ and $R^o$ are independently selected from hydrogen and $C_{1-4}$ alkyl, $C_{1-4}$ haloalkyl, $C_{1-4}$ heteroalkyl, $C_{3-7}$ cycloalkyl and $C_{3-7}$ heterocycloalkyl, or when attached to the same nitrogen atom, $R^n$ and $R^o$ are optionally are combined to form a 3- to 6-membered ring; $R^p$ is $C_{1-4}$ alkyl, $C_{1-4}$ haloalkyl, $C_{3-7}$ cycloalkyl and $C_{3-7}$ heterocycloalkyl, wherein any two substituents, not including the D group, located on adjacent atoms of B are optionally combined to form a 5- to 6-membered carbocyclic, heterocyclic, aryl or heteroaryl ring; and D is a member selected from the group consisting of —$NR^3C(O)NR^4R^5$, —$NR^4R^5$, —$C(O)NR^4R^5$, —$OC(O)OR^4$, —$OC(O)NR^4R^5$, —$NR^3C(=N—CN)NR^4R^5$, —$NR^3C(=N—OR^4)NR^4R^5$, —$NR^3C(=N—NR^4)NR^4R^5$, —$NR^3C(O)R^4$, —$NR^3C(O)OR^4$, —$NR^3S(O)_2NR^4R^5$ and —$NR^3S(O)_2R^4$, wherein $R^3$ is selected from the group consisting of hydrogen, $C_{1-6}$ alkyl, $C_{1-6}$ haloalkyl and $C_{2-6}$ alkenyl; $R^4$ and $R^5$ are each independently selected from the group consisting of hydrogen, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ heterocycloalkyl, $C_{6-10}$ aryl and $C_{5-10}$ heteroaryl, and $R^4$ and $R^5$, when attached to the same nitrogen atom, are optionally combined to form a 5- to 7-membered heterocyclic or heteroaryl ring; and wherein $R^3$, $R^4$ and $R^5$ are further substituted with from 0 to 3 substituents independently selected from the group consisting of halogen, —$NO_2$, —CN, —$NR^qR^r$, —$OR^1$, $SR^q$, —$C(O)OR^q$, —$C(O)NR^qR^r$, —$NR^qC(O)R^r$, —$NR^qC(O)OR^s$, —$(CH_2)_{1-4}$—$NR^qR^r$, —$(CH_2)_{1-4}$—$OR^q$, —$(CH_2)_{1-4}$—$SR^q$, —$(CH_2)_{1-4}$—$C(O)OR^q$, —$(CH_2)_{1-4}$—$C(O)NR^qR^r$, —$(CH_2)_{1-4}$—$NR^qC(O)R^r$, —$(CH_2)_{1-4}$—$NR^qC(O)OR^r$, —$(CH_2)_{1-4}$—CN, —$(CH_2)_{1-4}$—$NO_2$, —$S(O)R^r$, —$S(O)_2R^r$, =O, and —$R^s$; wherein $R^q$ and $R^r$ is selected from hydrogen, $C_{1-6}$ alkyl, $C_{1-6}$ haloalkyl, $C_{2-6}$ alkenyl, $C_{2-6}$ alkynyl, $C_{1-6}$ heteroalkyl, $C_{3-7}$ cycloalkyl, $C_{3-7}$ heterocycloalkyl, $C_{6-10}$ aryl, $C_{5-10}$ heteroaryl; and $R^s$, at each occurrence, is independently selected from $C_{1-6}$ alkyl, $C_{1-6}$ haloalkyl, $C_{1-6}$ heteroalkyl, $C_{3-7}$ cycloalkyl, $C_{3-7}$ heterocycloalkyl, $C_{6-10}$ aryl and $C_{5-10}$ heteroaryl; and wherein the D group and a substituent located on an adjacent atom of the B ring are optionally combined to form a 5- to 6-membered heterocyclic or heteroaryl ring.

In certain embodiments:

A is a ring selected from the group consisting of morpholin-4-yl, 3,4-dihydro-2H-pyran-4-yl, 3,6-dihydro-2H-pyran-4-yl, tetrahydro-2H-pyran-4-yl, 1,4-oxazepan-4-yl, piperidin-1-yl, optionally substituted by $C_1$-$C_6$ alkyl;

B is selected from the group consisting of phenylene and pyrimidylene;

D is —$NR^3C(O)NR^4R^5$, —$NR^4R^5$, —$C(O)NR^4R^5$, —$OC(O)OR^4$, —$OC(O)NR^4R^5$, —$NR^3C(=N—CN)NR^4R^5$, —$NR^3C(=N—OR^4)NR^4R^5$, —$NR^3C(=N—NR^4)NR^4R^5$, —$NR^3C(O)R^4$, —$NR^3C(O)OR^4$, —$NR^3S(O)_2NR^4R^5$ or —$NR^3S(O)_2R^4$, wherein $R^3$ is hydrogen or $C_{1-6}$ alkyl; $R^4$ and $R^5$ are each independently hydrogen, $C_{1-6}$ alkyl, $C_{1-6}$ haloalkyl or $C_{3-10}$ cycloalkyl, or $R^4$ and $R^5$ are combined to form a 5- or 6-membered heterocyclic ring;

$R^1$ and $R^2$ are combined with the atoms to which they are attached to form an substituted pyrrolidine, piperidine or homopiperidine ring, wherein the nitrogen atom of said ring is substituted by the group:

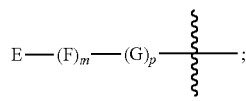

wherein E is hydrogen, $C_6$ aryl, $C_{5-6}$ heteroaryl, $C_{1-6}$ alkyl or $C_{5-6}$ heterocycloalkyl,; and wherein E is optionally substituted with 1 to 5 substituents selected from halogen, $C_{1-6}$ alkyl, —$NR^dR^e$, —$SR^d$, —$OR^d$, —$C(O)OR^d$, —$C(O)NR^dR^e$, —$C(O)R^d$, —$NR^dC(O)R^e$, —$OC(O)R^f$, —$NR^dC(O)NR^dR^e$, —$OC(O)NR^dR^e$, —$C(=NOR^d)NR^dR^e$, —$NR^dC(=N—CN)NR^dR^e$, —$NR^dS(O)_2NR^dR^e$, —$S(O)_2R^d$, —$S(O)_2NR^dR^e$, —$R^f$, —$NO_2$, —$N_3$, =O, —CN, —$(CH_2)_{1-4}$—$NR^dR^e$, —$(CH_2)_{1-4}$—$SR^d$, —$(CH_2)_{1-4}$—$OR^d$, —$(CH_2)_{1-4}$—$C(O)OR^d$, —$(CH_2)_{1-4}$—$C(O)NR^dR^e$, —$(CH_2)_{1-4}$—$C(O)R^d$, —$(CH_2)_{1-4}$—$NR^dC(O)R^e$, —$(CH_2)_{1-4}$—$OC(O)R^f$, —$(CH_2)_{1-4}$—$NR^dC(O)NR^dR^e$, —$(CH_2)_{1-4}$—$OC(O)NR^dR^e$, —$(CH_2)_{1-4}$—$C(=NOR^d)NR^dR^e$, —$(CH_2)_{1-4}$—$NR^dC(=N—CN)NR^dR^e$, —$(CH_2)_{1-4}$—$NR^dS(O)_2NR^dR^e$, —$(CH_2)_{1-4}$—$S(O)_2R^d$, —$(C_2)_{1-4}$—$S(O)_2NR^dR^e$, —$(CH_2)_{1-4}$—$NO_2$, —$(CH_2)_{1-4}$—$N_3$ or —$(CH_2)_{1-4}$—CN; wherein $R^d$ and $R^e$ are each independently selected from hydrogen, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ heterocycloalkyl, phenyl and —$(CH_2)_{1-4}$-phenyl, or $R^d$ and $R^e$, when attached to the same nitrogen atom are combined to form a 3- to 6-membered ring; $R^f$ is selected from $C_{1-6}$ alkyl, $C_{1-6}$ haloalkyl, $C_{3-7}$ cycloalkyl, $C_{3-7}$ heterocycloalkyl, phenyl and —$(CH_2)_{1-4}$-phenyl;

F is $C_{1-6}$ alkylene;

G is —C(O)—, —OC(O)—, —NHC(O)—, —NHC(=NOH)—, —S(O)$_2$—or —NHS(O)$_2$—; and m and p are independently 0 or 1.

Another embodiment includes mTOR inhibitor compounds, including:

79
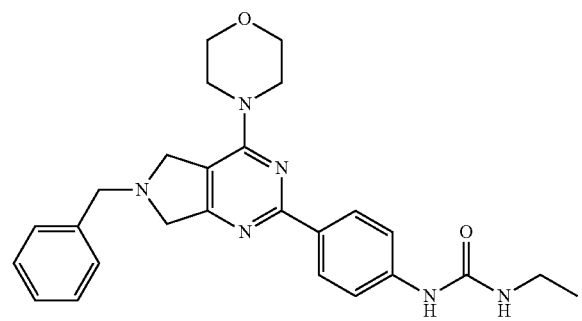
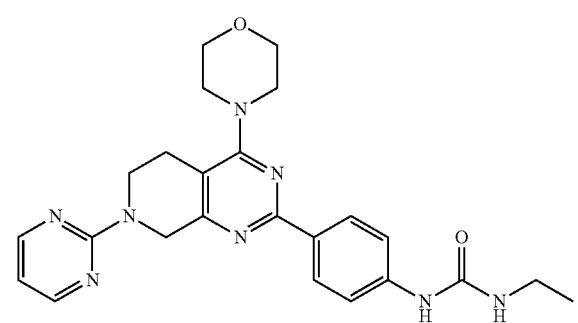
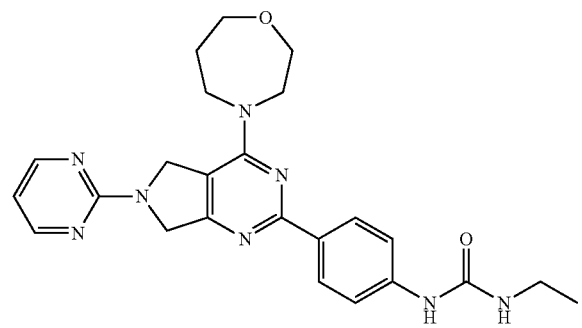
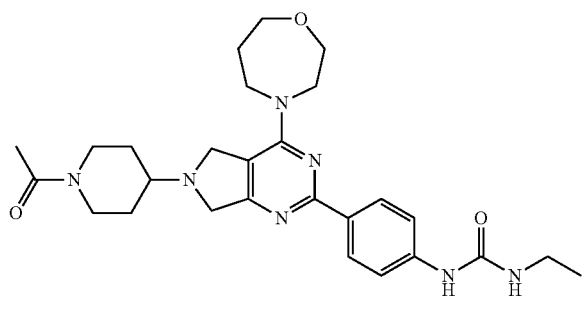
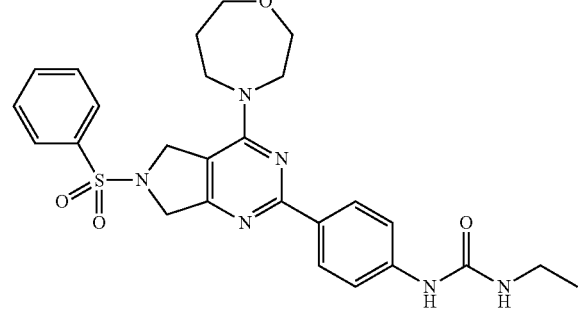
80
-continued
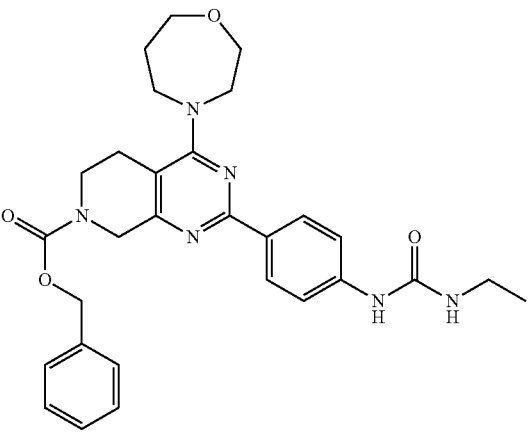
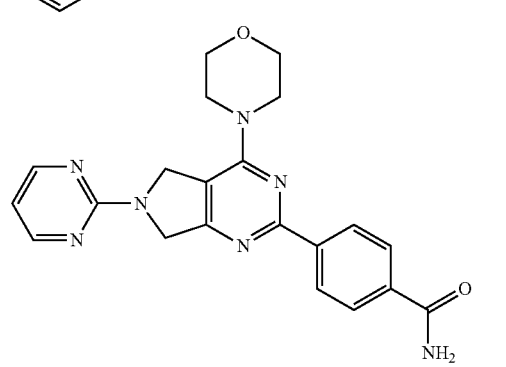
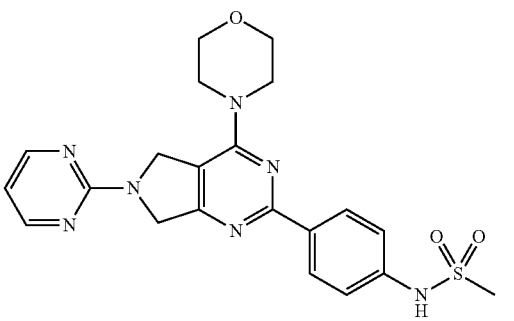
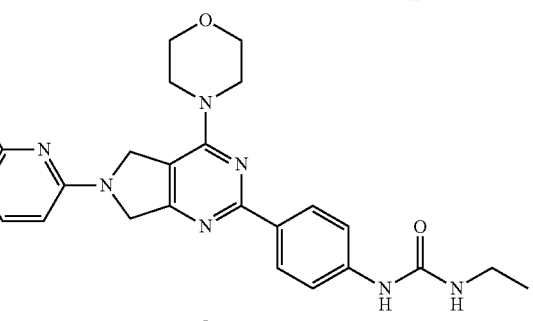
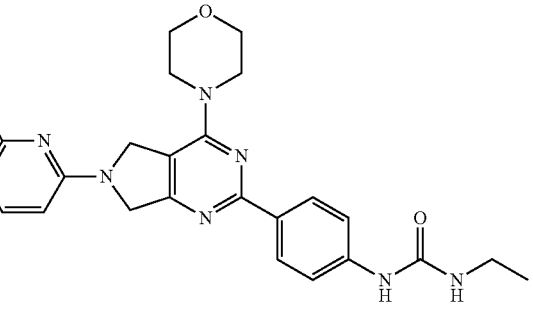

Another embodiment includes the mTOR inhibitor, rapamycin:

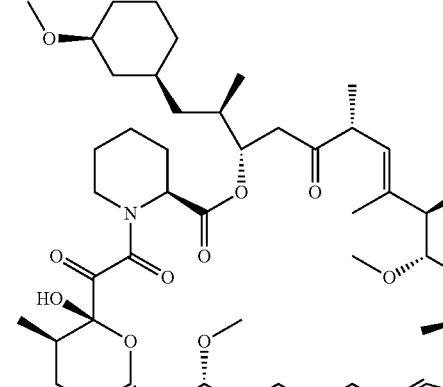

Another embodiment includes PI3-k inhibitor compounds of the following formula:

or pharmaceutically acceptable salts thereof, wherein:

$R^1$ and $R^2$ are independently selected from hydrogen, halogen, $C_{1-6}$ alkyl, $-NR^dR^e$, $-SR^d$, $-OR^d$, $-C(O)OR^d$, $-C(O)NR^dR^e$, $-C(O)R^d$, $-NR^dC(O)R^e$, $-OC(O)R^f$, $-NR^dC(O)NR^dR^e$, $-OC(O)NR^dR^e$, $-C(=NOR^d)NR^dR^e$, $-NR^dC(=N-CN)NR^dR^e$, $-NR^dS(O)_2NR^dR^e$, $-S(O)_2R^d$, $-S(O)_2NR^dR^e$, $-R^f$, $-NO_2$, $-N_3$, $=O$, $-CN$, $-(CH_2)_{1-4}-NR^dR^e$, $-(CH_2)_{1-4}-SR^d$, $-(CH_2)_{1-4}-OR^d$, $-(CH_2)_{1-4}-C(O)OR^d$, $-(CH_2)_{1-4}-C(O)NR^dR^e$, $-(CH_2)_{1-4}-C(O)R^d$, $-(CH_2)_{1-4}-NR^dC(O)R^e$, $-(CH_2)_{1-4}OC(O)R^f$, $-(CH_2)_{1-4}-NR^dC(O)NR^dR^e$, $-(CH_2)_{1-4}OC(O)NR^dR^e$, $-(CH_2)_{1-4}C(=NOR^d)NR^dR^e$, $-(CH_2)_{1-4}-NR^dC(=N-CN)NR^dR^e$, $-(CH_2)_{1-4}-NR^dS(O)_2NR^dR^e$, $-(CH_2)_{1-4}-S(O)_2R^d$, $-(CH_2)_{1-4}-S(O)_2R^dR^e$, $-(CH_2)_{1-4}-NO_2$, $-(CH_2)_{1-4}N_3$ or $-(CH_2)_{1-4}-CN$; wherein $R^d$ and $R^e$ are each independently selected from hydrogen, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ heterocycloalkyl, phenyl and $-(CH_2)_{1-4}$-phenyl, or $R^d$ and $R^e$, when attached to the same nitrogen atom are combined to form a 3- to 6-membered ring; $R^f$ is selected from $C_{1-6}$ alkyl, $C_{1-6}$ haloalkyl, $C_{3-7}$ cycloalkyl, $C_{3-7}$ heterocycloalkyl, phenyl and $-(CH_2)_{1-4}$-phenyl; or $R^1$ and $R^2$ are taken together with the atoms to which they are attached to form a fused 5- or 6- membered heterocyclyl or heteroaryl ring, optionally substituted by oxo, halogen, $C_1$-$C_3$ alkyl or $CF_3$.

Example PI3-k inhibitors include the following:
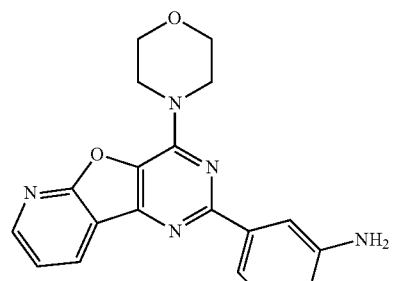
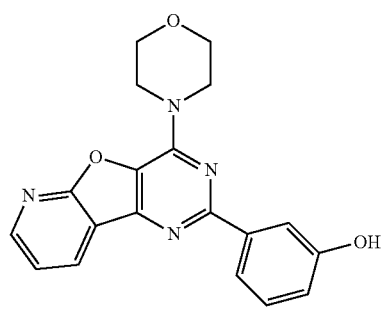
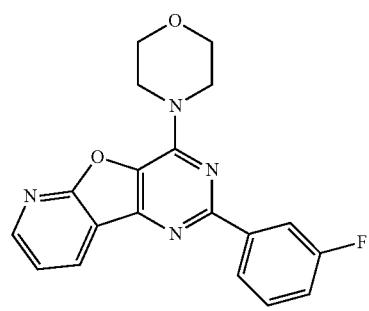
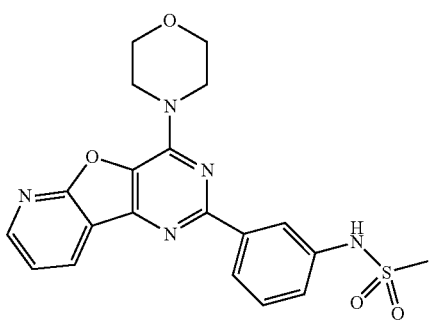
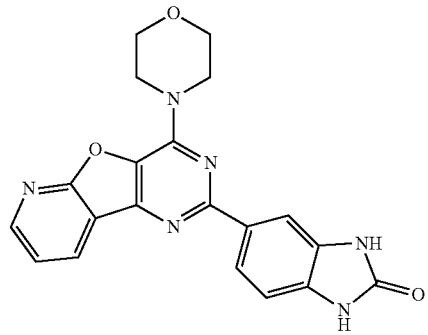
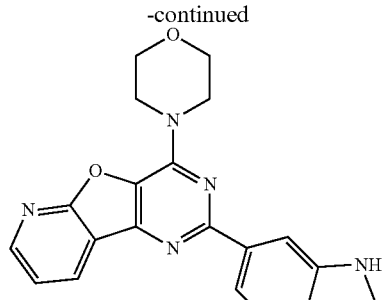
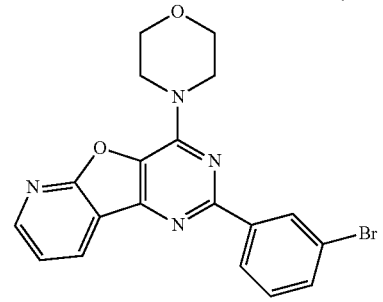
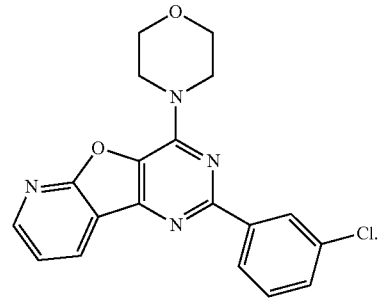
In one embodiment, the kinase inhibitor is a PI3K kinase inhibitor of Formulas V and VI:
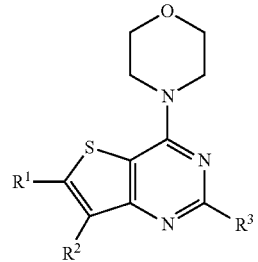
V
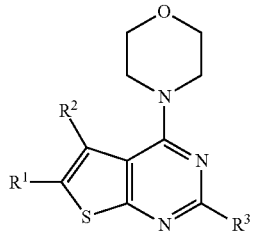
VI
or stereoisomers, geometric isomers, tautomers, or pharmaceutically acceptable salts thereof, where:
$R^1$ is selected from H, F, Cl, Br, I, CN, —$(CR^{14}R^{15})_m NR^{10}R^{11}$, —$C(R^{14}R^{15})_n NR^{12}C(=Y)R^{10}$, —$(CR^{14}$ $R^{15})_n NR^{12}S(O)_2 R^{10}$, —$(CR^{14}R^{15})_m OR^{10}$, —$(CR^{14}R^{15})_n S(O)_2 R^{10}$, —$(CR^{14}R^{15})_n S(O)_2 NR^{10}R^{11}$, —$C(OR^{10})R^{11}R^{14}$, —$C(=Y)R^{10}$, —$C(=Y)OR^{10}$, —$C(=Y)NR^{10}R^{11}$, —$C(=Y)NR^{12}OR^{10}$, —$C(=O)NR^{12}S(O)_2 R^{10}$, —$C(=O)NR^{12}(CR^{14}R^{15})_m NR^{10}R^{11}$, —$NO_2$, —$NR^{12}C(=Y)R^{11}$, —$NR^{12}C(=Y)OR^{11}$, —$NR^{12}C(=Y)NR^{10}R^{11}$, —$NR^{12}S(O)_2 R^{10}$, —$NR^{12}SO_2 NR^{10}R^{11}$, —$SR^{10}$, —$S(O)_2 R^{10}$, —$S(O)_2 NR^{10}R^{11}$, —$SC(=Y)R^{10}$, —$SC(=Y)OR^{10}$, $C_1$-$C_{12}$ alkyl, $C_2$-$C_8$ alkenyl, $C_2$-$C_8$ alkynyl, $C_3 C_{12}$ carbocyclyl, $C_2$-$C_{20}$ heterocyclyl, $C_6$-$C_{20}$ aryl, and $C_1$-$C_{20}$ heteroaryl;

$R^2$ is selected from H, F, Cl, Br, I, CN, $CF_3$, —$NO_2$, —$C(=Y)R^{10}$, —$C(=Y)OR^{10}$, —$C(=Y)NR^{10}R^{11}$, —$(CR^{14}R^{15})_m NR^{10}R^{11}$, —$(CR^{14}R^{15})_n OR^{10}$, —$(CR^{14}R^{15})_t NR^{12}C(=O)(CR^{14}R^{15})NR^{10}R^{11}$, —$NR^{12}C(=Y)R^{10}$, —$NR^{12}C(=Y)OR^{10}$, —$NR^{12}C(=Y)NR^{10}R^{11}$, —$NR^{12}SO_2 R^{10}$, $OR^{10}$, —$OC(=Y)R^{10}$, —$OC(=Y)OR^{10}$, —$OC(=Y)NR^{10}R^{11}$, —$OS(O)_2(OR^{10})$, —$OP(=Y)(OR^{10})(OR^{11})$, —$OP(OR^{10})(OR^{11})$, $SR^{10}$, —$S(O)R^{10}$, —$S(O)_2 R^{10}$, —$S(O)_2 NR^{10}R^{11}$, —$S(O)(OR^{10})$ —$S(O)_2(OR10)$, —$SC(=Y)R^{10}$—$SC(=Y)OR^{10}$, —$SC(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl;

$R^3$ is a carbon linked monocyclic heteroaryl, a carbon linked fused bicyclic $C_3$-$C_{20}$ heterocyclyl, or a carbon linked fused bicyclic $C_1$-$C_{20}$ heteroaryl, where the monocyclic heteroaryl, fused bicyclic $C_3$-$C_{20}$ heterocyclyl, and fused bicyclic $C_1$-$C_{20}$ heteroaryl are optionally substituted with one or more groups selected from F, Cl, Br, I, —CN, —$NR^{10}R^{11}$, $OR_{10}$, —$C(O)R^{10}$, —$NR^{10}C(O)R^{11}$, —$N(C(O)R^{11}$, —$N(C(O)R^{11})_2$, —$NR^{10}C(O)NR^{10}R^{11}$, —$NR^{12}S(O)_2 R^{10}$, —$C(=O)OR^{10}$, —$C(=O)NR^{10}R^{11}$, $C_1$-$C_{12}$ alkyl and ($C_1$-$C_{12}$ alkyl)—$OR^{10}$;

$R^{10} R^{11}$ and $R^{12}$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, or $R^{10}$ and $R^{11}$ together with the nitrogen to which they are attached form a $C_2$-$C_{20}$ heterocyclic ring optionally substituted with one or more groups independently selected from oxo, $(CH_2)_m OR^{12}$, $NR^{12}R^{12}$, $CF_3$, F, Cl, Br, I, $SO_2 R^{12}$, $C(=O)R^{12}$, $NR^{12}C(=Y)R^{12}$, $NR^{12}S(O)_2 R^{12}$, $C(=Y)NR^{12}R^{12}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl and $C_1$-$C_{20}$ heteroaryl;

$R^{14}$ and $R^{15}$ are independently selected from H, $C_1$-$C_{12}$ alkyl, or —$(CH_2)_n$-aryl, or $R^{14}$ and $R^{15}$ together with the atoms to which they are attached form a saturated or partially unsaturated $C_3$-$C_{12}$ carbocyclic ring; where said alkyl, alkenyl, alkynyl, carbocyclyl, heterocyclyl, aryl, and heteroaryl, are optionally substituted with one or more groups independently selected from F, Cl, Br, I, CN, $CF_3$, —$NO_2$, oxo, $R^{10}$, —$C(=Y)R^{10}$, —$C(=Y)R^{10}$, —$C(=Y)OR^{10}$, —$C(=Y)NR^{10}R^{11}$, —$(CR^{14}R^{15})_n NR^{10}R^{11}$, —$(CR^{14}R^{15})_n OR^{10}$, —$NR^{10}R^{11}$, —$NR^{12}C(=Y)R^{10}$, —$NR^{12}C(=Y)OR^{11}$, —$NR^{12}C(=Y)NR^{10}R^{11}$, —$(CR^{14}R^{15})_m NR^{12}SO_2 R^{10}$, =$NR^{12}$, $OR^{10}$, —$OC(=Y)R^{10}$, —$OC(=Y)OR^{10}$, —$OC(=Y)NR^{10}R^{11}$, —$OS(O)_2(OR^{10})$, —$OP(=Y)(OR^{10})(OR^{11})$, —$OP(OR^{10})(OR^{11})$, —$SR^{10}$, —$S(O)R^{10}$, —$S(O)_2 R^{10}$, —$S(O)_2 NR^{10}R^{11}$, —$S(O)(OR^{10})$, —$S(O)_2(OR^{10})$, —$SC(=Y)R^{10}$, —$SC(=Y)OR^{10}$, —$SC(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl;

Y is O, S, or $NR^{12}$;

m is 0, 1, 2, 3, 4, 5 or 6; and n is 1, 2, 3, 4, 5 or 6.

Example PI3-k inhibitors include the following:

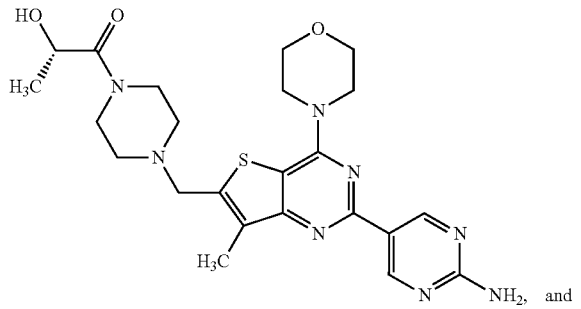

III-3

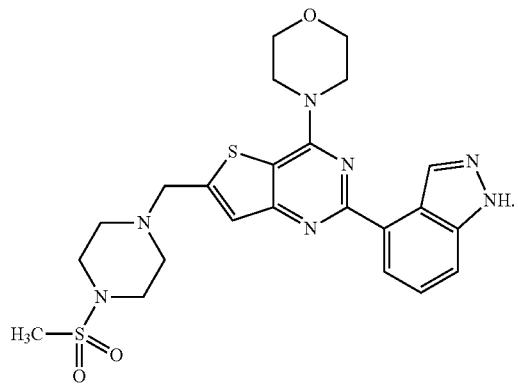

III-6

Preparation of Formulae V and VI Compounds

The Formula V and VI compounds may be synthesized by synthetic routes that include processes analogous to those well-known in the chemical arts, and including WO 2006/046031, which is incorporated herein by reference in its entirety, for all purposes. Starting materials are generally available from commercial sources such as Aldrich Chemicals (Milwaukee, WI) or are readily prepared using methods well known to those skilled in the art (e.g., prepared by methods generally described in Louis F. Fieser and Mary Fieser, Reagents for Organic Synthesis, v. 1-19, Wiley, N.Y. (1967-1999 ed.), or Beilsteins Handbuch der organischen Chemie, 4, Aufl. ed. Springer-Verlag, Berlin, including supplements (also available via the Beilstein online database).

Formulae V and VI compound may be prepared using procedures to prepare other thiophenes, furans, pyrimidines (U.S. Pat. Nos. 6,608,053; 6,492,383; 6,232,320; 6,187,777; 3,763,156; 3,661,908; 3,475,429; 5,075,305; US 2003/220365; GB 1393161; WO 93/13664); and other heterocycles, which are described in: Comprehensive Heterocyclic Chemistry, Editors Katritzky and Rees, Pergamon Press, 1984.

Formulae V and VI compounds may be converted into a pharmaceutically acceptable salt, and a salt may be converted into the free compound, by conventional methods. Examples of pharmaceutically acceptable salts include salts with inorganic acids such as hydrochloric acid, hydrobromic acid, hydroiodic acid, sulphuric acid, nitric acid and phosphoric acid; and organic acids such as methanesulfonic acid, benzenesulphonic acid, formic acid, acetic acid, trifluoroacetic acid, propionic acid, oxalic acid, malonic acid, succinic acid, fumaric acid, maleic acid, lactic acid, malic acid, tartaric acid, citric acid, ethanesulfonic acid, aspartic acid and glutamic acid. The salt may be a mesylate, a hydrochloride, a phosphate, a benzenesulphonate or a sulphate. Salts may be mono-salts or bis-salts. For example, the mesylate salt may be the mono-mesylate or the bis-mesylate.

Formulae V and VI compounds and salts may also exist as hydrates or solvates.

Protection of functional groups (e.g., primary or secondary amine) of intermediates may be necessary in preparing Formulae V and VI compounds. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

For illustrative purposes, Schemes 5-11 show general methods for preparing the compounds as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Scheme 5 shows a general method for preparation of the thienopyrimidine intermediates 55 and 56 from 2-carboxyester, 3-amino thiophene, and 2-amino, 3-carboxy ester thiophene reagents, respectively 51 and 52, wherein Hal is Cl, Br, or I; and $R^1$, $R^2$, and $R^{10}$ are as defined for Formulae V and VI compounds, or precursors or prodrugs thereto.

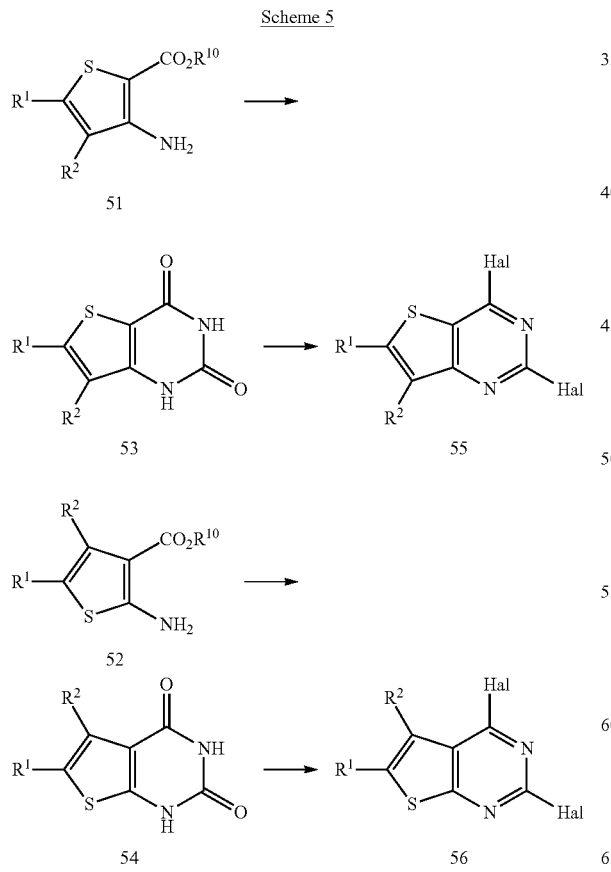

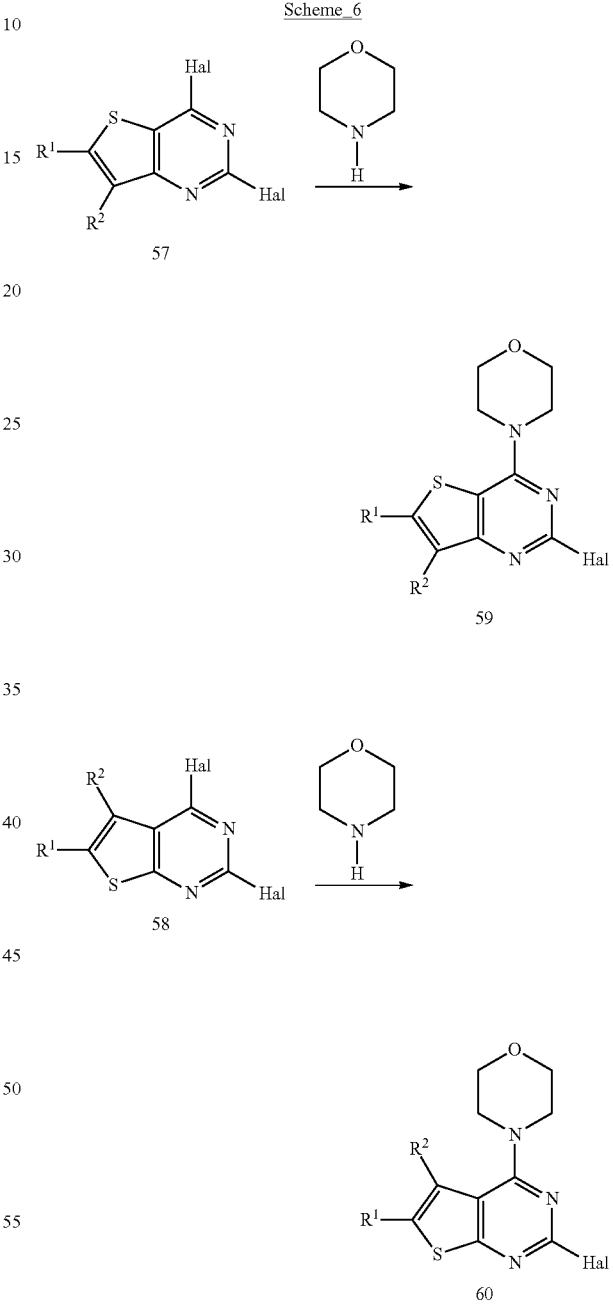

Scheme 6 shows a general method for selectively displacing a 4-halide from bis-halo thienopyrimidine intermediates 57 and 58 with morpholine under basic conditions in an organic solvent to prepare 2-halo, 4-morpholino thienopyrimidine compounds 59 and 60 respectively, wherein Hal is Cl, Br, or I; and $R^1$ and $R^2$ are as defined for Formulae V and VI compounds, or precursors or prodrugs thereto.

Scheme 7

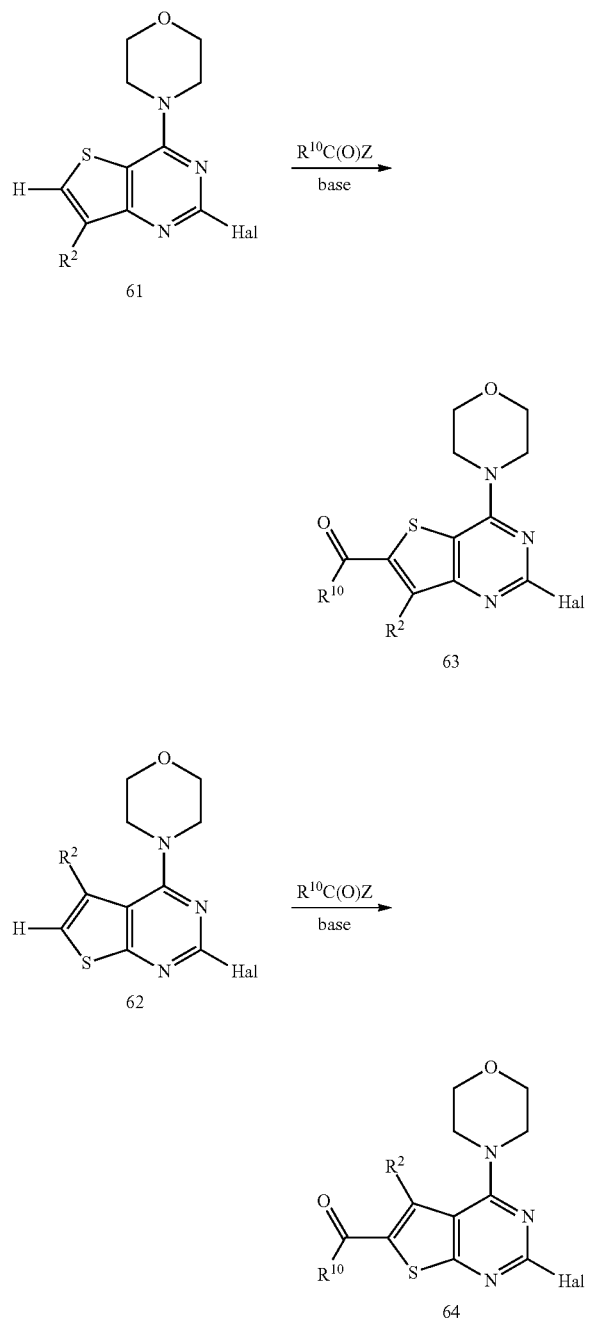

Scheme 8

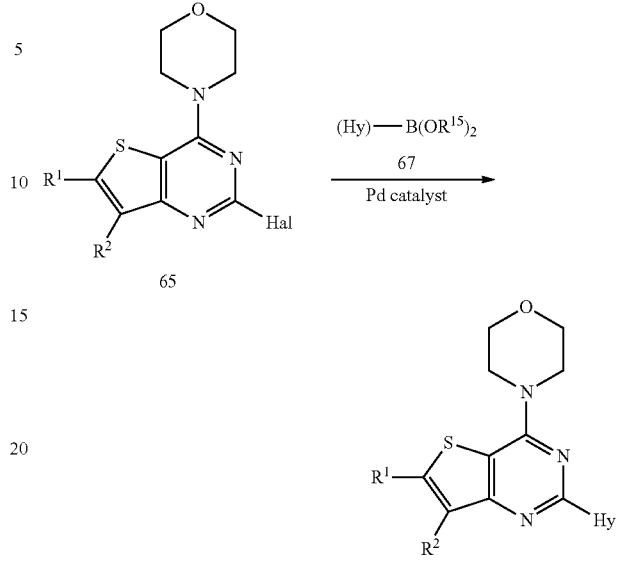

Scheme 7 shows a general method for derivatizing the 6-position of 2-halo, 4-morpholino, 6-hydrogen thienopyrimidine compounds 61 and 62 where $R^1$ is H. Treating 61 or 62 with a lithiating reagent to remove the 6 position proton, followed by adding an acylating reagent $R^{10}C(O)Z$ where Z is a leaving group, such as halide, NHS ester, carboxylate, or dialkylamino, gives 2-halo, 4-morpholino, 6-acyl thienopyrimidine compounds 63 and 64, wherein Hal is Cl, Br, or I; and $R^2$ and $R^{10}$ are as defined for Formulae V and VI compounds, or precursors or prodrugs thereto. An example of $R^{10}C(O)Z$ to prepare 6-formyl compounds ($R^1$=H) is N,N'-dimethylformamide (DMF).

Scheme 8 shows a general method for Suzuki-type coupling of a 2-halo pyrimidine intermediate (65 and 66) with a monocyclic heteroaryl, fused bicyclic heterocyclyl or fused bicyclic heteroaryl boronate acid ($R^{15}$=H) or ester ($R^{15}$=alkyl) reagent 67 to prepare the 2-substituted (Hy), 4-morpholino thienopyrimidine compounds (68 and 69) of Formulae V and VI wherein Hal is Cl, Br, or I; and $R^1$ and $R^2$ are as defined for Formulae V and VI compounds, or precursors or prodrugs thereto. For reviews of the Suzuki reaction, see: Miyaura et al. (1995) Chem. Rev. 95:2457-2483; Suzuki, A. (1999) J. Organomet. Chem. 576:147-168; Suzuki, A. in Metal-Catalyzed Cross-Coupling Reactions, Diederich, F., Stang, P. J., Eds., VCH, Weinheim, D E (1998), pp 49-97. The palladium catalyst may be any that is typically used for Suzuki-type cross-couplings, such as $PdCl_2(PPh_3)_2$, $Pd(PPh_3)_4$, $Pd(OAc)_2$, $PdCl_2(dppf)$-DCM, $Pd_2(dba)_3$/Pt-Bu$)_3$ (Owens et al (2003) Bioorganic & Med. Chem. Letters 13:4143-4145; Molander et al (2002) Organic Letters 4(11):1867-1870; U.S. Pat. No. 6,448,433).

Scheme 9

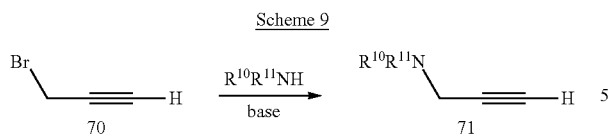

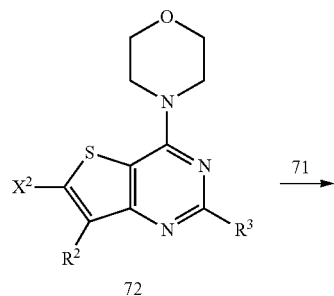

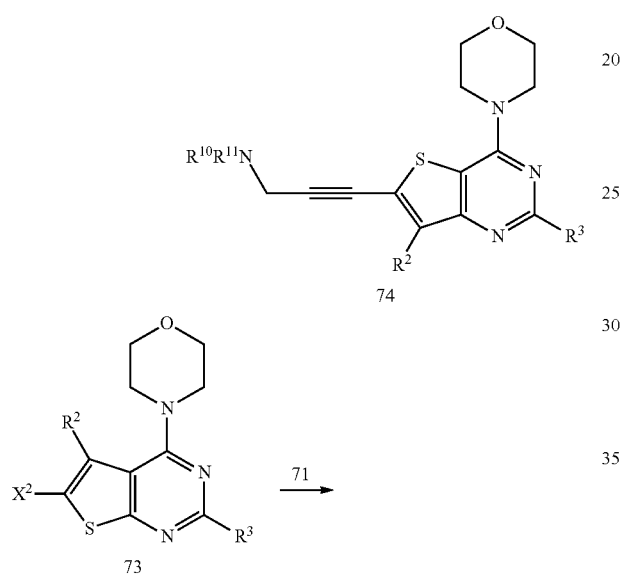

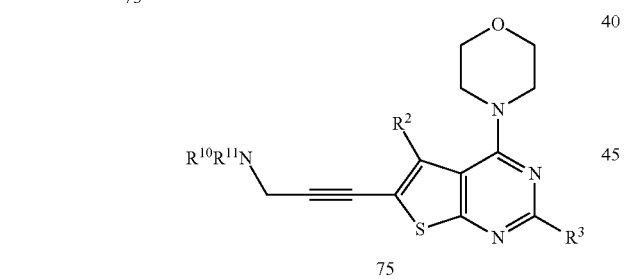

Scheme 9 shows a general method for the synthesis of alkynes 71, which can be used to prepare alkynylated derivatives of compounds 72 and 73. Propargylic amines 71 may be prepared by reaction of propargyl bromide 70 with an amine of the formula $R^{10}R^{11}NH$ (wherein $R^{10}$ and $R^{11}$ are independently selected from H, alkyl, aryl and heteroaryl, or $R^{10}$ and $R^{11}$ together with the nitrogen to which they are attached form a heterocyclic ring) in the presence of an appropriate base ($Cs_2CO_3$ or the like). For reviews of alkynyl amines and related syntheses see Booker-Milburn, K. I., *Comprehensive Organic Functional Group Transformations* (1995), 2:1039-1074; and Viehe, H. G., (1967) Angew. Chem., Int. Ed. Eng., 6(9):767-778. Alkynes 71 may subsequently be reacted with intermediates 72 ($X^2$=bromo or iodo) or 73 (via Sonogashira coupling), to provide compounds 74 and 75, respectively, wherein $R^2$ and $R^3$ are as defined for Formulae V and VI compounds, or precursors or prodrugs thereto.

Scheme 10

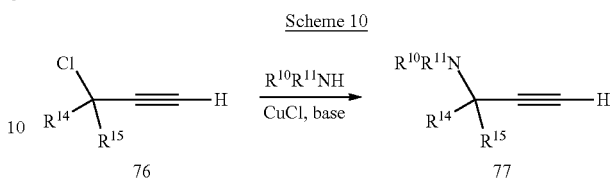

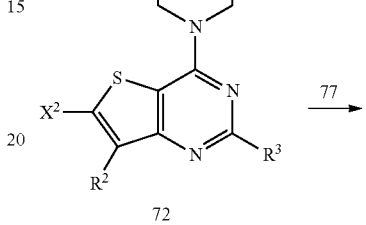

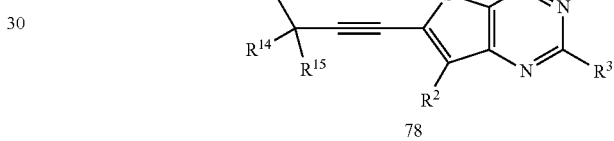

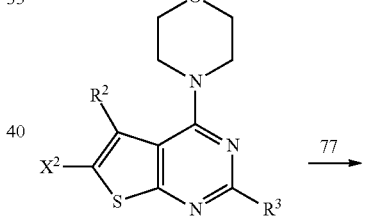

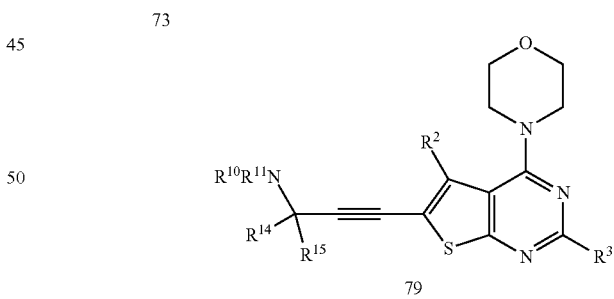

Scheme 10 shows a general method for the synthesis of alkynes 77, which can be used to prepare alkynylated derivatives of compounds 72 and 73. Gem-dialkyl propargylic amines 77 may be prepared using methods described by Zaragoza et al (2004) J. Med. Chem., 47:2833. According to Scheme 6, gem-dialkyl chloride 76 ($R^{14}$ and $R^{15}$ are independently methyl, ethyl or other alkyl group) can be reacted with an amine of the formula $R^{10}R^{11}NH$ (wherein $R^{10}$ and $R^{11}$ are independently selected from H, alkyl, aryl and heteroaryl, or $R^{10}$ and $R^{11}$ together with the nitrogen to which they are attached form a heterocyclic ring) in the presence of CuCl and an appropriate base (e.g. TEA or the like) to provide the alkyne 77. Alkyne 77 can be reacted with intermediates 72 or 73 (via Sonogashira coupling) to provide compounds 78 and 79, respectively, wherein $R^2$ and $R^3$ are as defined for Formulae V and VI compounds, or precursors or prodrugs thereto.

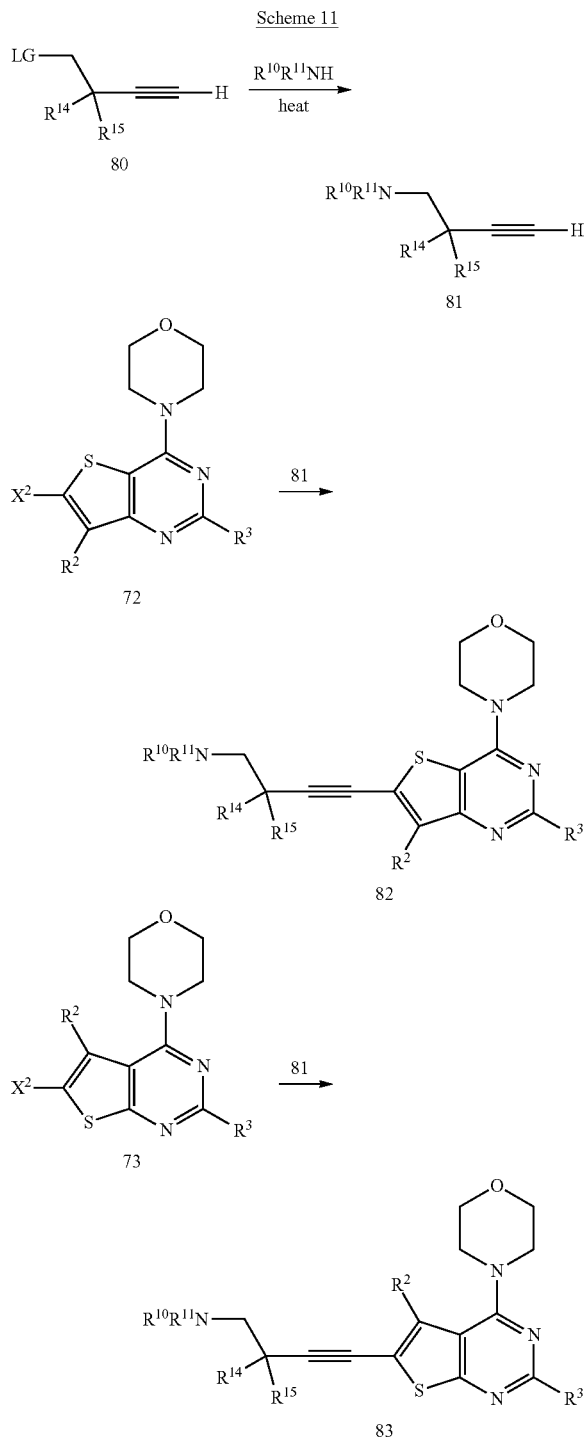

Scheme 11

Scheme 11 shows a general scheme for the synthesis of alkynes 81, which can be used to prepare alkynylated derivatives of compounds 72 and 73. But-3-yn-1-amines 81 (wherein $R^{14}$ and $R^{15}$ are independently H, alkyl, aryl, heteroaryl, or $R^{14}$ and $R^{15}$ together with the carbon atom to which they are attached form a carbocyclic or heterocyclic ring) can be prepared from reaction of alkynes 80 (LG=tosylate or other leaving group) with an amine of the formula $R^{10}R^{11}NH$ (wherein $R^{10}$ and $R^{11}$ are independently selected from H, alkyl, aryl and heteroaryl, or $R^{10}$ and $R^{11}$ together with the nitrogen to which they are attached form a heterocyclic ring) using the protocol described by Olomucki M. et al (1960) Ann. Chim. 5:845. Alkynes 81 can subsequently be reacted with intermediates 72 or 73 (via Sonogashira coupling), according to the descriptions provided for Schemes 5 and 6 to provide compounds 82 and 83, respectively, wherein $R^2$ and $R^3$ are as defined for Formulae V and VI compounds, or precursors or prodrugs thereto.

In the process as defined above, both the amination step and the Pd-mediated cross-coupling step take place under conventional conditions. The palladium catalyst may be any that is typically used for Suzuki-type cross-couplings, such as $PdCl_2(PPh_3)_2$. The reducing agent is typically a borohydride, such as $NaBH(OAc)_3$, $NaBH_4$ or $NaCNBH_4$.

Methods of blocking or reducing relapse tumor growth or a relapse cancer cell growth are also provided. In certain embodiments, the subject was, or is concurrently undergoing cancer therapy. The administration of further treatments, agents, or the combination therapy described herein blocks or reduces relapse tumor growth or relapse cancer cell growth.

RNA Constructs

In another embodiment, the subject matter disclosed herein relates to RNAi constructs described herein. The RNAi constructs are useful inhibitors of Akt.

Pharmaceutical Formulations

The bulk composition and each individual dosage unit can contain fixed amounts of the aforesaid pharmaceutically active agents. The bulk composition is material that has not yet been formed into individual dosage units. An illustrative dosage unit is an oral dosage unit such as tablets, pills, capsules, and the like. Similarly, the herein-described method of treating a patient by administering a pharmaceutical composition is also intended to encompass the administration of the bulk composition and individual dosage units.

Pharmaceutical compositions also embrace isotopically-labeled compounds which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds, and their uses. Exemplary isotopes that can be incorporated into compounds include isotopes of hydrogen, carbon, nitrogen, oxygen, phosphorus, sulfur, fluorine, chlorine and iodine, such as $^2H$, 3H, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically-labeled compounds (e.g., those labeled with $^3H$ and $^{14}C$) are useful in compound and/or substrate tissue distribution assays. Tritiated ($^3H$) and carbon-14 ($^{14}C$) isotopes are useful for their ease of preparation and detectability. Further, substitution with heavier isotopes such as deuterium ($^2H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds can generally be prepared by following procedures analogous to those disclosed in the Schemes and/or in the Examples herein below, by substituting an isotopically labeled reagent for a non-isotopically labeled reagent.

Another aspect provides a pharmaceutical composition comprising a compound disclosed herein in association with one or more pharmaceutically acceptable carrier, glidant, diluent, or excipient.

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound or pharmaceutical composition thereof) or aid in the manufacturing of the pharmaceutical product (i.e., medicament).

The formulations may be prepared using conventional dissolution and mixing procedures. For example, the bulk drug substance (i.e., compound or stabilized form of the compound (e.g., complex with a cyclodextrin derivative or other known complexation agent) is dissolved in a suitable solvent in the presence of one or more of the excipients described above. The compound is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds may be prepared for various routes and types of administration. For example, a compound described herein, having the desired degree of purity may optionally be mixed with pharmaceutically acceptable diluents, carriers, excipients or stabilizers (Remington's Pharmaceutical Sciences (1995) 18th edition, Mack Publ. Co., Easton, Pa.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8.

The pharmaceutical formulation is preferably sterile. In particular, formulations to be used for in vivo administration must be sterile. Such sterilization is readily accomplished by filtration through sterile filtration membranes.

The pharmaceutical formulation ordinarily can be stored as a solid composition, a lyophilized formulation or as an aqueous solution.

The pharmaceutical formulations will be dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of the compound described herein, administered orally or parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 18th edition, (1995) Mack Publ. Co., Easton, Pa.

Sustained-release preparations of the compounds described herein, may be prepared. Suitable examples of sustained-release preparations include semipermeable matrices of solid hydrophobic polymers containing a compound, which matrices are in the form of shaped articles, e.g., films, or microcapsules. Examples of sustained-release matrices include polyesters, hydrogels (for example, poly (2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D (−) 3-hydroxybutyric acid.

The pharmaceutical formulations include those suitable for the administration routes detailed herein. The formulations may conveniently be presented in unit dosage form and may be prepared by any of the methods well known in the art of pharmacy. Techniques and formulations generally are found in Remington's Pharmaceutical Sciences $18^{th}$ Ed. (1995) Mack Publishing Co., Easton, Pa. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of compounds described herein suitable for oral administration may be prepared as discrete units such as pills, hard or soft e.g., gelatin capsules, cachets, troches, lozenges, aqueous or oil suspensions, dispersible powders or granules, emulsions, syrups or elixirs each containing a predetermined amount of a compound described herein. Such formulations may be prepared according to any method known to the art for the manufacture of pharmaceutical compositions and such compositions may contain one or more agents including sweetening agents, flavoring agents, coloring agents and preserving agents, in order to provide a palatable preparation. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablet excipients of a pharmaceutical formulation may include: Filler (or diluent) to increase the bulk volume of the powdered drug making up the tablet; Disintegrants to encourage the tablet to break down into small fragments, ideally individual drug particles, when it is ingested and promote the rapid dissolution and absorption of drug; Binder to ensure that granules and tablets can be formed with the required mechanical strength and hold a tablet together after it has been compressed, preventing it from breaking down into its component powders during packaging, shipping and routine handling; Glidant to improve the flowability of the powder making up the tablet during production; Lubricant to ensure that the tableting powder does not adhere to the equipment used to press the tablet during manufacture. They improve the flow of the powder mixes through the presses and minimize friction and breakage as the finished tablets are ejected from the equipment; Antiadherent with function similar to that of the glidant, reducing adhesion between the powder making up the tablet and the machine that is used to punch out the shape of the tablet during manufacture; Flavor incorporated into tablets to give them a more pleasant taste or to mask an unpleasant one, and Colorant to aid identification and patient compliance.

Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions may be constituted from known ingredients in a known manner, including a mixture of at least one emulsifier with a fat or an oil, or with both a fat and an oil. Preferably, a hydrophilic emulsifier is included together with a lipophilic emulsifier which acts as a stabilizer. Together, the emulsifier(s) with or without stabilizer(s) make up an emulsifying wax, and the wax together with the oil and fat comprise an emulsifying ointment base which forms the oily dispersed phase of cream formulations. Emulsifiers and emulsion stabilizers suitable for use in the formulation include Tween® 60, Span® 80, cetostearyl alcohol, benzyl alcohol, myristyl alcohol, glyceryl mono-stearate and sodium lauryl sulfate.

Aqueous suspensions of the pharmaceutical formulations contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may be a solution or a suspension in a non-toxic parenterally acceptable diluent or solvent, such as a solution in 1,3-butanediol or prepared from a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

Another aspect provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other treatments described herein.

The compounds may be administered by any route appropriate to the condition to be treated. Suitable routes include oral, parenteral (including subcutaneous, intramuscular, intravenous, intraarterial, inhalation, intradermal, intrathecal, epidural, and infusion techniques), transdermal, rectal, nasal, topical (including buccal and sublingual), vaginal, intraperitoneal, intrapulmonary and intranasal. Topical administration can also involve the use of transdermal administration such as transdermal patches or iontophoresis devices. Formulation of drugs is discussed in Remington's Pharmaceutical Sciences, 18$^{th}$ Ed., (1995) Mack Publishing Co., Easton, Pa. Other examples of drug formulations can be found in Liberman, H. A. and Lachman, L., Eds., Pharmaceutical Dosage Forms, Marcel Decker, Vol 3, 2$^{nd}$ Ed., New York, N.Y. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier, glidant, or excipient. Where the compound is administered parenterally, it may be formulated with a pharmaceutically acceptable parenteral vehicle or diluent, and in a unit dosage injectable form, as detailed below.

A dose to treat human patients may range from about 10 mg to about 1000 mg of a compound. A typical dose may be about 100 mg to about 300 mg of the compound. A dose may be administered once a day (QID), twice per day (BID), or more frequently, depending on the pharmacokinetic (PK) and pharmacodynamic (PD) properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Articles of Manufacture

In another embodiment, an article of manufacture, or "kit", containing compounds useful for the treatment of the diseases and disorders described above is provided. In one embodiment, the kit comprises a container comprising a compound. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound or a formulation thereof which is effective for treating the condition and may have a sterile access port (for example, the container may be an intravenous solution bag or a vial having a stopper pierceable by a hypodermic injection needle). At least one active agent in the composition is a compound described herein. The label or package insert indicates that the composition is used for treating the condition of choice, such as cancer. In one embodiment, the label or package inserts indicates that the composition comprising a compound described herein, can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In another embodiment, the kits are suitable for the delivery of solid oral forms of a compound described herein, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound described herein, contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Responsiveness of a patient can be assessed using any endpoint indicating a benefit to the patient, including, without limitation, (1) inhibition, to some extent, of disease progression, including slowing down and complete arrest; (2) reduction in lesion size; (3) inhibition (i.e., reduction, slowing down or complete stopping) of disease cell infiltration into adjacent peripheral organs and/or tissues; (4) inhibition (i.e. reduction, slowing down or complete stopping) of disease spread; (5) relief, to some extent, of one or more symptoms associated with the disorder; (6) increase in the length of disease-free presentation following treatment; and/or (8) decreased mortality at a given point of time following treatment.

Clinical benefit can be measured by assessing various endpoints, e g , inhibition, to some extent, of disease progression, including slowing down and complete arrest; reduction in the number of disease episodes and/or symptoms; reduction in lesion size; inhibition (i.e., reduction, slowing down or complete stopping) of disease cell infiltration into adjacent peripheral organs and/or tissues; inhibition (i.e. reduction, slowing down or complete stopping) of disease spread; decrease of auto-immune response, which may, but does not have to, result in the regression or ablation of the disease lesion; relief, to some extent, of one or more symptoms associated with the disorder; increase in the length of disease-free presentation following treatment, e.g., progression-free survival; increased overall survival; higher response rate; and/or decreased mortality at a given point of time following treatment.

The term "benefit" is used in the broadest sense and refers to any desirable effect and specifically includes clinical benefit as defined herein.

Administration "in combination with" one or more further therapeutic agents includes simultaneous (concurrent) and/or consecutive administration in any order.

The term "concurrently" is used herein to refer to administration of two or more therapeutic agents, where at least part of the administration overlaps in time. Accordingly, concurrent administration includes a dosing regimen when the administration of one or more agent(s) continues after discontinuing the administration of one or more other agent(s).

It has been determined that certain combinations provide improved effects against certain cancer phenotypes, in one embodiment that have developed resistance to AKT inhibitors. For example, certain combinations provide improved effects against cancers associated with PTEN mutation, AKT mutation (e.g. overexpression or amplification), PI3K mutation, or Her2/ErbB2 amplification or mutation. Accordingly, certain combinations described herein may be particularly useful against these types of cancers, in one embodiment when the cancer develops resistance to AKT inhibitors.

PTEN status may be measured by any suitable means as is known in the art. In one example, IHC is used. Alternatively, Western blot analysis can be used. Antibodies to PTEN are commercially available (Cell Signaling Technology, Beverly, Mass., Cascade Biosciences, Winchester, Mass.). Example procedures for IHC and Western blot analysis for PTEN status are described in Neshat, M. S. et al. Enhanced sensitivity of PTEN-deficient tumors to inhibition of FRAP/mTOR, *Proc. Natl Acad. Sci. USA* 98, 10314-10319 (2001) and Perren, A., et. al. Immunohistochemical Evidence of Loss of PTEN Expression in Primary Ductal Adenocarcinomas of the Breast, *American Journal of Pathology*, Vol. 155, No. 4, October 1999. Additionally, cancers associated with AKT mutation, PI3K mutation, and with Her2/ErbB2 amplification or mutation can be identified using techniques that are known in the art. In one example, PTEN status of a patient or tissue sample is determined using IHC, and a histo score or HScore is assigned to the sample or patient. An example way of calculating HScore uses the formula: HScore= (% 1+cells×1)+(% 2+cells×2)+(% 3+cells×3) (See Shoman, N, et. al, Mod Path (2005) 18, 250-259). A mean PTEN HScore of non-cancerous tissue from the same patient or a collection of patients can be used to determine whether patient or sample HScores are low or null. In one example, HScores of less than about 200 are considered low and correspond to PTEN low, and HScores of about 0 are considered null.

A sample comprising a target gene or biomarker can be obtained by methods well known in the art, and that are appropriate for the particular type and location of the cancer of interest. See under Definitions. For instance, samples of cancerous lesions may be obtained by resection, bronchoscopy, fine needle aspiration, bronchial brushings, or from sputum, pleural fluid or blood. Genes or gene products can be detected from cancer or tumor tissue or from other body samples such as urine, sputum, serum or plasma. The same techniques discussed above for detection of target genes or gene products in cancerous samples can be applied to other body samples. Cancer cells may be sloughed off from cancer lesions and appear in such body samples. By screening such body samples, a simple early diagnosis can be achieved for these cancers. In addition, the progress of therapy can be monitored more easily by testing such body samples for target genes or gene products.

Means for enriching a tissue preparation for cancer cells are known in the art. For example, the tissue may be isolated from paraffin or cryostat sections. Cancer cells may also be separated from normal cells by flow cytometry or laser capture microdissection. These, as well as other techniques for separating cancerous from normal cells, are well known in the art. If the cancer tissue is highly contaminated with normal cells, detection of signature gene or protein expression profile may be more difficult, although techniques for minimizing contamination and/or false positive/negative results are known, some of which are described herein below. For example, a sample may also be assessed for the presence of a biomarker known to be associated with a cancer cell of interest but not a corresponding normal cell, or vice versa.

In certain embodiments, the expression of proteins in a sample is examined using immunohistochemistry ("IHC") and staining protocols. Immunohistochemical staining of tissue sections has been shown to be a reliable method of assessing or detecting presence of proteins in a sample. Immunohistochemistry techniques utilize an antibody to probe and visualize cellular antigens in situ, generally by chromogenic or fluorescent methods.

The tissue sample may be fixed (i.e. preserved) by conventional methodology (See e.g., "Manual of Histological Staining Method of the Armed Forces Institute of Pathology," 3$^{rd}$ edition (1960) Lee G. Luna, H T (ASCP) Editor, The Blakston Division McGraw-Hill Book Company, New York; *The Armed Forces Institute of Pathology Advanced Laboratory Methods in Histology and Pathology* (1994) Ulreka V. Mikel, Editor, Armed Forces Institute of Pathology, American Registry of Pathology, Washington, D.C.).

One of skill in the art will appreciate that the choice of a fixative is determined by the purpose for which the sample is to be histologically stained or otherwise analyzed. One of skill in the art will also appreciate that the length of fixation depends upon the size of the tissue sample and the fixative used. By way of example, neutral buffered formalin, Bouin's or paraformaldehyde, may be used to fix a sample.

Generally, the sample is first fixed and is then dehydrated through an ascending series of alcohols, infiltrated and embedded with paraffin or other sectioning media so that the tissue sample may be sectioned. Alternatively, one may section the tissue and fix the sections obtained. By way of example, the tissue sample may be embedded and processed in paraffin by conventional methodology (See e.g., "Manual of Histological Staining Method of the Armed Forces Institute of Pathology", supra). Examples of paraffin that may be used include, but are not limited to, Paraplast, Broloid, and Tissuemay. Once the tissue sample is embedded, the sample may be sectioned by a microtome or the like (See e.g., "Manual of Histological Staining Method of the Armed Forces Institute of Pathology", supra). By way of example for this procedure, sections may range from about three microns to about five microns in thickness. Once sectioned, the sections may be attached to slides by several standard methods. Examples of slide adhesives include, but are not limited to, silane, gelatin, poly-L-lysine and the like. By way of example, the paraffin embedded sections may be attached to positively charged slides and/or slides coated with poly-L-lysine.

If paraffin has been used as the embedding material, the tissue sections are generally deparaffinized and rehydrated to water. The tissue sections may be deparaffinized by several conventional standard methodologies. For example, xylenes and a gradually descending series of alcohols may be used (See e.g., "Manual of Histological Staining Method of the Armed Forces Institute of Pathology", supra). Alternatively, commercially available deparaffinizing non-organic agents such as Hemo-De7 (CMS, Houston, Tex.) may be used.

In certain embodiments, subsequent to the sample preparation, a tissue section may be analyzed using IHC. IHC may be performed in combination with additional techniques such as morphological staining and/or fluorescence in-situ hybridization. Two general methods of IHC are available; direct and indirect assays. According to the first assay, binding of antibody to the target antigen is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for immunohistochemistry typically will be labeled with a detectable moiety. Numerous labels are available which can be generally grouped into the following categories:

(a) Radioisotopes, such as $^{35}S$, $^{14}C$, $^{125}I$, $^{3}H$ and $^{131}I$. The antibody can be labeled with the radioisotope using the techniques described in *Current Protocols in Immunology*, Volumes 1 and 2, Coligen et al., Ed. Wiley-Interscience, New York, N.Y., Pubs. (1991) for example and radioactivity can be measured using scintillation counting.

(b) Colloidal gold particles.

(c) Fluorescent labels including, but are not limited to, rare earth chelates (europium chelates), Texas Red, rhodamine, fluorescein, dansyl, Lissamine, umbelliferone, phycocrytherin, phycocyanin, or commercially available fluorophores such SPECTRUM ORANGE7 and SPECTRUM GREEN7 and/or derivatives of any one or more of the above. The fluorescent labels can be conjugated to the antibody using the techniques disclosed in *Current Protocols in Immunology*, supra, for example. Fluorescence can be quantified using a fluorimeter.

(d) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, 13-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym.* (ed. J. Langone & H. Van Vunakis), Academic press, New York, 73:147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate (e.g., 4-methylumbelliferyl-β-D-galactosidase).

Numerous other enzyme-substrate combinations are available to those skilled in the art. For a general review of these, see U.S. Pat. Nos. 4,275,149 and 4,318,980. Sometimes, the label is indirectly conjugated with the antibody. The skilled artisan will be aware of various techniques for achieving this. For example, the antibody can be conjugated with biotin and any of the four broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten and one of the different types of labels mentioned above is conjugated with an anti-hapten antibody. Thus, indirect conjugation of the label with the antibody can be achieved.

Aside from the sample preparation procedures discussed above, further treatment of the tissue section prior to, during or following IHC may be desired. For example, epitope retrieval methods, such as heating the tissue sample in citrate buffer may be carried out (see, e.g., Leong et al. *Appl. Immunohistochem.* 4(3):201 (1996)).

Following an optional blocking step, the tissue section is exposed to primary antibody for a sufficient period of time and under suitable conditions such that the primary antibody binds to the target protein antigen in the tissue sample. Appropriate conditions for achieving this can be determined by routine experimentation. The extent of binding of antibody to the sample is determined by using any one of the detectable labels discussed above. In certain embodiments, the label is an enzymatic label (e.g. HRPO) which catalyzes a chemical alteration of the chromogenic substrate such as 3,3'-diaminobenzidine chromogen. In one embodiment, the enzymatic label is conjugated to antibody which binds specifically to the primary antibody (e.g. the primary antibody is rabbit polyclonal antibody and secondary antibody is goat anti-rabbit antibody).

Specimens thus prepared may be mounted and coverslipped. Slide evaluation is then determined, e.g., using a microscope, and staining intensity criteria, routinely used in the art, may be employed. Staining intensity criteria may be evaluated as follows:

TABLE 1

| Staining Pattern | Score |
| --- | --- |
| No staining is observed in cells. | 0 |
| Faint/barely perceptible staining is detected in more than 10% of the cells. | 1+ |
| Weak to moderate staining is observed in more than 10% of the cells. | 2+ |
| Moderate to strong staining is observed in more than 10% of the cells. | 3+ |

In some embodiments, a staining pattern score of about 1+ or higher is diagnostic and/or prognostic. In certain embodiments, a staining pattern score of about 2+ or higher in an IHC assay is diagnostic and/or prognostic. In other embodiments, a staining pattern score of about 3 or higher is diagnostic and/or prognostic. In one embodiment, it is understood that when cells and/or tissue from a tumor or colon adenoma are examined using IHC, staining is generally determined or assessed in tumor cell and/or tissue (as opposed to stromal or surrounding tissue that may be present in the sample).

In alternative methods, the sample may be contacted with an antibody specific for said biomarker under conditions sufficient for an antibody-biomarker complex to form, and then detecting said complex. The presence of the biomarker may be detected in a number of ways, such as by Western blotting and ELISA procedures for assaying a wide variety of tissues and samples, including plasma or serum. A wide range of immunoassay techniques using such an assay format are available, see, e.g., U.S. Pat. Nos. 4,016,043, 4,424,279 and 4,018,653. These include both single-site and two-site or "sandwich" assays of the non-competitive types, as well as in the traditional competitive binding assays. These assays also include direct binding of a labeled antibody to a target biomarker.

Sandwich assays are among the most useful and commonly used assays. Briefly, in a typical forward assay, an unlabeled antibody is immobilized on a solid substrate, and the sample to be tested brought into contact with the bound molecule. After a suitable period of incubation, for a period of time sufficient to allow formation of an antibody-antigen complex, a second antibody specific to the antigen, labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of biomarker.

Variations on the forward assay include a simultaneous assay, in which both sample and labeled antibody are added simultaneously to the bound antibody. These techniques are well known to those skilled in the art, including any minor variations as will be readily apparent. In a typical forward sandwich assay, a first antibody having specificity for the biomarker is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or overnight if more convenient) and under suitable conditions (e.g. from room temperature to 40° C. such as between 25° C. and 32° C. inclusive) to allow binding of any subunit present in the antibody. Following the incubation period, the antibody subunit solid phase is washed and dried and incubated with a second antibody specific for a portion of the biomarker. The second antibody is linked to a reporter molecule which is used to indicate the binding of the second antibody to the molecular marker.

An alternative method involves immobilizing the target biomarkers in the sample and then exposing the immobilized target to specific antibody which may or may not be labeled with a reporter molecule. Depending on the amount of target and the strength of the reporter molecule signal, a bound target may be detectable by direct labeling with the antibody. Alternatively, a second labeled antibody, specific to the first antibody is exposed to the target-first antibody complex to form a target-first antibody-second antibody tertiary complex. The complex is detected by the signal emitted by the reporter molecule. By "reporter molecule", as used in the present specification, is meant a molecule which, by its chemical nature, provides an analytically identifiable signal which allows the detection of antigen-bound antibody. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, -galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of biomarker which was present in the sample. Alternately, fluorescent compounds, such as fluorescein and rhodamine, may be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic color visually detectable with a light microscope. As in the EIA, the fluorescent labeled antibody is allowed to bind to the first antibody-molecular marker complex. After washing off the unbound reagent, the remaining tertiary complex is then exposed to the light of the appropriate wavelength, the fluorescence observed indicates the presence of the molecular marker of interest. Immunofluorescence and EIA techniques are both very well established in the art. However, other reporter molecules, such as radioisotope, chemiluminescent or bioluminescent molecules, may also be employed.

It is contemplated that the above described techniques may also be employed to detect expression of one or more of the target genes.

Methods further include protocols which examine the presence and/or expression of mRNAs of the one ore more target genes in a tissue or cell sample. Methods for the evaluation of mRNAs in cells are well known and include, for example, hybridization assays using complementary DNA probes (such as in situ hybridization using labeled riboprobes specific for the one or more genes, including, but not limited to, S100A9, S100A9, Tie-1, Tie-2, CD31, CD34, VEGFR1, VEGFR2, PDGFC, IL-1β, P1GF, HGF, IL-6, and LIF, Northern blot and related techniques) and various nucleic acid amplification assays (such as RT-PCR using complementary primers specific for one or more of the genes, and other amplification type detection methods, such as, for example, branched DNA, SISBA, TMA and the like).

Tissue or cell samples from mammals can be conveniently assayed for mRNAs using Northern, dot blot or PCR analysis. For example, RT-PCR assays such as quantitative PCR assays are well known in the art. In an illustrative embodiment, a method for detecting a target mRNA in a biological sample comprises producing cDNA from the sample by reverse transcription using at least one primer; amplifying the cDNA so produced using a target polynucleotide as sense and antisense primers to amplify target cDNAs therein; and detecting the presence of the amplified target cDNA. In addition, such methods can include one or more steps that allow one to determine the levels of target mRNA in a biological sample (e.g., by simultaneously examining the levels a comparative control mRNA sequence of a "housekeeping" gene such as an actin family member). Optionally, the sequence of the amplified target cDNA can be determined.

Optional methods include protocols which examine or detect mRNAs, such as target mRNAs, in a tissue or cell sample by microarray technologies. Using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes whose expression correlate with detection of a mutation in AKT or PRAS40 may be arrayed on a solid support. Hybridization of a labeled probe with a particular array member indicates that the sample from which the probe was derived expresses that gene. Differential gene expression analysis of disease tissue can provide valuable information. Microarray technology utilizes nucleic acid hybridization techniques and computing technology to evaluate the mRNA expression profile of thousands of genes within a single experiment. (see, e.g., WO 01/75166 published Oct. 11, 2001; (see, for example, U.S. Pat. Nos. 5,700,637, 5,445,934, and 5,807,522, Lockart, *Nature Biotechnology*, 14:1675-1680 (1996); Cheung, V. G. et al., *Nature Genetics* 21(Suppl):15-19 (1999) for a discussion of array fabrication). DNA microarrays are miniature arrays containing gene fragments that are either synthesized directly onto or spotted onto glass or other substrates. Thousands of genes are usually represented in a single array. A typical microarray experiment involves the following steps: 1) preparation of fluorescently labeled target from RNA isolated from the sample, 2) hybridization of the labeled target to the microarray, 3) washing, staining, and scanning of the array, 4) analysis of the scanned image and 5) generation of gene expression profiles. Currently two main types of DNA microarrays are being used: oligonucleotide (usually 25 to 70 mers) arrays and gene expression arrays containing PCR products prepared from cDNAs. In forming an array, oligonucleotides can be either prefabricated and spotted to the surface or directly synthesized on to the surface (in situ).

The Affymetrix GeneChip® system is a commercially available microarray system which comprises arrays fabricated by direct synthesis of oligonucleotides on a glass surface. Probe/Gene Arrays: Oligonucleotides, usually 25 mers, are directly synthesized onto a glass wafer by a combination of semiconductor-based photolithography and solid phase chemical synthesis technologies. Each array contains up to 400,000 different oligos and each oligo is present in millions of copies. Since oligonucleotide probes are synthesized in known locations on the array, the hybridization patterns and signal intensities can be interpreted in terms of gene identity and relative expression levels by the Affymetrix Microarray Suite software. Each gene is represented on the array by a series of different oligonucleotide probes. Each probe pair consists of a perfect match oligonucleotide and a mismatch oligonucleotide. The perfect match probe has a sequence exactly complimentary to the particular gene and thus measures the expression of the gene. The mismatch probe differs from the perfect match probe by a single base substitution at the center base position, disturbing the binding of the target gene transcript. This helps to determine the background and nonspecific hybridization that contributes to the signal measured for the perfect match oligo. The Microarray Suite software subtracts the hybridization intensities of the mismatch probes from those of the perfect match probes to determine the absolute or specific intensity value for each probe set. Probes are chosen based on current information from Genbank and other nucleotide repositories. The sequences are believed to recognize unique regions of the 3' end of the gene. A GeneChip Hybridization Oven ("rotisserie" oven) is used to carry out the hybridization of up to 64 arrays at one time. The fluidics station performs washing and staining of the probe arrays. It is completely automated and contains four modules, with each module holding one probe array. Each module is controlled independently through Microarray Suite software using preprogrammed fluidics protocols. The scanner is a confocal laser fluorescence scanner which measures fluorescence intensity emitted by the labeled cRNA bound to the probe arrays. The computer workstation with Microarray Suite software controls the fluidics station and the scanner. Microarray Suite software can control up to eight fluidics stations using preprogrammed hybridization, wash, and stain protocols for the probe array. The software also acquires and converts hybridization intensity data into a presence/absence call for each gene using appropriate algorithms. Finally, the software detects changes in gene expression between experiments by comparison analysis and formats the output into .txt files, which can be used with other software programs for further data analysis.

Expression of a selected gene or biomarker in a tissue or cell sample may also be examined by way of functional or activity-based assays. For instance, if the biomarker is an enzyme, one may conduct assays known in the art to determine or detect the presence of the given enzymatic activity in the tissue or cell sample.

EXAMPLES

It is understood that the examples and embodiments described herein are for illustrative purposes only and that various modifications or changes in light thereof will be suggested to persons skilled in the art and are to be included within the spirit and purview of this application and scope of the appended claims.

In Vitro Cell Proliferation Assays

The in vitro potency of the combinations of the compound of Example 2 with certain specific chemotherapeutic agents was measured using the CellTiterGlo® Luminescent Cell Viability Assay, commercially available from Promega Corp., Madison, Wis. This homogeneous assay method is based on the recombinant expression of *Coleoptera* luciferase (U.S. Pat. Nos. 5,583,024; 5,674,713; 5,700,670) and determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Glo® Assay was conducted in 96 or 384 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The CellTiterGlo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay can be used with various multiwell formats, e.g. 96 or 384 well format. Data can be recorded by luminometer or CCD camera imaging device. The luminescence output is presented as relative light units (RLU), measured over time.

I claim:

1. A method of treating cancer in a patient, said method comprising:
   a. obtaining a cancer tissue or cell sample from a patient after the patient has been treated with an AKT inhibitor;
   b. detecting the presence of a AKT1 or PRAS40 mutation in the cancer tissue or cell sample selected from a W80 to cysteine gene mutation in AKT1 protein and a stop codon mutation at position 178 of PRAS40 protein;
   c. diagnosing the patient with the AKT1 or PRAS40 mutation in the cancer tissue or cell sample; and
   d. administering a therapeutically effective amount of GDC-0068, (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one, or a salt thereof to the patient,
   wherein the cancer is prostate cancer.

2. The method of claim 1, further comprising detecting the expression levels of AKT3.

3. The method of claim 2, further comprising detecting overexpression of AKT3.

4. The method of claim 1, wherein the AKT inhibitor is an allosteric inhibitor.

5. The method of claim 4, wherein the allosteric inhibitor is MK-2206.

6. The method of claim 2, wherein the AKT3 expression level is mRNA expression level.

7. The method of claim 6, wherein the mRNA expression level is measured using microarray or qRT-PCR.

8. The method of claim 6, wherein the mRNA expression level is increased as compared to a reference sample.

9. The method of claim 1, wherein the cancer is associated with PTEN mutation.

10. The method of claim 1, wherein the cancer is associated with PTEN low or null status.

11. The method of claim 1, wherein the cancer is associated with PBK mutation.

12. The method of claim 1, wherein the cancer is associated with Her2/ErbB2 amplification.

13. The method of claim 1, wherein the cancer cell is a circulating tumor cell (CTC).

14. The method of claim 1, wherein detecting comprises detecting the AKT1 mutation by PCR.

15. The method of claim 1 wherein the mutation in the cancer tissue or cell sample is a W80 to cysteine gene mutation in AKT1 protein.

16. The method of claim 1 wherein the mutation in the cancer tissue or cell sample is a stop codon mutation at position 178 of PRAS40 protein.

17. A method of treating cancer in a patient that has been diagnosed with a W80 to cysteine gene mutation in AKT1 protein or a stop codon mutation at position 178 of PRAS40 protein in cancer tissue or cells from the patient, said method comprising: administering a therapeutically effective amount of GDC-0068, (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one, or a salt thereof to the patient.

\* \* \* \* \*